US010435734B2

(12) United States Patent
Kim et al.

(10) Patent No.: US 10,435,734 B2
(45) Date of Patent: Oct. 8, 2019

(54) MICRO- AND NANOPATTERNED SUBSTRATES FOR CELL MIGRATION AND USES THEREOF

(71) Applicant: UNIVERSITY OF WASHINGTON, Seattle, WA (US)

(72) Inventors: Deok-Ho Kim, Seattle, WA (US); Peter Kim, Seattle, WA (US); Andre Levchenko, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 191 days.

(21) Appl. No.: 15/556,942

(22) PCT Filed: Mar. 9, 2016

(86) PCT No.: PCT/US2016/021557
§ 371 (c)(1),
(2) Date: Sep. 8, 2017

(87) PCT Pub. No.: WO2016/145077
PCT Pub. Date: Sep. 15, 2016

(65) Prior Publication Data
US 2018/0066299 A1    Mar. 8, 2018

Related U.S. Application Data

(60) Provisional application No. 62/130,423, filed on Mar. 9, 2015.

(51) Int. Cl.
*C12Q 1/04* (2006.01)
*C12M 1/00* (2006.01)
(Continued)

(52) U.S. Cl.
CPC ............... *C12Q 1/04* (2013.01); *C12M 23/02* (2013.01); *C12M 23/12* (2013.01); *C12M 23/20* (2013.01); *G01N 33/5002* (2013.01)

(58) Field of Classification Search
None
See application file for complete search history.

(56) References Cited

U.S. PATENT DOCUMENTS 8,512,974 B2    8/2013    Murphy
8,728,817 B2    5/2014    Ogle
(Continued)

FOREIGN PATENT DOCUMENTS

WO    2008/021071 A2    2/2008
WO    2010/016916 A2    2/2010
WO    WO 13/151755    * 10/2013    ............. A61L 27/14

OTHER PUBLICATIONS

Yamada et al., "Modeling tissue morphogenesis and cancer in 3D". Cell 130, 601-610 (2007).
(Continued)

*Primary Examiner* — Allison M Fox
(74) *Attorney, Agent, or Firm* — Nixon Peabody, LLP

(57) ABSTRACT

The present invention generally relates to the field of cell growth and tissue engineering, in particular, an engineered biomimetic culture platform (BCP) that has a nanotextured and micropatterned surface that provides both chemical and mechanical cues designed to mimic the structure of the in vivo extracellular micro-environment. The BCP can be used in assays to assess the migratory behavior and/or potential of a population of cells, such as tumor cells, as well as in screening assays for diagnostic and/or prognostic purposes, or to identify agents that modify the migratory behavior or the epithelial-to-mesenchymal transition (EMT) of cells. BCPs as described herein further provide a platform for the identification of protein or genetic targets for the modification of cell migratory or invasion behavior.

23 Claims, 19 Drawing Sheets

(51) Int. Cl.
    G01N 33/50    (2006.01)
    C12M 1/32     (2006.01)

(56) References Cited

U.S. PATENT DOCUMENTS

| | | | |
|---|---|---|---|
| 9,994,812 B2* | 6/2018 | Kim | A61L 27/14 |
| 2002/0150683 A1 | 10/2002 | Troian | |
| 2007/0178534 A1 | 8/2007 | Murphy | |
| 2010/0028928 A1 | 2/2010 | Levchenko | |
| 2010/0120115 A1 | 5/2010 | Ogle | |
| 2012/0053677 A1 | 3/2012 | Ferrari | |
| 2012/0302467 A1 | 11/2012 | Levkin | |
| 2012/0322097 A1 | 12/2012 | Charest | |
| 2013/0210068 A1 | 8/2013 | Yokoyama | |
| 2015/0024967 A1 | 1/2015 | Mohapatra | |
| 2017/0016884 A1 | 1/2017 | Smith | |

OTHER PUBLICATIONS

Provenzano et al. "Shining new light on 3D cell motility and the metastatic process". Trends in cell biology 19, 638-648 (2009).
Midwood et al., "Tissue repair and the dynamics of the extracellular matrix". Int J Biochem Cell Biol, 36, 1031-1037 (2004).
Guarino "Epithelial-mesenchymal transition and tumour invasion". Int. J. Biochem. Cell Biol., 39, 2153-2160 (2007).
Guiot, et al., "Physical aspects of cancer invasion". Phys. Biol., 4, p. 1-p. 6 (2007).
Kumar et al., "Mechanics, malignancy, and metastasis: The force journey of a tumor cell". Cancer Metastasis Rev., 28, 113-127 (2009).
Pathak et al., "Transforming potential and matrix stiffness co-regulate confinement sensitivity of tumor cell migration". Integrative Biology, DOI: 10.1039/c3ib40017d 1067-1075 (2013).
Provensano et al., "Collagen reorganization at the tumor-stromal interface facilitates local invasion". BMC Medicine, 4, 38, doi:10.1186/1741-7015-4-38 1-15 (2006).
Provensano et al., "Contact guidance mediated three-dimensional cell migration is regulated by Rho/ROCKdependent matrix reorganization". Biophys. J., 95, 5374-5384 (2008).
Conklin et al., "Aligned collagen is a prognostic signature for survival in human breast carcinoma". Am J Pathol, 178, 1221-1232 (2011).
Hanahan et al., "Hallmarks of cancer: The next generation". Cell, 144, 646-674 (2011).
Samuels et al., "High frequency of mutations of the PIK3CA gene in human cancers". Science, 304, 554 (2004).
Bachman et al., "The PIK3CA gene is mutated with high frequency in human breast cancers". Cancer BiolTher, 3, 772-775 (2004).
Karakas et al., "Mutation of the PIK3CA oncogene in human cancers". Br J Cancer, 94, 455-459 (2006).
Gustin et al., "Knockin of mutant PIK3CA activates multiple oncogenic pathways". PNAS, 106, 2835-2840 (2009).
Arcaro et al., "The phosphoinositide 3-kinase pathway in human cancer: genetic alterations and therapeutic implications". Curr Genomics, 8, 271-306 (2007).
Higgings et al., "Detection of Tumor PIK3CA Status in Metastatic Breast Cancer Using Peripheral Blood." Clin Cancer Res, 18, 3462-3469 (2012).
Isakoff et al., "Breast cancer-associated PIK3CA mutations are oncogenic in mammary epithelial cells". Cancer Res, 65, 10992-11000 (2005).
Bader et al., "Cancer-specific mutations in PIK3CA are oncogenic in vivo". ProcNatlAcadSci USA, 103, 1475-1479 (2006).
Condeelis et al., "Intravital imaging of cell movement in tumours". Nat Rev Cancer. 3: 921-930 (2003).
Kim et al., "Microengineered platforms for cell mechanobiology". Annu Rev Biomed Eng, 11, 203-233 (2009).
Kim et al., "Guided three-dimensional growth of functional cardiomyocytes on polyethylene glycol nanostructures". Langmuir, 22, 5419-5426 (2006).

Kim et al., "Fabrication of nanostructures of polyethylene glycol for applications to protein adsorption and cell adhesion". Nanotechnology, 16, 2420-2426 (2005).
Peyton et al., "The effects of matrix stiffness and RhoA on the phynotypic plasticity of smooth muscle cells in a 3-D biosynthetic hydrogel system". Biomaterials, 29, 2597-2607 (2008).
Kim et al., "Nanoscale cues regulate the structure and function of macroscopic cardiac tissue constructs". ProcNatlAcadSci USA, 107, 565-570 (2010).
Suh et al., "A simple soft lithographic route to fabrication of poly(ethylene glycol) microstructures for protein and cell patterning". Biomaterials, 25, 557-563 (2004).
Khademhosseini et al., "Soft lithographic approach to fabricate patterned microfluidic channels". Anal Chem., 76, 3675-3681 (2004).
Lee et al., "Fabrication of complex patterns with a wide range of feature sizes from a single line prepattern by successive application of capillary force lithography". Langmuir, 26, 14359-14363 (2010).
Jeong et al., "UV-assisted capillary force lithography for engineering biomimetic multiscale hierarchical structures: From lotus leaf to gecko foot hairs". Nanoscale, 1, 331-338 (2009).
Suh et al., "Capillary force lithography". Advanced Materials, 13, 1386-1389 (2001).
Dickinson et al., "Patterning microscale extracellular matrices to study endothelial and cancer cell interactions in vitro". Lab Chip, 12, 4244-4248 (2012).
Liu et al., "Extracellular-controlled breast cancer cell formation and growth using non-UV patterned hydrogels via optically-induced electrokinetics". Lab Chip, DOI: 10.1039/C3LC51247A 1367-1376 (2013).
Su et al., "Geometric confinement influences cellular mechanical properties I—Adhesion area dependence". MCB, 4, 87-104 (2007).
Reyes et al., "Micropatterning neuronal cells on polyelectrolyte multilayers". Langmuir, 20, 8805-8811 (2004).
Falconnet et al., "Surface engineering approaches to micropattern surfaces for cell-based assays". Biomaterials, 27, 3044-3063 (2006).
Chang et al., "Novel high-resolution micropatterning for neuron culture using polylysine adsorption on a cell repellant, plasma-polymerized background". Langmuir, 24, 13048-13057 (2008).
Zhang et al., "Combined topographical and chemical micropatterns for templating neuronal networks". Biomaterials, 27, 5734-5739 (2006).
Nam et al., "Patterning to enhance activity of cultured neuronal networks". IEEE Proc-Nanobiotechnol, 151, 109-115 (2004).
Massobrio et al., "Modeling small-patterned neuronal networks coupled to microelectrode arrays". J Neural Eng, 5, 350-359 (2008).
Aubin et al., "Directed 3D cell alignment and elongation in microengineered hydrogels". Biomaterials, 31, 6941-6951 (2010).
Ruiz et al., "Emergence of patterned stem cell differentiation within multicellular structures". Stem Cells, 26, 2921-2927 (2008).
Rhee et al., "Patterned cell culture inside microfluidic devices". Lab Chip, 5, 102-107 (2005).
Junkin et al., "Plasma lithography surface patterning for creation of cell networks". Journal of Visualized Experiments, 52, DOI:10.3791/3115 1-4 (2011).
Song et al., "Optimal micropattern dimensions enhance neurite outgrowth rates, lengths, and orientations". Ann Biomed Eng, 35, 1812-1820 (2007).
Nelson et al., "Emergent patterns of growth controlled by multicellular form and mechanics". PNAS, 102, 11594-11599 (2005).
Thery "Micropatterning as a tool to decipher cell morphogenesis and functions". J of Cell Sci, 123, 4201-4213 (2010).
Gross et al., "Applications of microfluidics for neuronal studies". J of the Neurological Sci, 252, 135-143 (2007).
Kim et al., "Piezoelectric inkjet printing of polymers: Stem cell patterning on polymer substrates". Polymer, 51, 2147-2154 (2010).
Keyes et al., "Evaporation-induced assembly of biomimetic polypeptides". Applied Physics Letters, 93, 023120-1-02312-3 (2008).
Junkin et al., "Template-Guided Self-Assembly of Colloidal Quantum Dots using Plasma Lithography". Adv Mater, 21, 1247-1251 (2009).
Kim et al., "Guided Cell Migration on Microtextured Substrates with Variable Local Density and Anisotropy". Advanced Functional Materials, 19, 1579-1586 (2009).

(56) References Cited

OTHER PUBLICATIONS

Xia et al., "Soft Lithography". Annu. Rev. Mater. Sci., 28, 153-184 (1998).
Gates et al., "New approaches to nanofabrication: molding, printing, and other techniques". Chem. Rev., 105, 1171-1196 (2005).
Konishi et al., "Knock-in of mutant K-ras in nontumorigenic human epithelial cells as a new model for studying K-ras mediated transformation". Cancer Res., 67, 8460-8467 (2007).
Konishi et al., "A PCR-based high-throughput screen with multiround sample pooling: application to somatic cell gene targeting". Nat. Protoc., 2, 2865-2874 (2007).
Junkin et al., "Probing cell migration in confined environments by plasma lithography". Biomaterials, 32, 1848-1855 (2011).
Boguna et al., "Persistent random walk model for transport through thin slabs". Physical review E, 59, 6517-6526 (1999).
Codling et al., "Random walk models in biology". J. R. Soc. Interface, 5, 813-834 (2008).
Harms et al., "Directional persistence of EGF-induced cell migration is associated with stabilization of lamellipodial protrusions". Biophysical J., 88, 1479-1488 (2005).
Dunn "Characterising a kinesis response: time averaged measures of cell speed and directional persistence". Agents Actions, 12, 14-33 (1983).
Othmer et al., "Models of dispersal in biological systems". J. Math. Biol., 26, 263-298 (1988).
Dickinson et al., "Optimal Estimation of Cell Movement Indices from the Statistical Analysis of Cell Tracking Data". AIChE, 39, 1995-2010 (1993).
Palecek et al., "Integrin-ligand binding properties govern cell migration speed through cell-substratum adhesiveness". Nature, 385, 537-540 (1997).
Kim et al., "Effect of orientation and density of nanotopography in dermal wound healing". Biomaterials, 33, 8782-8792 (2012).
Garzon-Muvdi et al., (2012) "Regulation of Brain Tumor Dispersal by NKCC1 Through a Novel Role in Focal Adhesion Regulation". PLoS Biol 10(5) (2012) e1001320. doi:10.1371/journal.pbio.1001320.
Lamers et al., "The Influence of Nanoscale Topographical Cues on Initial Osteoblast Morphology and Migration". European Cells and Materials (20) pp. 329-343 (2010).
Nelson et al., "Preferential, enhanced breast cancer cell migration on biomimetic electrospun nanofiber "cell highways"". BMC Cancer, 14(1): 825 1-16 (2014).
Luliano et al., "Metastatic bladder cancer cells distinctively sense and respond to physical cues of collagen fibril-mimetic nanotopography". Experimental Biology and Medicine 240(5): 601-610 (2014).
Girard et al., "A 3D fibrous scaffold inducing tumoroids: a platform for anticancer drug development". PLoS One, 8(10) e75345 1-11 (2013).

\* cited by examiner

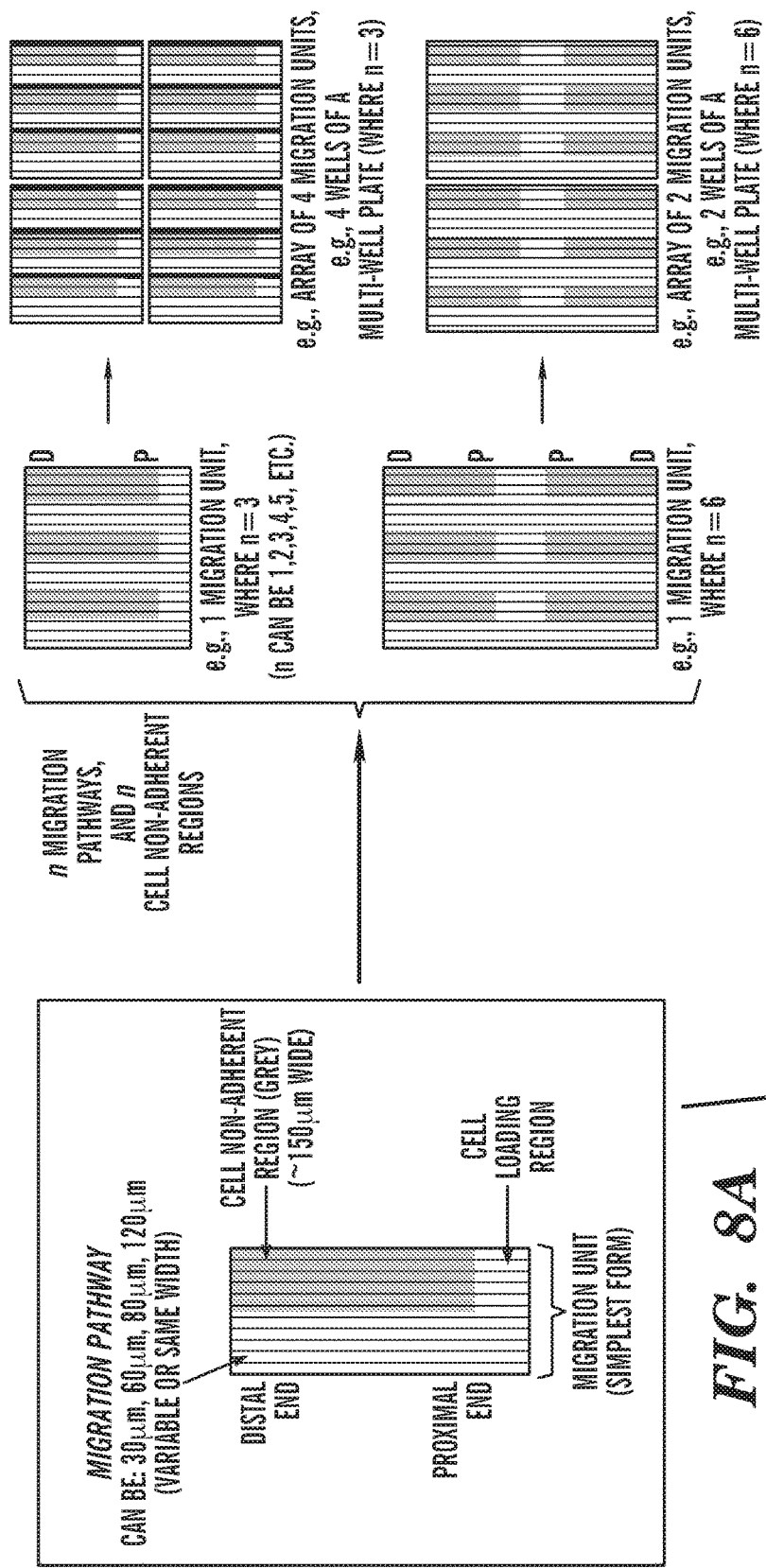

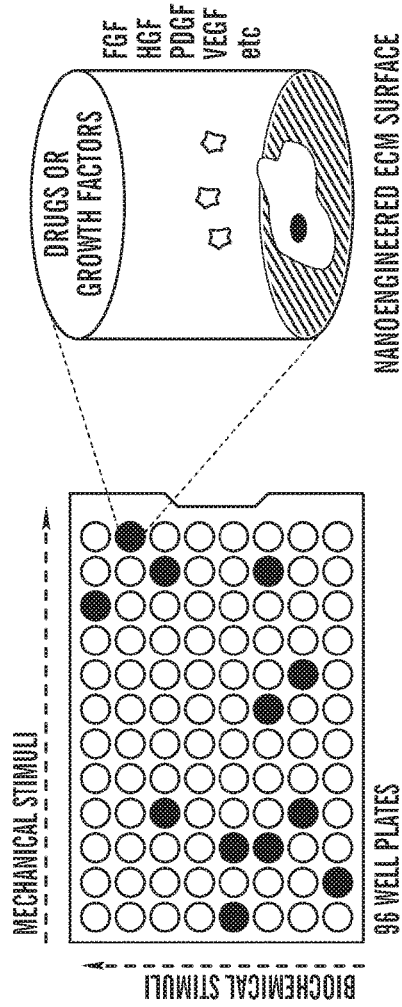
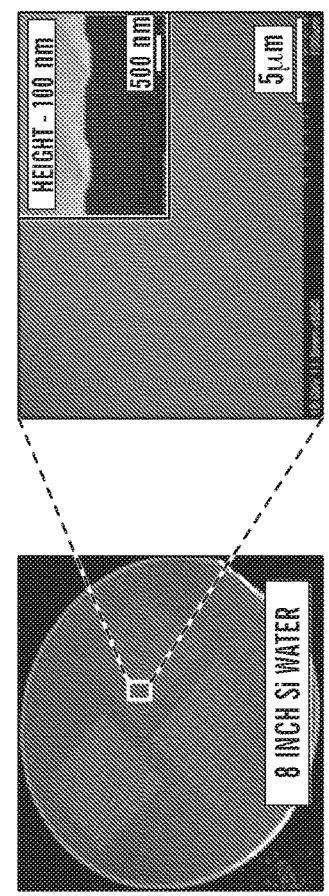
FIG. 11A
FIG. 11B
FIG. 11C

MICRO- AND NANOPATTERNED SUBSTRATES FOR CELL MIGRATION AND USES THEREOF

CROSS REFERENCE TO RELATED APPLICATIONS

This application is a 371 National Phase Entry of International Patent Application No. PCT/US16/21557 filed Mar. 9, 2016 which claims benefit under 35 U.S.C. 119(e) of U.S. Provisional Patent Application Ser. No. 62/130,423, filed on Mar. 9, 2015, the contents of which are incorporated herein by reference in their entirety.

FIELD OF THE INVENTION

The present invention generally relates to the field of cell growth and tissue engineering, in particular, methods, devices and assays comprising a nanotextured, micropatterned platform for assessing cell invasiveness and metastasis.

BACKGROUND OF THE INVENTION

One of the greatest problems in the treatment of cancerous tumors is metastasis, i.e., the transmission of cells of a primary tumor to other locations in the patient and the establishment of new tumors at such locations. Metastasis is the primary cause of mortality in cancer; therefore the invasive capacity of cells is a major factor that determines the cancer treatment plan.

Moreover, metastasis is difficult to identify and control as metastasis often occurs before a primary tumor is detected and/or diagnosed; the point(s) of metastasis can increase to multiple sites with time and become highly difficult to treat by targeting a single location of metastasis, for example, using radiation or surgery on a specific tumor. Moreover, the metastatic lesions may be in locations which limit the possible dosages of the treatments, e.g., radiation, due to the sensitivity of the surrounding tissue to such treatments. Further, metastatic cells are heterogeneous, and cells which are resistant to conventional therapy tend to emerge.

Histological evidence of invasion usually mandates surgical and/or other aggressive treatments of the tumor. In prostate cancer and breast cancer, which has 217,730 and 207,090 new cases annually in the US, the decision to perform surgical procedures, such as prostatectomy (removal of prostate) and mastectomy (removal of the breast) must be made very carefully. Surgery, though potentially lifesaving, can lead to significant morbidity or mortality. The effect of serious physiological and psychological changes on a patient's life is often severe.

Tumor cell migration is strongly influenced by the mechanical and/or micro and nanostructural features of the extracellular matrix (ECM) in the tumor microenvironment (TME)[1-3]. These regulatory relationships are particularly important during metastatic dissemination toward distant sites where tumor cells must first successfully invade through the stroma and intravasate in order to metastasize[8, 9, 10]. As patient survival rate diminishes profoundly after a secondary tumor (or multiple tumors) has formed, understanding the key processes of the early metastatic cascade (e.g. invasion) is essential. During focal and local invasion, ECM environments with varying stiffness and orientation play critical roles in regulating the successive events necessary for cell migration[9]. Indeed, recent studies demonstrate that alignment of the collagen matrix containing both nanoscale cues from collagen fibrils and microscale cues from collagen fibers in the stroma of murine mammary and human breast carcinoma drive invasion through the stroma and predict poor outcome for human breast cancer patients[6, 14, 15].

Measuring the invasion of cells isolated from tumors in an in vitro assay can yield results which are complimentary to histological examinations of tumor biopsies. The uses of existing invasion assays are limited as these typically require complex 3D imaging and time lapse microscopy. Additionally, other high-throughput invasion assays (e.g. TRANSWELL™) have limited capacity to position cells in a 3D environment. Controlled positioning of cells in 3D is possible using microfabricated hydrogels and microfluidics devices, however, these techniques require specialized infrastructure and expertise in microfabrication, and are expensive, require skilled personnel, and can only process a limited number of samples at once. Accordingly, there remains a need for a high-throughput, cost-effective method to efficiently and accurately identify cells with metastatic potential and/or invasiveness, as well screens to identify agents and compounds capable of inhibiting tumor cell migration and/or metastatic growth.

SUMMARY

The technology described herein relates to methods, compositions and kits related to an engineered biomimetic culture platform that comprises nanotopographic surface features within defined microscale constrained migration regions, where the nanotopographic surface features provide contact guidance cues for the migrating cells, and the microscale constrained migration regions promote directed cell migration of the tumor cells. The nanotopographic surface features and micropatterning of extracellular matrix (ECM)-coating on the nanotopographic surface allows independent control of geometric guidance and migratory trajectory to investigate directed migration of normal and transformed cells. In particular, the inventors have discovered herein that the nanotopography on an elastomeric substrate allows the cells to move in a directed fashion, with the migration pathways with ECM component coatings acting as geometric conduits, while nanotopography provides contact guidance to direct migration direction and enhance migration speed of the cells.

Accordingly, the engineered biomimetic culture platform disclosed herein mimics the normal extracellular matrix (ECM) and the structural and functional cues it provides to cells with migratory potential. The platform disclosed herein recapitulates the in vivo tumor environment in that it reproduces the developmental repression of tumor cells that occurs in vivo in a tumor environment and can induce the epithelial to mesenchymal transition (EMT) in normal and oncogenically transformed cells. Accordingly, the engineered biomimetic culture platform disclosed herein can be used for assessing migration of tumor cells, as well as identifying metastatic cells, or tumors with a high proportion of cells likely to become metastatic, as well as being used, for example, in screening assays to identify agents which inhibit tumor cell migration and/or EMT.

Accordingly, the technology described herein relates to methods, compositions and kits related to an engineered biomimetic culture platform ("BCP") and its use, for example, in a high-capacity and high-throughput method for measuring the migration ability (e.g., speed and/or persistence and/or alignment) of tumor and/or cancer cells. The biomimetic culture platform, as disclosed herein, provides an assay and method for determining and quantitating the migration ability, and therefore metastatic potential of a population of cancer cells.

The engineered biomimetic culture platform described herein generally relates to a nanotextured substrate comprising a polymer substrate which has a nanotextured array of parallel grooves and ridges (referred to herein as nanopattern or nanogrooved topology). On the surface of the nanotextured array of parallel grooves and ridges are defined cell permissive (or cell adherent) regions, referred to herein as migration pathways, that comprise an extracellular matrix (ECM) coating. These defined regions are in a micropattern and serve as geometric conduits directing the migratory trajectory of the cells. Thus, the engineered biomimetic culture platform described herein is unique in that it combines the synergistic action of nanoscale cues (provided by the nanopattern) for contact guidance of migrating cells, with microscale cues provided by the migration pathways to direct anisotropic diffusion behavior of the migrating cells, thereby providing a culture platform mimicking the extracellular matrix.

Therefore, the technology described herein relates to the use of a biomimetic culture platform that provides a more defined method of looking at migration—in particular, the biomimetic culture platform allows speed, alignment and persistence of tumor cells to be analyzed in a high throughput assay. As the biomimetic culture platform can be configured in a multi-well format, it allows comparison of multiple different cancer cell samples and cell types and/or agents in a single experiment or assay. As such, a multi-well engineered biomimetic culture platform permits rapid, simple screening of migratory behavior that can be employed for research and clinical applications, such as personalized medicine. Moreover, a multi-well array format of biomimetic culture platform (BCP) provides a migration assay platform allowing complex analysis of multiple cancer populations in a HTS, requiring only ~1000 cells per individual cell migration unit.

In some embodiments, an engineered biomimetic culture platform as disclosed herein comprises a nanopatterned surface and comprises, on the nanopatterned surface an array of at least one repeatable micropattern unit, referred to as a cell migration unit, where the cell migration unit comprises (i) at least one cell permissive region, referred to as a migration pathway (serving as a microscale geometric conduit) directing anisotropic diffusion behavior of the cells, (ii) at least one cell non-adherent region adjacent to the migration pathway, and (iii) at least one cell loading region at the proximal end of the migration pathway (an optionally at the proximal end of the hydrophobic region). Exemplary cell migration units are shown in FIGS. 8A-8D. In some embodiments, multiple migration pathways (i.e. cell permissive regions) and cell non-adherent regions can be present, and multiple cell migration units are present on a single nanopatterned platform, thereby forming an array of cell migration units.

One aspect of the technology described herein relates to the use of the biomimetic culture platform in a method for assessing metastatic potential of cancer cells or cancer stem cells, for example, in the analysis of migratory behavior among different tumors, e.g., tumor samples obtained from multiple different patients, or for personalized medicine. In part because of the relatively small number of cells required for assays as described herein, the biomimetic culture platform is particularly beneficial for screening of primary or inoperative human tissues/tumors where the cellular resource (e.g., biopsy sample) may be considerably limited.

Another aspect of the technology described herein relates to use of the biomimetic culture platform in a method for prognosis of cancer. For example, the assays as described herein can be used to assess the migratory behavior of a tumor sample (e.g., tumor biopsy) obtained from a subject with cancer, and where the migration speed of the tumor cells in the sample is above a certain threshold, e.g., at least 0.5-fold faster than control/non-metastasis cancer cell; or e.g. having a migration speed of at least 20 μm/hr, the tumor cells are identified to have a high migratory potential and the subject is identified as having an aggressive or metastatic cancer. In some embodiments, the subject may have a poor prognosis and is selected for, or administered, a more aggressive cancer treatment as compared to a subject whom has a tumor where the cells migrate at a speed of, e.g., less than 20 μm/hr.

Another aspect of the technology described herein relates to use of the biomimetic culture platform in a method for determining cell heterogeneity in a population of tumor cells, e.g., tumor cells obtained from a subject. In some embodiments, the biomimetic culture platform can be used to determine if a subject's tumor comprises a high proportion of migratory cancer cells, and therefore has an aggressive cancer, and/or a heightened risk of cancer reoccurrence.

Accordingly, other aspects of the technology described herein relate to the use of the biomimetic culture platform to screen for agents and compounds capable of influencing, i.e., inhibiting cell migration, e.g., reducing any one or more of speed of migration, persistence, etc., and thereby inhibiting the metastatic potential of a cancer cell population. The methods, compositions and assays comprising a biomimetic culture platform assay as disclosed herein provides a highly sensitive assay system capable of mimicking the in vivo tumor environment and the extracellular matrix (ECM).

Other aspects of the technology described herein relate to the use of the biomimetic culture platform in a method to screen for agents and compounds capable of inhibiting or reducing EMT (epithelial-to-mesenchymal transition) of normal or tumor cells, thereby inhibiting the metastatic potential of a cancer cell population.

Other aspects of the technology described herein relate to the use of the biomimetic culture platform as disclosed herein as a research tool, e.g., to isolate tumor cells that have a high migratory potential, e.g., that have a higher migratory speed and/or persistence as compared to other cancer cells, and in some embodiments, to isolate cancer stem cells.

Accordingly, one aspect of the technology described herein relates to an array for assessing cell migration comprising: (a) nanopatterned substrate comprising parallel grooves and ridges, wherein the groove width is between 200 nm to 3000 nm, the ridge width is between 200 nm to 3000 nm, and depth of the groove is between 200 nm to 3000 nm; and (b) an array of at least one cell migration unit on the nanopatterned substrate, each cell migration unit comprising: (i) at least one migration pathway having a proximal and distal end, (ii) at least one cell non-adherent region having a proximal and distal end, and (iii) at least one cell loading region; where the at least one migration pathway comprises a cell adherent surface having a width between 10 μm-500 μm, aligned parallel to the grooves and ridges, wherein the at least one cell non-adherent region is aligned parallel to the grooves and ridges and is adjacent to the at least one migration pathway; and wherein the at least one cell loading region is located at the proximal end of the at least one migration pathway and optionally, at the proximal end of at least one cell non-adherent region.

In some embodiments, the at least one migration pathway is coated with an extracellular matrix (ECM) component coating comprising, for example, collagen, laminin, fibronectin and the like, and optionally growth factors, glycoproteins, proteoglycans and/or chemotaxis agents or functional fragments thereof. In some embodiments, the ECM component coating does not comprise laminin.

In some embodiments, as shown for example, in FIG. 8A-8D, the array comprises a cell migration unit that comprises n migration pathways, n cell non-adherent regions, and at least one cell loading region located at the proximal end of the n migration pathways and n cell non-adherent regions. In some embodiments, the array comprises a cell migration unit that comprises n migration pathways, n+1 cell non-adherent regions, and at least one cell loading region located at the proximal end of the n migration pathways and n+1 cell non-adherent regions, wherein each of the n migration pathways has a cell non-adherent region located on either side. In some embodiments, the array can comprise a cell migration unit that comprise n migration pathways, n+2 cell non-adherent regions, and at least one cell loading region located at the proximal end of the n migration pathways and n+2 cell non-adherent regions, wherein each of the n migration pathways has a cell non-adherent region located on either side. In some embodiments, n is 2 and each cell migration unit comprises at least 2 migration pathways, at least 2 cell non-adherent regions and at least one cell loading region. In some embodiments, n is selected from, 2, 3, 4, 5, 6, 7, 8, 9, 10, between 11-15, between 16-20 or more than 20 but less than 50. In some embodiments, the migration pathways of a cell migration unit are of the same width, and can be selected from any of 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, or greater than 150 μm but less than 3000 μm. In some embodiments, the migration pathways of a cell migration unit are are of different widths, and can be selected from a combination of widths, for example but not limited to any or a combination of: 10 μm, 20 μm, 30 μm, 40 μm, 50 μm, 60 μm, 70 μm, 80 μm, 90 μm, 100 μm, 110 μm, 120 μm, 130 μm, 140 μm, 150 μm, or greater than 150 μm but less than 500 μm. In some embodiments, a cell non-adherent region in a migration unit is between about 20 μm-500 μm in width, or between about 150 μm and about 500 μm in width.

In some embodiments, the array comprises a nanotexture that has a groove width of between about 200 nm-800 nm, the ridge width is between about 200 nm to 800 nm, and ridge height is between about 200 nm to 800 nm. Other dimensions are also encompassed, for example, but not limited to, a groove width is between about 800 nm-1200 nm, the ridge width is between about 800 nm to 1200 nm, and ridge height is between about 800 nm to 1200 nm, or a groove width is between about 1000 nm-2000 nm, the ridge width is between about 1000 nm-2000 nm, and ridge height is between about 1000 nm-2000 nm, or a groove width is between about 2000 nm-3000 nm, the ridge width is between about 2000 nm-3000 nm, and ridge height is between about 2000 nm-3000 nm.

In some embodiments, the array comprises cell migration units that have at least one migration pathway and the at least one cell non-adherent region is between about 0.5 mm-10 mm in length, or between about 10 mm-20 mm in length.

In some embodiments, the array comprises any number of cell migration units, e.g., at least 2, at least 3, at least 6, at least 8, at least 12, at least 24, at least 48, at least 96, at least 384, at least 1536 cell migration units, or any number between 1-1536. In some embodiments, the array is configured as a multi-well plate, each well of the multi-well plate comprising at least one cell migration unit, for example, where a multi-well plate comprises any of: 2, 3, 4, 6, 8, 12, 24, 48, 96, 384 or 1526 wells.

In some embodiments, an array can further comprise a removable barrier located at the proximal end of the at least one migration pathway and optionally at the proximal end of the at least one cell non-adherent region, wherein the barrier prevents cells present in the cell loading region from entering the migration pathway, for example, a where the removable barrier is a micropatterned stamp.

Accordingly, one aspect of the technology described herein relates to an array of migration units as disclosed herein comprising a population of mammalian cells, for example, epithelial cells (e.g., normal epithelial cells and/or cancer or tumor epithelial cells, such as those removed from an epithelial tumor). Of course, other cell types are encompassed for use on the array, as disclosed herein, for example blood cells, neuronal cells, keratinocytes, fibroblasts, oligodendrocytes, cartilage, or Schwann cells. In some embodiments, the population of cells are mammalian cells, which are loaded and cultured on the substrate at least in the cell loading region. In some embodiments, the cells are human cells. In some embodiments, the cells are tumor cells, for example, but not limited to epithelial tumor cells.

One aspect of the technology described herein relates to a micro-well plate comprising the array disclosed herein.

Another aspect of the technology described herein relates to a method for assessing the metastatic potential of a population of tumor cells, comprising: (a) seeding a population of tumor cells onto a nanopatterned substrate comprising parallel grooves and ridges, wherein the groove width is between 200 nm to 3000 nm, the ridge width is between 200 nm to 3000 nm, and height is between 200 nm to 3000 nm, wherein the tumor cells are seeded at a cell loading region of at least one cell migration unit; wherein the cell migration unit comprises, (i) at least one migration pathway having a proximal and distal end, (ii) at least one cell non-adherent region having a proximal and distal end, and (iii) at least one cell loading region; wherein the at least one migration pathway is aligned parallel to the grooves and ridges and comprises a cell-adherent surface, and is between 10 μm-500 μm in width; wherein the at least one cell non-adherent region is aligned parallel to the grooves and ridges and is adjacent to the at least one migration pathway; and wherein the at least one cell loading region is located at the proximal end of the at least one migration pathway and optionally, at the proximal end of at least one cell non-adherent region; (b) culturing the tumor cells in the cell loading region to form a monolayer; (c) optionally removing a barrier located between the proximal end of the at least one cell migration pathway and the cell loading region; (d) culturing the tumor cells for a selected period of time to allow migration of the cancer cells along the migration pathway towards the distal end; (e) measuring the distance of cell migration of the population of tumor cells towards the distal end of the migration pathway in the selected period of time.

Another aspect of the technology described herein relates to a method for measuring cell migration, the method comprising: (a) seeding a population of cells onto a nanopatterned substrate comprising parallel grooves and ridges, wherein the groove width is between 200 nm to 3000 nm, the ridge width is between 200 nm to 3000 nm, and height is between 200 nm to 3000 nm, wherein the cancer cells are seeded at a cell loading region of at least one cell migration unit; wherein the cell migration unit comprises, (i) at least one migration pathway having a proximal and distal end, (ii) at least one cell non-adherent region having a proximal and distal end, and (iii) at least one cell loading region; wherein the at least one migration pathway is aligned parallel to the grooves and ridges and comprises a cell-adherent surface, and is between 10 µm-500 µm in width; wherein the at least one cell non-adherent region is aligned parallel to the grooves and ridges and is adjacent to the at least one migration pathway; and wherein the at least one cell loading region is located at the proximal end of the at least one migration pathway and optionally, at the proximal end of at least one cell non-adherent region; (b) culturing the population of cells in the cell loading region to form a monolayer; (c) optionally removing a barrier located between the proximal end of the at least one cell migration pathway and the cell loading region; (d) culturing the population of cells for a selected period of time to allow migration of the cells along the migration pathway towards the distal end; (e) measuring the distance of cell migration of the population of cells towards the distal end of the migration pathway in the selected period of time.

In some embodiments, the cells are allowed to migrate along the migration pathways for a sufficient time to permit cell migration along the migration pathway towards the distal end, for example, such selected period of times include, but are not limited to, any of: 20 mins, 30 mins, 1, 2, 3, 6, 8, 10, 12, 24, 36 or 48 hours. In some embodiments, time-lapse images are collected or performed at desired intervals for a series of images during the selected period of time, e.g., at approximately 10- or 20- or 30- or 45 minute intervals, or every hour, or every 2 hours etc.

In some embodiments, the methods of measuring cell migration and/or assessing the metastatic potential of a population further comprise measuring the distance of cell migration of a population of cells towards the distal end of the migration pathway in the selected period of time in the presence of a test agent, relative to the distance of cell migration of a population of the same cells in the absence of the test agent. In some embodiments, the methods of measuring cell migration and/or assessing the metastatic potential of a population further comprise determining the migration speed of the population of cells in the selected period of time.

In some embodiments, the methods of measuring cell migration and/or assessing the metastatic potential of a population further comprise determining the migration speed of a population of cells in the selected period of time in the presence of a test agent, relative to the migration speed of the same population of cells in the absence of the test agent.

In some embodiments, a barrier between the proximal end of the at least one cell migration pathway and the cell loading region is a micropatterned stamp, as disclosed herein. In some embodiments, the methods of measuring cell migration and/or assessing the metastatic potential of a population further comprise seeding the population of cells in the cell loading region in a gel or hydrogel, therefore, when media is added the cells to the array, the cells can migrate out of the gel or hydrogel and along the migration pathways.

In some embodiments, the methods of measuring cell migration and/or assessing the metastatic potential can be used to measure the migration of population of tumor cells, e.g., epithelial tumor cells or tumors of epithelial origin, e.g., breast mammary cells, colon cells and the like. In some embodiments, the tumor cells are selected from any of invasive tumor cell, breast cancer cells, prostate cancer cells, colon cancer cells, melanoma cancer cells, ovarian cancer cells, cervical cancer cells, hepatic cancer cells, lung cancer cells and SSC In alternative embodiments, the methods of measuring cell migration and/or assessing the metastatic potential can be used to measure the migration of population of cells comprising, among other cells, any cell type, or a combination of cell types selected from, blood cells, neuronal cells, keratinocytes, fibroblasts, oligodendrocytes, cartilage, or Schwann cells. In some embodiments, the BCP and methods as discussed herein do not comprise brain tumor cells and/or glioblastoma cells.

In some embodiments, the methods of measuring cell migration and/or assessing the metastatic potential can further comprise a step of collecting a population of cells from the migration pathway after the selected period of time, for example, where a population of cells that have migrated furthest along the migration pathway in the selected period of time are collected, e.g., where a population of cells located in the distal one-third of the migration pathway after the selected period of time are collected.

In some embodiments, the methods of measuring cell migration and/or assessing the metastatic potential can further comprise a step of measuring the distance of cell migration of a population of tumor cells towards the distal end of the migration pathway in the selected period of time in the presence of a test agent, relative to the distance of cell migration of a population of the same tumor cells in the presence of different concentrations of the test agent, and/or the presence of an agent known to inhibit cell migration, and/or the presence of an agent known to promote cell migration. In some embodiments, the method can further comprise as step of measuring the distance of cell migration of a population of tumor cells towards the distal end of the migration pathway in the selected period of time in the presence of a test agent, relative to the distance of cell migration of a population of cells known to migrate at a particular rate.

In some embodiments, the methods of measuring cell migration and/or assessing the metastatic potential can further comprise a step of measuring the proportion of cells in a cell population that migrate one or more chosen distances in the selected period of time.

In some embodiments, the methods of measuring cell migration and/or assessing the metastatic potential can be used to determine migration speed of a cell population, and where a migration speed of more than 20 µm/h is detected on a 120 µm width migration pathway with nanogrooves of 800 nm ridge width, 800 nm groove width and 600 nm groove depth, the cell population is identified to comprise metastatic cells. In some embodiments, when the cell population is identified to have a migration speed of more than 20 µm/h, selecting the subject from whom the cells were obtained for a more aggressive cancer therapy than indicated when the cells are not metastatic.

Another aspect of the technology described herein relates to a method for identifying an agent which influences the migration of a population of cancer cells, comprising using a method of measuring cell migration and/or assessing the metastatic potential as disclosed herein in the presence and absence of a test agent. For example, in some embodiments, where an agent that inhibits the migration of the cancer cells along the migration pathway in a selected period of time by at least 10% relative to migration in the absence of the agent is identified as an inhibitor of migration of the cancer cells.

Another aspect of the technology described herein relates to a method of fabricating an array, where such an exemplary method is shown in FIG. 1. In some embodiments, such a method comprises: (a) providing a nanopatterned substrate, wherein the nanopatterned stamp comprises parallel grooves and ridges, wherein the groove width is between 200 nm to 3000 nm, the ridge width is between 200 nm to 3000 nm, and height is between 200 nm to 3000 nm; (b) placing a micropatterned stamp on the nanopatterned substrate, wherein the micropatterned stamp comprises an array of at least one unit, each unit comprising: (i) a ridge having a width of between 50 μm-500 μm, wherein the ridge has a proximal and distal end; (ii) a groove having a width of between 10 μm-300 μm, wherein the groove has a proximal and distal end; and (iii) a void at the proximal end of the groove and, optionally at the proximal end of the ridge; (c) treating the nanotextured substrate comprising the micropatterned stamp to change the exposed nanotextured substrate from a hydrophobic surface to a hydrophilic surface, wherein the non-exposed substrate is a cell non-adherent surface; (d) coating the nanotextured cell surface with an extracellular matrix component coating.

In some embodiments, a method of fabricating an array comprises an initial step of generating the nanopatterned substrate, comprising using a nanopatterned stamp to disperse PDMS on a substrate to generate a nanopattern on the substrate, and removing the nanopatterned stamp after the nanopattern is generated, wherein the nanopatterned stamp comprises grooves and ridges, wherein the groove width is between 200 nm to 3000 nm, the ridge width is between 200 nm to 3000 nm, and height of the ridge is between 200 nm to 3000 nm. In some embodiments, a method of fabricating an array comprises treating the nanotextured substrate to change the substrate from a hydrophobic surface to a hydrophilic surface using oxygen plasma treatment or a comparative method. In some embodiments, the array substrate is glass, and can be, in some embodiments, a glass coverslip that can be placed in a well of a multi-well plate (i.e., each glass coverslip with the nanogrooves and a micopattern of one or more migration units can be inserted into a well of a 2, 3, 4, 6, 8, 12, 24, 48, 96, 384 or 1526 multi-well plate).

In some embodiments a nanopatterned stamp used in fabricating an array is a PUA master stamp. In some embodiments, a micropatterned stamp used in fabricating an array is a PDMS master stamp, and can, in some embodiments, comprise an array of 2, 3, 4, 6, 8, 12, 24, 96, 384 or 1526 units compatible with a multi-well plate comprising 2, 3, 4, 6, 8, 12, 24, 48, 96, 384 or 1526 wells. In some embodiments, a method of fabricating an array optionally comprises a step of adding walls of a micro-well plate to generate a multi-well plate comprising 2, 3, 4, 6, 8, 12, 24, 48, 96, 384 or 1526 wells. Alternatively, a nanopatterned stamp used in fabricating an array is configured to generate a nanopatterned cell surface in each well of a 2, 3, 4, 6, 8, 12, 24, 48, 96, 384 or 1526 multi-well plate. In some embodiments, a micropatterned stamp comprises an array of 2, 3, 4, 6, 8, 12, 24, 48, 96, 384 or 1526 units and is configured such that each unit generates a micropattern on a nanopatterned cell surface in each well of 2, 3, 4, 6, 8, 12, 24, 48, 96, 384 or 1526 multi-well plate.

Another aspect of the technology described herein relates to a kit for measuring migration properties of a cell, the kit comprising the array disclosed herein.

Another aspect of the technology described herein relates to a a kit comprising a nanopatterned substrate, a micropatterned stamp, and reagents for an ECM component coating, wherein the nanopatterned substrate comprises parallel grooves and ridges, wherein the groove width is between 200 nm to 3000 nm, the ridge width is between 200 nm to 3000 nm, and height is between 200 nm to 3000 nm.

Another aspect of the technology described herein relates to a kit comprising a nanopatterned stamp, a micropatterned stamp, reagents for an ECM component coating, wherein the nanopatterned substrate comprises parallel grooves and ridges, wherein the nanopatterned stamp is configured to generate a parallel grooves and ridges, wherein the groove width is between 200 nm to 3000 nm, the ridge width is between 200 nm to 3000 nm, and height is between 200 nm to 3000 nm. In some embodiments, a kit disclosed herein can comprise a micropatterned stamp having an array of at least one unit, each unit comprising: (i) a ridge having a width of between 50 μm-500 μm, wherein the ridge has a proximal and distal end, (ii) a groove having a width of between 10 μm-300 μm, wherein the groove has a proximal and distal end; and (iii) a void at the proximal end of the groove and, optionally at the proximal end of the ridge.

Invasive nature of aggressive cancers highlights the importance of assaying cell migration as a phenotypic feature potentially predictive of clinical outcomes. Further, extracellular matrix topology is important in the regulation of cell function (Kim et al., Matrix nanotopology as a regulator of cell function, J. Cell Biol., 2012; 197(3); 351-360). Herein, the biomimetic culture platform provides a simple but information-rich experimental method recapitulating the in vivo tumor microenvironment that allows detailed analysis of primary patient samples in an easy high throughput manner. Using this method on a range of patient derived samples and contrasting the results of the analysis with respective clinical information revealed substantial predictive power, demonstrating that cell migration, as examined in structured, mechanically-defined culture conditions, can indeed be predictive of more complex in vivo invasion processes and can be used as a powerful phenotypic analysis tool with strong clinical implications.

The biomimetic culture platform described herein has important advantages over other phenotypic analysis platforms designed to assay cell invasion. For instance the trans-well migration analysis, another relatively simple method directly assaying cell invasion, for which a multi-well design has also been described, usually requires at least an order of magnitude greater numbers of cells than the method we describe here. More importantly, classical trans-well assays fail to yield the information on migration and morphology of each individual cell. This missing information can be critical in the analysis of human tumors. For example, knowledge of the degree of population heterogeneity can be critical to the decision making in the clinic. Furthermore, both the speed and trajectory of individual cells in a tumor cell population can be used to predict the time to recurrence of tumors in the patients from whom the samples were obtained. Such information is particularly useful in prognostic analyses of tumor samples at the time of surgery. Additionally, the biomimetic culture platform permits analysis of individual cell migration properties, which is also of critical importance.

Furthermore, the biomimetic culture platform described herein is a result of careful engineering to recapitulate the in vivo environment of the extracellular milieu involves in tumor cell migration, providing both chemical and mechanical cues on both a nano- and micro-scale level, with the combined nano-scale topography and micropatterned ECM-coated regions designed to mimic the structure of in vivo extracellular cell micro-environment. The inventors demonstrate herein that the nano-scale topography and micropatterned ECM-coated regions provide surprisingly remarkable synergistic influence to guide, in vitro cellular responses as they occur in vivo.

The biomimetic culture platform provides a flexible and multi-faceted bio-mimetic assay for screening of multiple samples and/or multiple conditions in assaying patient samples, with an array of the repeatable cell migration unit providing an advantage of simplifying the analysis of cell migration of multiple tumor samples at the same time, yet allowing detailed information rich output (e.g., speed, persistence and/or alignment) in a high-throughput manner. Further, the migration pathways in each cell migration unit permits analysis of the migration of cells primarily in one-dimensional paths, yet assessing random path movement versus directed direction migration of the tumor cells in different geometric conduit widths. As such, the biomimetic culture platform as described here easy to use in both academic and clinical settings.

The technology described herein also relates to kits comprising the biomimetic culture platform as disclosed herein. In some embodiments, the kit also comprises reagents and agents for coating the biomimetic culture platform with cell populations comprising tumor cells. In some embodiments, the kit can optionally comprise the biomimetic culture platform organized a multi-well culture plate for use in the assays and methods as disclosed herein, for example, in screening assays to identify agents which influence (e.g., inhibit) the migratory behavior of the tumor cells, or EMT of tumor cells, as well as comparing the migratory behavior of different tumor call populations and/or effects of different nanoscale cues and/or micropatterning (e.g., different ECM-coatings, different widths of the migration pathways etc.) on the migratory behavior of same tumor cell population.

The technology described herein also relates to kits comprising a nanopatterned substrate and a micropatterned stamp and reagents for ECM component coating, thereby enabling the kit user to generate or fabricate a biomimetic culture platform as disclosed herein. In some embodiments, the kit comprises a nanopatterned stamp, a micropatterned stamp and reagents for ECM component coating, thereby enabling the kit user to generate or fabricate a biomimetic culture platform as disclosed herein.

Definitions

For convenience, certain terms employed in the entire disclosure (including the specification, examples, and appended claims) are collected here. Unless defined otherwise, all technical and scientific terms used herein have the same meaning as commonly understood by one of ordinary skill in the art to which this invention belongs.

The term "biomimetic culture platform" is used interchangeably herein as "BCP" and refers to a substrate comprising a nanotextured surface which is micropatterned with an array of one or more cell migration units.

The term "nanotextured" is used interchangeably herein with "nanopatterned", "nanogrooved", "nanotopographic features" or "nanotopography", and refers to a repeating pattern of substantially parallel grooves and ridges, where the height, depth and width of the grooves and ridges are of sub-micron scale or widths of less than 3 µm (i.e., less than 3000 nm). A nanopatterned texture of a repeating pattern of substantially parallel grooves and ridges encompasses the dimensions of groove widths between 1 nm-3000 nm, ridge widths of between 1-3000 nm, and height of the ridges between 1-3000 nm (or depth of the grooves between 1-3000 nm)—that is, in some embodiments, the nanotexture has dimensions of more than 1 nm and less than 3000 nm.

The term "micropatterned" or "micropattern" as used herein refers to a repeating micron scale pattern of ECM-coated regions on the nanopatterned surface. The micropattern serves as geometric conduits for cell migration, where the micropattern is equal to, or above 3 µm but no larger than 500 µm. In some embodiments, the micropattern is a pattern of migration pathways that are of a micron scale. In some embodiments, a micropattern is a repeating pattern of individual migration units.

The term "cell migration unit" refers to a single unit of repeatable micropattern comprising a cell permissible region, cell non-adherent region, and a cell loading area. A biomimetic culture platform may comprise a single (i.e., one) cell migration unit, or may comprise a plurality of cell migration units arranged in an array format, e.g., for analysis of the migration behavior of more than one cell sample at a time. The array of cell migration units can be an array of 2, 3, 4, 6, 8, 10, 12, 24, 36, 48, 96, 384, 1526 cell migration units, which can have the same, or different geometric micropatterns, on a single biomimetic culture platform.

The term "migration pathway" refers to a cell adherent region on a nanogrooved substrate that is of a defined geometric configuration and which directs the trajectory of the migration of the cultured cells, e.g., tumor cells. A migration pathway typically has a microscale width between 10-500 µm that serves as a surface geometric conduit to channel, or direct, the migration of the cultured cells in a particular direction. In some embodiments, the migration pathways are geometric conduits of different geometries, such as rectangular regions (or strips) having width dimensions of between 3 µm-500 µm.

The term "cell adherent region" is used interchangeably herein with "cell permissive region" and refers to a region of a cell migration unit comprising a coating on the nanotextured substrate that permits cell adhesion and migration. A cell adherent region is bounded by at least one non-adherent region which together define a cell migration pathway. While it is preferred that a cell non-adherent region does not permit cell adhesion at all, at the minimum, a cell adherent region allows at least 75% more cells to attach to the surface relative to the proportion of cells attaching to the same surface area of a cell non-adherent region. A region of a nanogrooved substrate as defined herein is typically coated with an ECM-component coating to create a cell adherent region.

The term "extracellular matrix" or "ECM" as used herein refers to a complex structural entity surrounding and supporting cells that is found in vivo within mammalian tissues. The ECM is often referred to as the connective tissue and collection of extracellular molecules secreted by cells that provides structural and biochemical support to the surrounding cells. The composition of ECM varies between multicellular structures; however, cell adhesion, cell-to-cell communication and differentiation are common functions of the ECM. The ECM is primarily composed of three major classes of biomolecules including structural proteins such as collagens and elastins, specialized proteins such as fibrillins, fibronectins, and laminins, and proteoglycans.

As used herein, the term "extracellular matrix component" refers to one or more protein or non-protein components of the ECM which, when coated onto or incorporated into an otherwise substantially non-cell-adherent surface, permits or promotes cell adherence to and permits cell migration upon such surface. Examples include, but are not limited to fibronectin, laminin, varied forms of collagen, elastin, glycoproteins, proteoglycans, glycosaminoglycans and polysaccharides, including non-proteoglycan polysaccharides. Fragments of ECM component polypeptides that permit or promote cell adhesion to otherwise substantially non-cell-adherent surfaces are also considered extracellular matrix components as the term is used herein.

As used herein the term "extracellular matrix-coating" or "ECM-coating" or "extracellular matrix component coating" comprises at least a soluble and/or non-soluble fraction of native ECM or a portion thereof that permits cell adhesion when the coating or component is applied to a cell non-adherent substrate. A non-soluble fraction of ECM includes secreted ECM proteins and biological components. Collagen is an exemplary ECM-coating, as well as laminin. Collagen is the main protein of connective tissue and the most abundant protein in mammals, making up about 25% of the total protein content. There are currently at least 28 types of collagen described in the literature (see, e.g., Tables 1 and 2 in US application No., US20100047305 for a detailed listing). Over 90% of the collagen in the body is in the form of Collagens I, II, III, and IV. Different collagen materials have been used for treatment of soft tissue defects, such as reconstituted injectable bovine collagen, crosslinked collagen, or other xenogeneic collagens. Use of naturally secreted ECM compositions have also been described (U.S. Pat. No. 6,284,284). Any such collagens are contemplated for use in the ECM-coating or ECM component as described herein.

The term "cell non-adherent region" refers to the surface of the nanotextured substrate onto which cells do not substantially, or substantially attach. A cell non-adherent region allows no more than 5% of cells to attach to the surface, relative to the proportion of cells attaching to the same surface area of a cell adherent region. A cell non-adherent region may comprise a hydrophobic surface.

The term "cell loading region" refers to part of a cell migration unit where a cell population is introduced and cultured for a predefined time period, or to a pre-defined cell density, prior to monitoring the migration behavior. A cell loading region is connected to the proximal end of a migration pathway. In some instances, the cell loading region can be configured to allow placement of a removable cell impermeable barrier which separates or prevents the cells in the cell loading region from entering the migration pathway during the pre-defined period of time when the cells are cultured in the cell loading region (i.e., before the beginning of the assay and/or prior to monitoring the migration behavior of the cells).

The term "cell impermeable" as used herein with respect to a cell impermeable barrier refers to a structural barrier that prevents cells from entering the migration pathway while the cell impermeable barrier is present. The cell impermeable barrier may be removable and structural, i.e., such as a structural divider between the cell loading region and the migration pathway, or a micropatterned stamp present on the nanotextured substrate.

The term "migration behavior" of a population of cells is used interchangeably herein with "migration properties" and refers to one or more of the migration properties of: cell migration speed (measured in, e.g., μm/hr), persistence time (measured in mins), or alignment.

The term "migration speed" refers to the furthest distance migrated by an individual cell, or average furthest distance migrated by a collection of cells in a predetermined time period.

The term "alignment" refers to the ratio of the distance moved parallel to a set of nanogrooves versus distance moved perpendicular to the nanogrooves. Alignment describes how strongly the cells interact with the nanogrooves, i.e., the direct contact cues. Both spindle shape factor and alignment have been reported to correlate with the structure and strength of the cell—substrate adhesion complexes which are critical regulators of cell motility and morphology.

The term "persistence" refers to continuous motion in a particular direction. Persistence distinguishes the cells movement/motility as a migratory movement as opposed to random exploratory motility. Persistence is a critical migratory model for tumor dispersal and is quantified as the ratio of the shortest starting point-to-end point distance travelled compared to the total distance traveled in the complete cell trajectory.

The term "anisotropic" refers to items, such as cells, being spatially organized or arranged in a direction-related manner. That is, an ansiotropic cell will have different dimensions along different axes.

The term "soft-lithography" as used herein refers to a technique commonly known in the art. Soft-lithography uses a patterning device, such as a stamp, a mold or mask, having a transfer surface comprising a well defined pattern in conjunction with a receptive or conformable material to receive the transferred pattern. Microsized and nanosized structures are formed by material processing involving conformal contact on a molecular scale between the substrate and the transfer surface of the patterning device.

A "patterning device" is intended to be broadly interpreted as referring to a device that can be used to convey a patterned cross-section, corresponding to a pattern that is to be created in a target portion of the substrate.

A "pattern" is intended to mean a pre-determined mark or design, generally a substantially nanoscale design of repeating parallel grooves and ridges in a surface as described herein.

The term "substrate" is used interchangeably herein with "scaffold" and should be understood in this connection to mean any suitable carrier material to which the cells are able to attach or adhere (either inherently or following treatment to promote cell adhesion) and which can be nanotextured and micropatterned as described herein. In some embodiments, the substrate is a "biocompatible substrate" as that term is defined herein. In one embodiment, the biocompatible substrate provides the supportive framework that allows cells to attach to it, and grow on it. Cultured populations of cells can then be grown on the biocompatible substrate, which includes the nanotextured substrate that provides the appropriate cues for cell migration and for example, for establishing interstitial distances required for cell-cell interaction.

The term "elastomeric substrate" as used herein refers to a substrate that is a polymer with viscoelasticity (having both viscosity and elasticity) and very weak inter-molecular forces, generally having low Young's modulus and high failure strain compared with other materials.

The term "phenotype" refers to one or a number of total biological characteristics that define a cell or organism under a particular set of environmental conditions and factors, regardless of the actual genotype. A phenotype can be expressed markers (e.g., cell surface markers) or functional characteristics, e.g., migration properties and ability (e.g., speed of migration, persistence etc.).

A "marker" as used herein describes the characteristics and/or phenotype of a cell. Markers can be used for selection of cells comprising characteristics of interest. Markers vary with specific cells or tissues. Markers are characteristics, whether morphological, functional or biochemical (enzymatic) characteristics particular to a cell type, or molecules expressed by the cell type. Preferably, such markers are proteins, and more preferably, possess an epitope for antibodies or other binding molecules available in the art. A marker may consist of any molecule found in, or on the surface of a cell, including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate along particular lineages. A tumor cell marker can be expressed by a given tumor, or alternatively, one expressed to a greater degree of a tumor cell than a corresponding non-tumor cell. Markers can be detected by any method known or available to one of skill in the art.

The terms "tumor" or "tumor cell" are used interchangeably herein, and refers to a tissue mass or tissue type of cell that is undergoing abnormal proliferation, whether benign or malignant.

A "cancer cell" refers to a cancerous or transformed cell, either in vivo, ex vivo, and in in vitro tissue culture, that has spontaneous or induced phenotypic changes, including inappropriate cell proliferation and the ability to metastasize to other tissues or regions of the body. Transformation/cancer is associated with, e.g., morphological changes, immortalization of cells, aberrant growth control, foci formation, anchorage independence, proliferation, malignancy, loss of contact inhibition and density limitation of growth, growth factor or serum independence, tumor specific marker expression, invasiveness and tumor growth in suitable animal hosts such as nude mice, and the like, in vitro, in vivo, and ex vivo. Cancer cells can spread locally or through the bloodstream and lymphatic system to other parts of the body. Cancers within the scope of the definition comprise benign neoplasms, dysplasias, hyperplasias as well as neoplasms showing metastatic growth or any other transformations like e.g. leukoplakias which often precede a breakout of cancer.

A "sarcoma" refers to a type of cancer cell that is derived from connective tissue, e.g., bone (osteosarcoma), cartilage (chondrosarcoma), muscle (rhabdomyosarcoma or rhabdosarcoma), fat cells (liposarcoma), lymphoid tissue (lymphosarcoma), collagen-producing fibroblasts (fibrosarcoma). Sarcomas may be induced by infection with certain viruses, e.g., Kaposi's sarcoma, Rous sarcoma virus, etc.

As used herein, "metastasis" refers to the ability of cells of a cancer (e.g. a primary tumor, or a metastatic tumor) to be transmitted to other locations in the subject and to establish new tumors at such locations. An agent that "inhibits" cancer metastasis can function at any of a variety of steps in metastatic progression.

A "metastatic" cell, as used herein, refers to a cell that has a potential for metastasis and, when used in an assay as described herein, is able to migrate along the migration pathway a longer distance in a pre-determined time (i.e., at a greater speed) as compared to a non-metastatic cell. One example of a "highly metastatic" cell as used herein, (e.g., for use as a positive control cells in an assay) can be a cell that is known to have a high potential for metastasis; e.g., cells from a cell line such as, but not limited to LM2, MDA-MB-231, PC-3, DU-145, Lewis Lung carcinoma.

A "tumorigenic cell," as used herein, is a cell that, when introduced into a suitable site in a subject, can form a tumor. The cell may be non-metastatic or metastatic. A variety of types of tumorigenic and/or metastatic cells can be used in the methods as described herein (e.g., screening methods), including cells from metastatic epithelial cancers, carcinomas, melanoma, etc. The tumor cells may be, e.g., from cancers of breast, lung, colon, bladder, prostate, liver, gastrointestinal tract, endometrium, tracheal-bronchial tract, pancreas, uterus, ovary, nasopharynges, bone or bone marrow, brain, skin or other suitable tissues or organs. In a preferred embodiment, the cancer cells are of human origin.

The term "tissue" refers to a group or layer of similarly specialized cells which together perform certain special functions. The term "tissue" is also intended to include intact cells, blood, blood preparations such as plasma and serum, bones, joints, muscles, smooth muscles, and organs. The term "tissue-specific" refers to a source or defining characteristic of cells from a specific tissue.

The terms "disease" or "disorder" are used interchangeably herein, and refer to any alteration in state of the body or of some of the organs, interrupting or disturbing the performance of the functions and/or causing symptoms such as discomfort, dysfunction, distress, or even death to the person afflicted or those in contact with a person.

As used herein, the term "treating" includes preventing the progression and/or reducing or reversing at least one adverse effect or symptom of a condition, disease or disorder associated with inappropriate cell proliferation, for example cancer. The term "treating" also includes reducing or alleviating at least one adverse effect or symptom of a given condition, disease or disorder. As used herein, the term "treating" is used to refer to the reduction of a symptom and/or a biochemical marker of inappropriate cell proliferation, for example a reduction in at least one biochemical marker of cancer, by at least 10%. Thus, treatment that reduces a marker of cancer by at least 10% would be considered an effective treatment. As alternative examples, a reduction in a symptom of cancer, for example, a slowing of the rate of growth of the cancer by 10% or a cessation of the increase in tumor size, or a reduction in the size of a tumor by 10% or a reduction in the tumor spread (i.e. tumor metastasis) by 10% would also be considered effective treatments. Treatment is generally "effective" if one or more symptoms or clinical markers are reduced as that term is defined herein. Alternatively, a treatment is "effective" if the progression of a disease is reduced or halted. That is, "treatment" includes not just the improvement of symptoms or decrease of markers of the disease, but also a cessation or slowing of progress or worsening of a symptom that would be expected in absence of treatment. Beneficial or desired clinical results include, but are not limited to, alleviation of one or more symptom(s), diminishment of extent of disease, stabilized (e.g., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already diagnosed with cancer, as well as those likely to develop cancer due to genetic susceptibility or other factors such as weight, diet and health.

The term "effective amount" as used herein refers to the amount of at least one therapeutic agent effective to reduce at least one or more symptom(s) of a disease or disorder, e.g., a symptom of a cancer or malignancy. For example, the amount sufficient to reduce a symptom, e.g., caused by abnormal cell proliferation, or a cancer or malignancy by at least 10% would be considered an "effective amount". An effective amount as used herein would also include an amount sufficient to prevent or delay the development of a symptom of the disease, alter the course of a symptom disease (for example but not limited to, slow the progression of a symptom of the disease), or reverse a symptom of the disease. The phrase "therapeutically effective amount" as used herein means a sufficient amount of the composition to treat a disorder, at a reasonable benefit/risk ratio applicable to any medical treatment. The term "therapeutically effective amount" therefore refers to an amount of a composition sufficient to effect a therapeutically or prophylactically significant reduction in a symptom or clinical marker associated with a cancer, e.g., metastatic cancer, when administered to a typical subject who has a cancer, or metastatic cancer.

As used herein, the terms "administering," and "introducing" are used interchangeably, and refer to the placement of the agents as disclosed herein into a subject by a method or route which results in at least partial localization of the agents at a desired site. The agents or compositions can be administered by any appropriate route which results in an effective treatment in the subject.

The phrases "parenteral administration" and "administered parenterally" as used herein mean modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, necessary or used in formulating an active ingredient or agent for delivering to a subject. Each carrier must be "acceptable" in the sense of being compatible with the other ingredients of the formulation, and not injurious to the subject or patient.

The term "biodegradable" as used herein within the context of a substrate denotes a composition that is not biologically harmful and can be chemically degraded or decomposed by natural effectors (e.g., when implanted into a subject).

The term "isolated cell" as used herein refers to a cell that has been removed from an organism in which it was originally found or a descendant of such a cell. Optionally the cell has been cultured in vitro.

The term "isolated population" as used herein with respect to a population of cells, refers to a population of cells that has been removed and separated from a mixed or heterogeneous population of cells. In some embodiments, an isolated population is a substantially pure population of cells as compared to the heterogeneous population from which the cells were isolated or enriched. In some embodiments, an isolated population of cells is collected from the distal ⅓rd (or less than ⅓$^{rd}$) of the migration pathways of a cell migration unit after a pre-defined time period, as disclosed herein.

The term "cell culture medium" (also referred to herein as a "culture medium" or "medium") as referred to herein is a medium for culturing cells, containing nutrients and other factors that maintain cell viability and support cell proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The term "contacting" or "contact" as used herein in connection with contacting cells present on an engineered biomimetic culture platform with an agent as described herein, includes subjecting the cell, for a pre-determined time, to a culture medium which comprises that agent. The predetermined time may be prior to and/or during the migration assay procedure (i.e., during the period that the cells are migrating along the migration pathways). The term "modulate" is used consistently with its use in the art, e.g., meaning to cause or facilitate a qualitative or quantitative change, alteration, or modification in a process, pathway, or phenomenon of interest. Without limitation, such change may be an increase, decrease, or change in relative strength or activity of one or more aspects of a process, pathway, or phenomenon.

A "modulator" is an agent that causes or facilitates a qualitative or quantitative change, alteration, or modification in a process, pathway, or phenomenon of interest. A modulation will generally be by a statistically significant amount. For the avoidance of any doubt, modulation will be, e.g., at least 10% the difference relative to the absence of a modulating agent or factor.

As used herein, "proliferating" and "proliferation" refer to an increase in the number of cells in a population (growth) by means of cell division. Cell proliferation is generally understood to result from the coordinated activation of multiple signal transduction pathways in response to the environment, including growth factors and other mitogens. Cell proliferation may also be promoted by release from the actions of intra- or extracellular signals and mechanisms that block or negatively affect cell proliferation.

The term "genetically modified" as used herein refers to a cell or organism in which genetic information or material has been modified by human manipulation. Modification can be effectuated by chemical, physical, viral or stress-induced or other means, including introduction of exogenous nucleic acid through any standard means, such as transfection, such that the cell or organism has acquired a new characteristic, phenotype, genotype, and/or gene expression product, including but not limited to a gene marker, a gene product, and/or an mRNA, to endow the original cell or organism, at a genetic level, with a function, characteristic, or genetic element not present in non-genetically modified, non-selected counterpart cells or entities.

As used herein, the term "biological sample" refers to a cell or population of cells or a quantity of tissue or fluid from a subject. Most often, the sample has been removed from a subject, but the term "biological sample" can also refer to cells or tissue analyzed in vivo, i.e. without removal from the subject. In some embodiments, a "biological sample" will contain cells from a subject, but the term can also refer to non-cellular biological material, such as non-cellular fractions of blood, saliva, or urine, that can be used to measure protein phosphorylation levels. As used herein, a "biological sample" or "tissue sample" refers to a sample of tissue or fluid isolated from an individual, including but not limited to, for example, blood, plasma, serum, tumor biopsy, urine, stool, sputum, spinal fluid, pleural fluid, nipple aspirates, lymph fluid, the external sections of the skin, respiratory, intestinal, and genitourinary tracts, tears, saliva, milk, cells (including but not limited to blood cells), tumors, organs, and also samples of in vitro cell culture constituent. In some embodiments, a biological sample is from a resection, biopsy, or core needle biopsy of a primary, secondary or metastatic tumor. In addition, fine needle aspirate biological samples are also useful. In some embodiments, a biological sample is primary ascite cells. Biological samples also include explants and primary and/or transformed cell cultures derived from patient tissues. A biological sample may be provided by removing a sample of cells from subject, but can also be accomplished by using previously isolated cells (e.g., isolated by another person, at another time, and/or for another purpose). In some embodiments a biological sample is taken from a human patient, and in alternative embodiments the biological sample is taken from any mammal, such as rodents, animal models of diseases, commercial animals, companion animals, dogs, cats, sheep, cattle, and pigs, etc. The biological sample can be pretreated as necessary for storage or preservation, by dilution in an appropriate buffer solution or concentrated, if desired. Any of a number of standard aqueous buffer solutions, employing one of a variety of buffers, such as phosphate, Tris, or the like, at physiological pH can be used. The biological sample can in certain circumstances be stored for use prior to use in the assay as disclosed herein. Such storage can be at +4° C. or frozen, for example at −20° C. or −80° C., provided suitable cryopreservation agents are used to maintain cell viability once the cells are thawed.

As used herein the terms "patient", "subject" and "individual" are used interchangeably herein, and each refer to any living organism in which a cancer or a proliferative disorder can occur and where assessing the cancer for migration and/or invasiveness and/or identifying a metastatic cancer is beneficial. A subject is also any mammal where identifying a metastatic cancer is beneficial and where treatment including prophylactic treatment can be provided. The term "subject" as used herein refers to human and non-human mammals. The term includes, but is not limited to, humans, non-human animals, for example non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term does not denote a particular age or sex. Thus, adult and newborn subjects, as well as fetuses, whether male or female, are intended to be covered. The term "subject" also includes living organisms susceptible to conditions or disease states as generally disclosed, but not limited to, throughout this specification. The term "non-human animals" and "non-human mammals" are used interchangeably herein includes all vertebrates, e.g., mammals, and non-mammals such as chickens, amphibians, reptiles etc. In one embodiment, the subject is human. In another embodiment, the subject is an experimental animal or animal substitute as a disease model.

The term "drug" or "compound" as used herein refers to a chemical entity or biological product, or combination of chemical entities or biological products, administered or to be administered to a subject to treat or prevent or control a disease or condition. The chemical entity or biological product is preferably, but not necessarily a low molecular weight compound, but may also be a larger compound, for example, an oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof.

The term "agent" refers to any entity which is normally not present or not present at the levels being administered to a cell, tissue or subject. An agent can be selected from a group comprising: chemicals; small molecules; nucleic acid molecules; nucleic acid analogues; proteins; peptides; aptamers; antibodies; or functional fragments thereof. A nucleic acid sequence can be RNA or DNA, and can be single or double stranded, and can be selected from a group comprising: nucleic acid encoding a protein of interest; oligonucleotides; and nucleic acid analogues; for example peptide-nucleic acid (PNA), pseudo-complementary PNA (pc-PNA), locked nucleic acid (LNA), etc. Such nucleic acid sequences include, but are not limited to nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, including, but not limited to: mutated proteins; therapeutic proteins; truncated proteins, wherein the protein is normally absent or expressed at lower levels in the cell. Proteins can also be selected from a group comprising: mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

The term "small molecule" as used herein refers to an inorganic, organic or synthetic compound that has a low molecular weight (e.g., <900 daltons).

The term "drug screening" as used herein refers to the use of cells and tissues in the laboratory to identify drugs with a specific function. In some embodiments, the technology described herein provides drug screening methods using the engineered biomimetic culture platform to identify compounds (i.e., drugs or other agents) which modify, modulate, inhibit or reduce migration efficiency, speed or persistence, and/or the invasiveness of a cancer cell. In alternative embodiments, the technology described herein provides drug screening on cancer cells to identify compounds (e.g., agents or drugs) useful as therapies for the treatment of diseases or illnesses (e.g. human diseases or illnesses), e.g., for the treatment of metastatic cancer.

The terms "decrease", "reduced", "reduction", or "inhibit" and other grammatical variations thereof, are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference), or any decrease between 10-100% as compared to a reference level.

The terms "increased", "increase" or "enhance" or "activate" and other grammatical variations thereof, are all used herein to generally mean an increase by a statistically significant amount; for the avoidance of any doubt, "increased", "increase", "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means a two standard deviation (2SD) difference in the parameter of variable measurement. The term refers to statistical evidence that there is a difference. It is defined as the probability of making a decision to reject the null hypothesis when the null hypothesis is actually true. The decision is often made using the p-value.

The term "substantially" as used herein means for the most part, essentially the same as the character it is substantially a feature of. In some embodiments, for example, a feature which is "substantially parallel" refers to features which are at least about 80%, or at least about 90%, at least about 95%, at least about 97% or at least about 99% or more, or any integer between 80% and 100% similar to a parallel structure. In some embodiments, two features (e.g., two grooves) which are "substantially parallel" refers to two grooves that are aligned and have an angle of less than 10° between the two grooves, or an angle of less than 5° with respect to each other.

The articles "a" and "an" are used herein to refer to one or to more than one (e.g., to at least one) of the grammatical object of the article. By way of example, "an element" means one element or more than one element.

Other than in the operating examples, or where otherwise indicated, all numbers expressing quantities as used herein should be understood as modified in all instances by the term "about." The term "about" when used in connection with percentages can mean±1% or ±0.1%.

As used herein, the term "comprising" means that other elements can also be present in addition to the defined elements presented. The use of "comprising" indicates inclusion rather than limitation. Stated another way, the term "comprising" means "including principally, but not necessary solely". Furthermore, variation of the word "comprising", such as "comprise" and "comprises", have correspondingly the same meanings.

The term "consisting essentially of" means "including principally, but not necessary solely at least one", and as such, is intended to mean a "selection of one or more, and in any combination." Stated another way, other elements can be included in the description of the composition, method or respective component thereof provided the other elements are limited to those that do not materially affect the basic and novel characteristic(s) of the invention ("consisting essentially of"). This applies equally to steps within a described method as well as compositions and components therein.

The term "consisting of" as used herein as used in reference to the inventions, compositions, methods, and respective components thereof, is intended to be exclusive of any element not deemed an essential element to the component, composition or method.

It should be understood that this invention is not limited to the particular methodology, protocols, and reagents, etc., described herein and as such can vary. The terminology used herein is for the purpose of describing particular embodiments only, and is not intended to limit the scope of the technology described herein, which is defined solely by the claims.

BRIEF DESCRIPTION OF THE DRAWINGS

FIG. 1A is a schematic diagram of the nanofabrication of topographically patterned elastomeric substrate using UV-assisted capillary force lithography. PDMS was drop dispensed onto coverglass, and then the coverglass was embossed with PUA master mold (800 nm ridge, 800 nm groove, 600 nm height). Capillary force lithography molded PDMS into the nanogroove pattern. Careful removal of the PUA master completed the nanofabrication. A SEM image of the nanogrooved substrate is shown at the bottom. FIG. 1B is a schematic illustration of surface patterning using microstamp-assisted plasma lithographic techniques and ECM component coating. A microchannel-patterned PDMS stamp was fabricated using soft-lithographic techniques and molding into PDMS (step 1). The cell culture platform was prepared for plasma lithographic patterning on the substrate (step 2). Oxygen plasma treatment, shown as a grey exposed surface, of the device modified the originally hydrophobic nanogroove-patterned PDMS to a hydrophilic surface, excluding the area in contact with the PDMS stamp (step 3). Collagen type I at 50 μg/mL was coated on the nanogroove-patterned PDMS for 6 hours to produce cell adherent regions and cell non-adherent regions, where the cell non-adherent regions are regions of the nanogrooved substrate in contact with the ridges of the PDMS stamp (step 4). The PDMS stamp was carefully removed after loaded cells reached monolayer. The removal of PDMS stamp resulted in a biomimetic culture platform, and in the embodiment shown, having various widths of ECM-coated micropatterns (i.e., cell adherent regions) between cell non-adhrent regions (i.e., collagen or ECM-untreated areas) (step 5). FIG. 1C shows representative fluorescent images of the 30, 60, 80, and 120 μm width patterns of Collagen type I (50 μg/mL) conjugated with Alexa Fluor 488-FITC (40 μg/mL). Only plasma-treated surface of the nanogrooved substrate was uniformly coated with the Collagen type I solution even the inner parts of the grooves. FIG. 1D shows microscopic images of patterned MCF-10A cells on nanogroove-patterned elastomeric substrates. After the removal of the PDMS stamp, the images were captured from the time point when the cells clearly entered 150 μm into the micropatterns for 12 hrs.

FIGS. 2A and 2B show MCF10A wild type cell, and FIGS. 2C and 2D show mutant PIK3CA knockin cell plated on the biomimetic culture platform after ECM-surface coating with type I collagen (50 g/ml) to form migration pathways on flat (2A, 2C) and nanogrooved PDMS substrates (2B, 2D). Scale bars=100 μm. The insert image in FIG. 2B shows the direction of nanogrooves are aligned with the direction of the migration pathways. FIGS. 2A-2D show two images of the migration pathways taken at 0 hr and 18 hrs respectively, superimposed into a single image. Dashed lines indicate the initial front edges of cells at 0 hrs and dot lines indicates the terminal front edges of migrated cells in the migration pathway at 18 hours. Arrows indicate a total migration distance over 18 hrs. FIG. 2E shows the paths of individual migrating MCF-10A cells in a migration pathway with a flat surface, and FIG. 2F shows individual MCF-10A cells in a migration pathway with a nanogrooved PDMS substrate, which were analyzed using custom MATLAB code. Color bar legends indicate the migration speed of cells at each time-lapse in units of μm/hr. FIG. 2G shows individual migration paths of MCF-10A cells, defined as the angular deviation from the direction of nanotopography on flat surface, as a measure of migratory contact guidance. FIG. 2H shows individual migration paths of MCF-10A cells, defined as the angular deviation from the direction of nanotopography on nanogrooved substrates to assess migratory contact guidance. The portion of migration direction within ±15 degree from the nanogrooves representing straight directionality is highlighted in each graph. FIG. 2I shows the migration speed, and FIG. 2J shows the persistence time of the migratory responses of MCF-10A wild type and oncogenic PIK3CA knockin cells to substrate topography analyzed by fitting the mean-squared displacement of the cell path data to the persistent random walk model. Error bars represent standard deviations of three technical replicates with 80-100 cells per each experiment (*p<0.01).

FIG. 3A shows microscopic images of mutant PIK3CA knockin cells migration on Collagen Type I patterned nanogrooved PDMS substrates. Time-lapse video microscopy was used to capture the cellular motility and digital images were taken every 20 min for a total of 12 hrs per experiment (data not shown). Scale bars=100 μm. Dotted lines indicate the representative front cell edges taken at 0 hr and 9 hrs respectively for each of the migration pathways of width 120 μm, 80 μm, 60 μm and 30 μm, showing representative total migration distance over 9 hrs. FIG. 3B shows the migration distance of individual migrating PIK3CA knockin cells on flat or nanogrooved migration pathways on PDMS substrates, over a 9 hour period as analyzed using custom MATLAB code. Gray-scale bar legend indicates migration speed of cells at each time-lapse in units of μm/hr. FIG. 3C shows the migration direction of individual paths of PIK3CA knockin cells on both flat or nanogrooved migration pathways, and shows the portion of the cells that have migration directions within ±15 degree from the direction of long-axis of the ECM-coated migration pathway, thereby showing straight directionality of the migration of each cell. As the width of the migration pathways became narrower from 120 μm to 30 μm, motile cells show greater straight directionality on both flat and nanopatterned substrates with a decreased effect of nanotopography on migratory contact guidance.

FIG. 4A is a schematic drawing showing an example of single particle (representing cells) undergoing a random walk in a geometrically constrained environment (i.e., the migration pathway) that results in increased motility coefficients, and thus mean displacements, in the x direction for a population of cells. Cells behind a collective migration front and lateral cell interactions further constrain the system. FIG. 4B is a schematic drawing showing a model output of normalized migration distance in the x direction over of a range of displacement steps with defined persistence length for a range of channel/pattern widths. Model output is from 100,000 steps/particle averaged over 1000 particles and data are normalized to random walk behavior in the unconstrained 2D configuration. FIG. 4C shows normalized migration distance for four pattern widths highlighting the increase in migration along the x-direction as the geometric constraint narrows. Data are from the average of 10 runs with 300 particles undergoing 100,000 steps/particle.

FIG. 5A shows cell migration speed (μm/hr) of MCF-10A wild type cells in different migration pathway widths on nanogrooved or flat substrate nanotopography. FIG. 5B shows cell migration speed (μm/hr) of oncogenic PIK3CA knockin cells in different migration pathway widths on nanogrooved or flat substrate nanotopography. FIG. 5C shows cell migration speed (μm/hr) of MCF-10A wild type cells or oncogenic PIK3CA knockin cells in different migration pathway widths on a flat surface substrate. FIG. 5D shows cell migration speed (μm/hr) of MCF-10A wild type cells or oncogenic PIK3CA knockin cells in different migration pathway widths on a nanogrooved substrate. FIG. 5E shows persistence time (min) of MCF-10A wild type cells in different migration pathway widths on nanogrooved or flat substrate nanotopography. FIG. 5F shows cell persistence time (min) of oncogenic PIK3CA knockin cells in different migration pathway widths on nanogrooved or flat substrate nanotopography. Persistence time of MCF-10A cells (FIG. 5E) and oncogenic PIK3CA knockin cells (FIG. 5F) were calculated by fitting the mean-squared displacement of cell path data to the persistent random walk model. Error bars represent standard deviations of three technical replicates with 40-50 cells per each experiment and statistical significance is indicated by P values (*p<0.01).

FIGS. 6A-6B is a SEM image showing interaction of an aortic endothelial cell with the basement membranes in an intact vessel. FIG. 6A is prior-art and shows the remodeling of ECM structures by motile HT1080 fibrosarcoma cells. The edges of the cell membrane (arrowheads) are interacting with the rough ECM structures forming the basement membrane (asterisks). The arrow marks within the boxed area highlights the specific interaction between an end foot of the cell membrane and the nanotopography of the ECM. Transition from individual to collective invasion is displayed in 3D spheroids cultured within a 3D collagen lattice. Single cells (white arrowheads) generate small proteolytic tracks (black arrowheads in inset; detected by cleavage site-specific COL2 3/4C antibody) that become further remodeled and widened by solid strands of multiple cells (Str). (Images of FIG. 6A are taken from Friedl and Wolf, 2008, Cancer Res, 68(15): 7247-9 entitled "Tube travel: the role of proteases in individual and collective cancer cell invasion"). FIG. 6B is a prior art image which shows carcinoma cells in primary mammary tumors moving along ECM fibers. Multiphoton microscopy shows that carcinoma cells move on extracellular matrix (ECM) fibers and do not seem contrained by the ECM networks. The left panel of FIG. 6B shows a high-magnification image of carcinoma cells in the tumor mass contacting collagen containing fibers, and the right panel is a schematic of the microscopy image shown in the left panel. Arrowheads point to cell-matrix interactions. Scale bar=25 µm. (Images of 6B are taken from FIG. 2B of Condeelis and Segall, 2003, Nature Reviews, 3: 921-929, entitled "Intravital imaging of cell movement in tumours"). FIG. 6C is prior art, showing in the left panel an MRI image of a brain tumor (bright mass) and shows individual cells migrating along the corpus callosum (arrow) and show nanotopographic cues induce polarity and directional migration of carcinoma cells. FIG. 6C, right panel shows individual brain cancer cells (arrow) migrate along myelinated fibers of white matter tracts. (FIG. 6C is prior-art and adapted from FIG. 2 of Bellail et al. (2004; Int. J. Cell Biol., 36(6):1046-69, entitled "Microregional extracellular matrix heterogenocity in brain modulates glioma cell invasion").

FIGS. 8A-8D is a schematic of an exemplary cell migration unit. FIG. 8A shows an exemplary simple and repeatable cell migration unit, which shows the migration pathway (i.e., cell permissive region) as strip patterned adjacent to a cell non-adherent region, and a cell loading region present at the proximal end of the migration pathway, allowing cells plated or seeded in the cell loading region to migrate along the longitudinal axis of the migration pathway towards the distal and not substantially enter the cell non-adherent region. A cell migration unit can have multiple migration pathways (i.e. cell permissive regions), and multiple cell non-adhesive regions. FIG. 8B shows exemplary cell migration units which comprises n number of migration pathways, and n number of cell non-adherent regions (i.e., a 1:1 ratio of migration pathways to non-adherent regions), therefore allowing each migration pathway to be adjacent (or parallel to) at least one cell non-adherent region. FIG. 8B shows one embodiment of a cell migration unit where n=3, showing an exemplary configuration of a cell migration unit comprising 3 migration pathways and 3 cell non-adherent regions. An exemplary cell migration unit can have the migration pathways arranged in series (e.g., see top left of FIG. 8B) or they can be arranged as a mirror image (e.g., see bottom left of FIG. 8B), where the cell migration unit has a centrally located cell loading region, and extending perpendicular from cell loading region are n number of migration pathways, interdispersed between n number of cell non-adherent regions. Also shown in FIG. 8B is a cell migration unit where n=6, showing an exemplary configuration of a cell migration unit comprising 6 migration pathways and 6 cell non-adherent regions, where there is a centrally located cell loading region. Each cell migration unit can be arranged in an array, e.g., see right of FIG. 8B, which shows an array of 4 cell migration units with n=3, or an array of 2 cell migration units where n=6. FIG. 8C shows another embodiment of cell migration unit, which comprises n number of migration pathways, and n+1 number of cell non-adherent regions, therefore enabling each migration pathway to be sandwiched between cell non-adherent regions. FIG. 8C shows a cell migration unit where n=3, showing an exemplary configuration of a cell migration unit comprising 3 migration pathways and 4 cell non-adherent regions. Each cell migration unit can be arranged in an array, e.g., see right of FIG. 8C, which shows an array of 4 cell migration units of this configuration. FIG. 8D shows another exemplary embodiment of a cell migration unit, which comprises n number of migration pathways, and n+2 number of cell non-adherent regions, thereby allowing a mirror image of the migration pathways. More specifically, in such an exemplary configuration of a cell migration unit, there is a centrally located cell loading region and extending perpendicular from cell loading region are n number of migration pathways, interdispersed between n+2 cell non-adherent regions, where each migration pathway is sandwiched between a cell non-adherent region. FIG. 8D shows a cell migration unit where n=6, showing an exemplary configuration of a cell migration unit comprising 6 migration pathways and 8 cell non-adherent regions. Such a cell migration unit can be arranged in an array, e.g., see right of FIG. 8D, which shows an array of 2 cell migration units of this configuration. P=proximal end, D=distal end.

FIGS. 11A-11C show an exemplary high-throughput screening using the biomimetic culture platform. FIG. 11A shows a multi-well plate, each well comprising a cell migration unit, and specific wells are treated with a drug and the influence on the cells migration properties is assessed after a pre-determined time. Such a HTS can be used to screen agents for biomaterial development, cancer drug screening, stem cell culture, cancer stem cell identification and collection, and disease diagnostic and prognosis (i.e., identifying if a cancer sample comprises cells with a high migration potential and therefore identifies a metastatic cancer, and/or aggressive cancer and a poor prognosis). FIG. 11B shows a microscope image of the surface of an exemplary surface of a well or coverslip present in a multi-well plate, with an array of 3 migration units on. FIG. 11C is a higher magnification image from FIG. 11B, and shows an example of the details of the nanopatterning on the surface of the microwell plate.

DETAILED DESCRIPTION

As disclosed herein, the inventors have engineered a biomimetic culture platform that comprises both nanotopographic surface features and defined micropatterning of cell adherent regions (referred to as "migration pathways"), to allow synergistic action of the contact guidance cues provided by nanotopographic surface features, and directional or trajectory guidance cues provided by the cell adherent regions. The engineered biomimetic culture platform disclosed herein mimics the normal extracellular matrix (ECM) and recapitulates the in vivo tumor environment in that it reproduces the developmental transition of tumor cells that occurs in vivo in a tumor environment and can force the tumor cells to go through an epithelial to mesenchymal transition (EMT).

Accordingly, an engineered biomimetic culture platform is useful, e.g., as a rapid and simple platform for HTS of migration behavior of tumor cells in a system that recapitulates the in vivo tumor extracellular matrix environment. For example, in some embodiments, the engineered biomimetic culture platform disclosed herein can be used for assessing migration of tumor cells, as well as identifying metastatic cells, or tumors with a high proportion of cells likely to become metastatic, as well as used in screening assays to identify agents which inhibit tumor cell migration and/or EMT.

As disclosed herein, the technology described herein relates to an engineered biomimetic culture platform comprising a nanotextured substrate comprising a polymer substrate which has a nanotextured array of parallel grooves and ridges (referred to herein as nanopattern or nanogrooved topology). On the surface of the nanotextured array of parallel grooves and ridges are defined cell permissive (or cell adherent) regions, referred to herein as migration pathways, that comprise an extracellular matrix (ECM) coating. These defined regions are in a micropattern and serve as geometric conduits directing the migratory trajectory of the cells. Thus, the engineered biomimetic culture platform described herein is unique in that it combines the synergistic action of nanoscale cues (provided by the nanopattern) for contact guidance of migrating cells, with microscale cues provided by the migration pathways to direct anisotropic diffusion behavior of the migrating cells, thereby providing a culture platform mimicking the in vivo extracellular matrix.

Figure 8C:
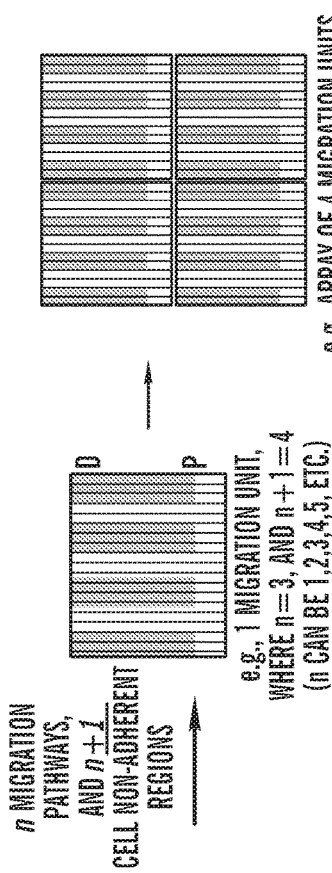

One aspect of the technology described herein relates to a composition comprising an engineered biomimetic culture platform, which comprises a nanopatterned surface and comprises, on the nanopatterned surface, an array of at least one repeatable micropattern unit, referred to as a cell migration unit, where the cell migration unit comprises (i) at least one cell permissive region, referred to as a migration pathway (serving as a microscale geometric conduit) directing anisotropic diffusion behavior of the cells, (ii) at least one cell non-adherent region adjacent to the migration pathway that defines the boundaries of the cell permissive region, and (iii) at least one cell loading region at the proximal end of the migration pathway (and optionally at the proximal end of the hydrophobic region). An exemplary cell migration unit is shown in FIG. 8A, with various embodiments shown in FIGS. 8B-8D, and FIG. 9. In some embodiments, multiple migration pathways (i.e. cell permissive regions) and cell non-adherent regions can be present on a substrate, such that multiple cell migration units are present on a single nanopatterned platform, thereby forming an array of cell migration units. Such an array can be used, for example, in methods to assess different cancer or tumor types for migration potential, as well as assessing or screening for molecules that inhibit the migration potential of a specific cell type, e.g., cancer or tumor cell type and the like.

I. Engineered Biomimetic Culture Platform (BCP)

As disclosed herein, the platform comprising both nanotextured surface and micropatterning of cell adherent regions, herein referred to as an engineered biomimetic culture platform (BCP), has a nanotextured array of parallel grooves and ridges, and on the surface of the nanotextured array of parallel grooves and ridges are defined cell permissive/cell adherent regions, referred to herein as migration pathways, that comprise an extracellular matrix (ECM) component coating. These defined cell permissive regions serve as geometric conduits to direct the migratory trajectory and anisotropic diffusion behavior of the migrating cells.

In some embodiments, the engineered biomimetic culture platform comprises a nanopatterned surface and comprises, on the nanopatterned surface, an array of at least one repeatable micropattern unit, referred to as a cell migration unit. Each cell migration unit comprises (i) at least one cell permissive region, also referred to as a migration pathway (serving as a microscale geometric conduit), and at least one cell non-adherent region adjacent to the migration pathway, and at least one cell loading region at the proximal end of the migration pathway (an optionally at the proximal end of the hydrophobic region). In some embodiments, a single cell migration unit can comprise multiple migration pathways (i.e. cell permissive regions) and multiple cell non-adherent regions, and multiple cell migration units can be present on a single nanopatterned platform, thereby forming an array of cell migration units. Such an array is useful in methods to assess different cancer or tumor types for migration potential, as well as assessing or screening for molecules that inhibit the migration potential of a specific cell type, e.g., cancer or tumor cell type and the like.

One advantage of the integration of the nanopatterning and micropatterning on a single platform is that they unexpectedly function synergistically to provide both contact directional cues for anisotropic alignment of the cells in a particular direction, and guidance conduits to direct migration trajectory, thereby mimicking the in vivo migration cues in an in vitro, and highly scalable platform.

As discussed above, the engineered biomimetic culture platform as described herein involves a nanotextured substrate treated to define microscale cell permissive migration pathways between cell non-permissive (or cell non-adherent) regions. The various considerations regarding substrate materials and treatments, dimensions of nanotexture and microscale pathways and how to make and use the engineered biomimetic culture platform are discussed in the following sections (i)-(iv).

(i) Substrate Materials:

One aspect of the biomimetic culture platform is the rigidity of the substrate and the ability to modulate it. The biomimetic culture platform polymer substrate as disclosed herein allows for independent alteration of substrate rigidity in addition to the tunability of the substrate topography. The biomimetic culture platform substrate rigidity can be altered in several ways, for example, through variation of polymer concentration, crosslinker concentration, and polymer composition/type. For example, the concentration of the polymer can be varied (such as weight percent in an aqueous or solvated solution), and these varying concentrations of polymer can be nanofabricated to incorporate the same topographical pattern cues, but will also have varying rigidities. This permits the biomimetic culture platform to be used to separately characterize the effects of substrate rigidity on cell function. Rigidity tuning allows modeling of differing states, such as healthy tissue, scar tissue or tumor, which have variable stiffness and can profoundly impact cell function.

In some embodiments, the substrate of the biomimetic culture platform comprises a polymer hydrogel comprising, within the matrix of said polymer substrate, a biocompatible extracellular matrix protein, a synthetic or engineered matrix polypeptide, or other engineered polypeptide(s).

In some embodiments, the biomimetic culture platform can be nanofabricated from scalable biocompatible polymers, including, but not limited to polyethylene glycol (PEG), polyethylene glycol-gelatin methacrylate (PEG-GelMA) and chemical variants thereof and hydrogel arrays. Others include, but are not limited to poly(urethane acrylate)

(PUA), poly(lactic-co-glycolic) acid (PLGA) or poly(methyl methyl methacrylate (PMMA).

In some embodiments, the substrate of the biomimetic culture platform comprises at least one of polyglycolic acid (PGA), polylactic acid (PLA), polyanhydride, polycapralactone (PCL), polydioxanone and polyorthoester. One of the most common polymers used as a biomaterial is the polyester copolymer poly(lactic acid-glycolic acid) (PLGA). PLGA is highly biocompatible, degrades into biocompatible monomers (e.g., if implanted) and has a wide range of mechanical properties making this copolymer and its homopolymers, PLA and PGA, useful as a substrate for cell deposition. The substrate can be porous or non-porous.

In one embodiment, the substrate of the biomimetic culture platform is biocompatible, and biodegrades or autocatalytically degrades in vivo into biocompatible byproducts. Not to be bound by theory, but prevailing mechanism for polymer degradation is chemical hydrolysis of the hydrolytically unstable backbone of the PLGA polymers. Polymers of varying copolymer ratios including PLA, PLGA75:25, and PLGA50:50 have different degradation rates, with PLGA50:50 degrading the quickest, followed by PLGA 75:25 then PLA. Therefore, with increasing percentage of PGA and concurrent decrease in percentage of PLA in a co-polymer of PLGA increases the rate of degradation compared to PLA alone, and thus the rate of degradation can be tailored to the desired use. Any ration of PLA:PGA copolymer is encompassed for use in the technology described herein.

In some embodiments, other materials can be selected to be used as the substrate material or a component of the substrate material; which can be selected from the group consisting of hydroxyapatite (HAP), tricalcium phosphate (TCP), tetracalcium phosphate (TTCP), dicalcium phosphate anhydrous (DCPA), dicalcium phosphate dihydrate (DCPD), octacalcium phosphate (OCP), calcium pyrophosphate (CPP), collagen, gelatin, hyaluronic acid and chitin. In alternative embodiments, the substrate can also comprise additional material, for example, but are not limited to calcium alginate, agarose, hyaluronate derivatives or other materials (Perka C. et al. (2000) J. Biomed. Mater. Res. 49:305-311; Sechriest V F. et al. (2000) J. Biomed. Mater. Res. 49:534-541; Chu C R et al. (1995) J. Biomed. Mater. Res. 29:1147-1154; Hendrickson D A et al. (1994) Orthop. Res. 12:485-497).

In some embodiments, the substrate of the biomimetic culture platform comprises a polymer substrate which is optically transparent. In some embodiments, the substrate of the biomimetic culture platform can comprise a UV curable hydrogel polymer, a thermosensitive hydrogel polymer or a polymer produced by solvent evaporation. In some embodiments, the substrate of the biomimetic culture platform is composed of a biocompatible hydrogel compatible with capillary force lithography.

In some embodiments, the substrate of the biomimetic culture platform can be configured using a polymer construction which mimics the rigidity of the tissue, e.g., a normal tissue, tumor or other tissue of interest, e.g., breast tissue or epithelial tissue. In some embodiments, the biomimetic culture platform can be configured using a polymer construction which has a rigidity varying between 30 kPa to 200 kPa. In some embodiments, the biomimetic culture platform comprises a polymer substrate that has a rigidity in the range of 5 to 200 kPa, for example, a rigidity of at least about 5 kPa, or at least about 10 kPa, or at least about 20 kPa, or at least about 30 kPa, or at least about 40 kPa, or at least about 50 kPa, or at least about 60 kPa, or at least about 70 kPa, or at least about 80 kPa, or at least about 90 kPa, or at least about 100 kPa, or at least about 120 kPa, or at least about 140 kPa, or at least about 160 kPa, or at least about 180 kPa, or at least about 200 kPa or more than 200 kPa, or any integer between 5-200 kPa.

In some embodiments, the substrate of the biomimetic culture platform can comprise within or upon the substrate, additional components selected from the group including extracellular matrix proteins, growth factors, lipids, fatty acids, steroids, sugars and other biologically active carbohydrates, biologically derived homopolymers, nucleic acids, hormones, enzymes, pharmaceuticals, cell surface ligands and receptors, cytoskeletal filaments, motor proteins, and combinations thereof. Alternatively or in addition, the structure can comprise at least one conducting polymer selected from poly(pyrrole)s, poly(acetylene)s, poly(thiophene)s, poly(aniline)s, poly(fluorene)s, Poly(3-hexylthiophene), polynaphthalenes, poly(p-phenylene sulfide), poly(N-Isopropylacrylamide) (PIPAAm), and poly(para-phenylene vinylene)s. In some cases, the polymer structure comprises an integral pattern of the polymer and molecular remnant traces of poly(N-Isopropylacrylamide).

In some embodiments, the polymer structure is composed of, or comprises at least one biological hydrogel selected from fibrin, collagen, gelatin, elastin and other protein and/or carbohydrate derived gels or synthetic hydrogel selected from polyethylene glycol, polyvinyl alcohol, polyacrylamide, poly(N-isopropylacrylamide), poly(hydroxyethyl methacrylate) and other synthetic hydrogels, and combinations thereof.

In some embodiments, the substrate of the biomimetic culture platform for use in the compositions and methods as disclosed herein, can be spatially organized from the nanometer to centimeter length scales and can be generated via methods described herein. The polymers, including, for example, biopolymer (e.g., protein, carbohydrate, glycoprotein etc.,) can be deposited onto a transitional polymer surface using patterning techniques that allow for micrometer scale patterning of the deposited polymers. These nanopatterning and micropatterning techniques include but are not limited to one or a combination of capillary force lithography, soft-lithography, self-assembly, vapor deposition and photolithography. As disclosed in the Examples and FIGS. 1A and 1B, the nanopatterning can be fabricated using UV-assisted capillary force lithography and the micropatterning can be deposited by a combination of microstamp-assisted soft-lithography and plasma lithography. Once on the surface, inter-polymer interactions attract the polymers together such that they become bound together. These interactions may be hydrophilic, hydrophobic, ionic, covalent, Van der Waals, hydrogen bonding or physical entanglement, depending on the specific polymers involved. In the appropriate solvent, dissolution or a change in the surface energy of the transitional polymer releases the patterned polymer structure from the surface into solution as an integral, free-standing structure.

Further, in some embodiments, the substrate can be transparent, so as to facilitate observation of the cells cultured on the BCP. Optical transparency can be achieved for many substrate materials by making the structure sufficiently thin as to permit light to transmit.

In some embodiments, the substrate of the biomimetic culture platform is bioresorbable and/or biodegradable. Further, in some embodiments the substrate is biocompatible and bioreplaceable.

In some embodiments, a substrate of the biomimetic culture platform useful in the methods as disclosed herein is a decellularized tissue sheet, such as a decellularized pericardial tissue which is disclosed in U.S. Patent Application 2008/0195229 and International Patent Application WO/2003/050266 which are incorporated herein in their entirety by reference, or other sheet such as a perfusion-decellularized matrix as disclosed in Ott et al., 2008, Nature Medicine 14, 213-221 which is incorporated herein by reference.

In one embodiment, a bioreplaceable material for use as a substrate of the biomimetic culture platform in the methods and compositions as disclosed herein is derived from submucosal tissue. In some embodiments, the submucosal tissue can be in a fluidized form. Submucosal tissue can be fluidized by comminuting the tissue and optionally subjecting it to enzymatic digestion to form a substantially homogenous solution. The preparation of fluidized forms of submucosa tissue is described in U.S. Pat. No. 5,275,826, the disclosure of which is expressly incorporated herein in its entirety by reference.

In one embodiment, the submucosa tissue suitable for inclusion in, or on a substrate comprises natural collagenous matrices that include highly conserved collagens, matrix proteins, glycoproteins, proteoglycans, and glycosaminoglycans in their natural configuration and natural concentrations, and other factors. Submucosal tissue of this kind is commercially available, such as SURGISIS® (SIS) which is available from Cook Biotech Incorporated (Bloomington, Ind.).

The preparation of SIS from a segment of small intestine is disclosed in U.S. Pat. No. 4,902,508 which is incorporated herein by reference. A segment of intestine is first subjected to abrasion using a longitudinal wiping motion to remove both the outer layers (particularly the tunica serosa and the tunica muscularis) and the inner layers (the luminal portions of the tunica mucosa). Typically the SIS is rinsed with saline and optionally stored in a hydrated or dehydrated state until use. Details of the characteristics and properties of intestinal submucosa (SIS) which one can use in the methods and compositions as disclosed herein are described in U.S. Pat. Nos. 4,352,463, 4,902,508, 4,956,178, 5,281,422, 5,372,821, 5,445,833, 5,516,533, 5,573,784, 5,641,518, 5,645,860, 5,668,288, 5,695,998, 5,711,969, 5,730,933, 5,733,868, 5,753,267, 5,755,791, 5,762,966, 5,788,625, 5,866,414, 5,885,619, 5,922,028, 6,056,777 and WO-97/37613, which are incorporated herein in their entirety by reference.

In some embodiments, the substrate of the biomimetic culture platform useful in the compositions and the methods described herein can be sterilized using conventional disinfection/sterilization techniques including glutaraldehyde tanning, formaldehyde tanning at acidic pH, propylene oxide treatment, ethylene oxide treatment, gas plasma sterilization, gamma irradiation or electron beam treatment, and peracetic acid (PAA) disinfection. Sterilization techniques which do not adversely affect the mechanical strength, structure, and biotropic properties of the polymer substrate are preferred. For instance, strong gamma irradiation can cause loss of strength of the sheets of polymer substrates. Preferred sterilization techniques include exposing the polymer substrate to peracetic acid, 1-4 Mrads gamma irradiation (more preferably 1-2.5 Mrads of gamma irradiation) or gas plasma sterilization. Typically, a polymer substrate can be subjected to two or more sterilization processes. After the polymer substrate is treated in an initial disinfection step, for example by treatment with peracetic acid, the polymer substrate can be wrapped in a plastic or foil wrap and sterilized again using electron beam or gamma irradiation sterilization techniques.

(ii) Nanotexture on the Surface of the Biomimetic Culture Platform:

As described herein, the engineered biomimetic culture platform comprises a nanotextured array of substantially parallel grooves and ridges that provide direct contact migratory cues to promote or allow the cells to move in a directed fashion. In particular, the engineered biomimetic culture platform is nanotextured with four independently tunable parameters: ridge width, groove width, ridge height and periodicity. These parameters can be easily tuned, for example, by the use of differing masters in capillary force lithography, and these masters can be custom generated through conventional nanofabrication techniques such as electron-beam lithography. By being able to vary these dimensions independently, migration, as well as cell function, morphology and alignment can be altered. This precise level of topographical tuning allows one to both faithfully recreate the topographical cues of the ECM, as well as alter a cell monolayer model as needed.

Unless otherwise indicated, the nanotexture of the substrate described herein will include a regular pattern of the specified texture. One substrate can be all the same nanotexture or alternatively, can include defined regions with differing nanotexture dimensions. In the following, nanotexture patterning groove width, groove depth and ridge width dimensions are set out. It should be understood that for particular applications, any combination of groove width, groove depth (or ridge height) and ridge width values and/or ranges described herein can be made and used in a repeated pattern, e.g., to mimic the ECM topology if a given tissue microenvironment.

A) Groove Width of the Nanotexture

In some embodiments, the nanopatterning of ridges and grooves of the engineered biomimetic culture platform has grooves with a width of between 1-3000 nm (i.e., >1 nm and less than 3000 nm). In some embodiments, an engineered biomimetic culture platform has grooves with a width of no greater than 10 nm, no greater than 20 nm, no greater than 50 nm, no greater than 100 nm, no greater than 200 nm, no greater than 300 nm, no greater than 400 nm, no greater than 500 nm, no greater than 600 nm, no greater than 700 nm, no greater than 800 nm, no greater than 900 nm, no greater than 1000 nm, no greater than 1200 nm, no greater than 1400 nm, no greater than 1600 nm, no greater than 1800 nm, no greater than 2000 nm, no greater than 2200 nm, no greater than 2400 nm, no greater than 2600 nm, no greater than 2800 nm or no greater than 2999 nm.

In some embodiments, the width of the groove is equal to, or between the ranges of 50 nm-2000 nm, or between about 200 nm-1000 nm, or at least about 50 nm, or at least about 75 nm, or at least about 100 nm, or at least about 150 nm, or at least about 200 nm, or at least about 250 nm or at least about 500 nm, or at least about 1000 nm, or at least about 2000 nm. In some embodiments, the width is equal to, or between about 300 nm-500 nm, or equal to, or between about 500 nm-800 nm, or equal to, or between about 600 nm-900 nm, or equal to, or between about 700-1000 nm, or equal to, or between 1000-1200 nm or no greater than 1200 nm or 1500 nm. In some embodiments, a range for the groove width is between about 200 nm-1000 nm, or between 1000 nm and 2000 nm, or between 1000 and 3000 nm.

In some embodiments, the width of the groove is equal to, or between the ranges of 10-100 nm, for example no greater than about 10 nm, or no greater than about 20 nm, or no greater than about 30 nm, or no greater than about 40 nm, or no greater than about 50 nm, or no greater than about 60 nm, or no greater than about 70 nm, or no greater than about 80 nm, or no greater than about 90 nm, or no greater than about 100 nm or more than 100 nm in width. In some embodiments, the width of the groove is between 5 nm-1000 nm, for example no greater than about 5 nm, no greater than about 10 nm, no greater than about 20 nm, no greater than about 30 nm, no greater than about 40 nm, no greater than about 50 nm, no greater than about 60 nm, no greater than about 70 nm, or no greater than about 80 nm, or no greater than about 90 nm, no greater than about 100 nm, no greater than about 200 nm, no greater than about 300 nm, no greater than about 400 nm, or no greater than about 500 nm, or no greater than about 600 nm, or no greater than about 700 nm, or no greater than about 800 nm, or no greater than about 900 nm, or no greater than about 1000 nm, or no greater than about 1200 nm, or no greater than about 1400 nm, or no greater than about 1500 nm, or no greater than about 16000 nm, or no greater than about 1800 nm, or no greater than about 2000 nm in width. In some embodiments, the width of the groove is equal to, or between the ranges of about 200-800 nm, or equal to, or between about 100-200 nm, or r equal to or between about 200-400 nm, or equal to or between about 400-600 nm, or equal to or between about 600-800 nm, or equal to or between about 800-1000 nm, or equal to or between 1000 nm-2000 nm, or between 1000 nm-3000 nm.

B) Ridge Width of the Nanotexture

In some embodiments, the nanopatterning of ridges and grooves of the engineered biomimetic culture platform has ridges with a width of between 1-3000 nm, (i.e., >1 nm and less than 3000 nm). In some embodiments, an engineered biomimetic culture platform has ridges with a width of no greater than 10 nm, no greater than 20 nm, no greater than 50 nm, no greater than 100 nm, no greater than 200 nm, no greater than 300 nm, no greater than 400 nm, no greater than 500 nm, no greater than 600 nm, no greater than 700 nm, no greater than 800 nm, no greater than 900 nm, no greater than 1000 nm, no greater than 1200 nm, no greater than 1400 nm, no greater than 1600 nm, no greater than 1800 nm, no greater than 2000 nm, no greater than 2200 nm, no greater than 2400 nm, no greater than 2600 nm, no greater than 2800 nm, no greater than 2999 nm.

In some embodiments, the width of the ridge is equal to, or between 50 nm-2000 nm, or equal to, or between about 200 nm-1000 nm, or at least about 50 nm, or at least about 75 nm, or at least about 100 nm, or at least about 150 nm, or at least about 200 nm, or at least about 250 nm or at least about 500 nm, or at least about 1000 nm, or at least about 2000 nm. In some embodiments, the width is equal to, or between about 300 nm-500 nm, or equal to, or between about 500 nm-800 nm, or equal to, or between 600 nm-900 nm, or equal to, or between 700-1000 nm, or equal to, or between 1000-1200 nm or no greater than 1200 nm or 1500 nm. In some embodiments, a range for the ridge width for is equal to, or between about 200 nm-1000 nm, or equal to or between 1000 nm-2000 nm, or between 1000-3000 nm.

In some embodiments, the width of the ridge is equal to, or between 10-100 nm, for example no greater than about 10 nm, or no greater than about 20 nm, or no greater than about 30 nm, or no greater than about 40 nm, or no greater than about 50 nm, or no greater than about 60 nm, or no greater than about 70 nm, or no greater than about 80 nm, or no greater than about 90 nm, or no greater than about 100 nm or more than 100 nm in width. In some embodiments, the width of the ridge is equal to, or between 5 nm-1000 nm, for example no greater than about 5 nm, no greater than about 10 nm, no greater than about 20 nm, no greater than about 30 nm, no greater than about 40 nm, no greater than about 50 nm, no greater than about 60 nm, no greater than about 70 nm, or no greater than about 80 nm, or no greater than about 90 nm, no greater than about 100 nm, no greater than about 200 nm, no greater than about 300 nm, no greater than about 400 nm, or no greater than about 500 nm, or no greater than about 600 nm, or no greater than about 700 nm, or no greater than about 800 nm, or no greater than about 900 nm, or no greater than about 1000 nm, or no greater than about 1200 nm, or no greater than about 1400 nm, or no greater than about 1500 nm, or no greater than about 16000 nm, or no greater than about 1800 nm, or no greater than about 2000 nm in width. In some embodiments, the width of the ridge or equal to, or between about 200-800 nm, or equal to, or between about 100-200 nm, or equal to, or between about 200-400 nm, or equal to, or between about 400-600 nm, or equal to, or between about 600-800 nm, or equal to, or between about 800-1000 nm, or equal to, or between 1000 nm-2000 nm, or between 1000 nm-3000 nm.

C) Groove Depth of the Nanotexture

In some embodiments, the nanopatterning of ridges and grooves of the engineered biomimetic culture platform has a groove depth (or ridge height) of between 1-3000 nm (i.e., >1 nm and less than 3000 nm). In some embodiments, an engineered biomimetic culture platform has a groove depth of, for example, no greater than 10 nm, no greater than 20 nm, no greater than 50 nm, no greater than 100 nm, no greater than 200 nm, no greater than 300 nm, no greater than 400 nm, no greater than 500 nm, no greater than 600 nm, no greater than 700 nm, no greater than 800 nm, no greater than 900 nm, no greater than 1000 nm, no greater than 1200 nm, no greater than 1400 nm, no greater than 1600 nm, no greater than 1800 nm, no greater than 2000 nm, no greater than 2200 nm, no greater than 2400 nm, no greater than 2600 nm, no greater than 2800 nm, no greater than 2999 nm.

In some embodiments, the groove depth is equal to, or between 50 nm-2000 nm, or equal to, or between about 200 nm-1000 nm, or at least about 50 nm, or at least about 75 nm, or at least about 100 nm, or at least about 150 nm, or at least about 200 nm, or at least about 250 nm or at least about 500 nm, or at least about 1000 nm, or at least about 2000 nm.

In some embodiments, the width is equal to, or between about 300 nm-500 nm, about 500 nm-800 nm, 600 nm-900 nm, 700-1000 nm, about 1000-1200 nm or no greater than 1200 nm or 1500 nm. In some embodiments, a range for the groove depth is equal to, or between about 200 nm-1000 nm, or equal to, or equal to, or between 1000 nm-2000 nm, or between 1000-3000 nm.

In some embodiments, the width of the depth of the groove is equal to, or between 10-100 nm, for example no greater than about 10 nm, or no greater than about 20 nm, or no greater than about 30 nm, or no greater than about 40 nm, or no greater than about 50 nm, or no greater than about 60 nm, or no greater than about 70 nm, or no greater than about 80 nm, or no greater than about 90 nm, or no greater than about 100 nm or more than 100 nm in width. In some embodiments, the depth of the groove is equal to, or between 5 nm-1000 nm, for example no greater than about 5 nm, no greater than about 10 nm, no greater than about 20 nm, no greater than about 30 nm, no greater than about 40 nm, no greater than about 50 nm, no greater than about 60 nm, no greater than about 70 nm, or no greater than about 80 nm, or no greater than about 90 nm, no greater than about 100 nm, no greater than about 200 nm, no greater than about 300 nm, no greater than about 400 nm, or no greater than about 500 nm, or no greater than about 600 nm, or no greater than about 700 nm, or no greater than about 800 nm, or no greater than about 900 nm, or no greater than about 1000 nm, or no greater than about 1200 nm, or no greater than about 1400 nm, or no greater than about 1500 nm, or no greater than about 1600 nm, or no greater than about 1800 nm, or no greater than about 2000 nm in width. In some embodiments, the depth of the groove is equal to, or between about 200-800 nm, or equal to, or between about 100-200 nm, or equal to, or between about 200-400 nm, or equal to, or between about 400-600 nm, or equal to, or between about 600-800 nm, or equal to, or between about 800-1000 nm, or equal to, or between 1000 nm-2000 nm, or between 1000 nm-3000 nm.

D) Nanotexture in General

In some embodiments, the array of parallel grooves and ridges has a precision of texture of at least 90% fidelity, as evidenced by atomic force microscopy and/or electron microscopy. In some embodiments, the array of parallel grooves and ridges covers a large surface with high fidelity, for example, at least 1 $cm^2$, for example, glass coverslips or wells of a multi-well slide, or at least 2 $cm^2$, or at least about 3 $cm^2$, or the culture surface area of a multi-well plate, e.g., 12 cm×10 cm surface area, i.e., the surface area of a 6-well, a 12-well, a 24-well, a 48-well, 96-well or 384-well plate.

In some embodiments, the width of the ridge and the width of the groove provides a repeatable unit, which determines the periodicity of the parallel grooves and ridges. In some embodiments, the width of the groove and the width of the ridge are the same, and in some embodiments, the width of the ridge is greater than the width of the groove, and vice versa, i.e., the width of the groove can be wider than the width of the ridge.

The nanotopography can be of any conformation and geometry of parallel grooves and ridges that allows for anisotropic and polarized cell arrangement in the direction of the nanotextures. In some embodiments, the top or surface of the ridge is substantially planar, and in some embodiments it is convex, and in some embodiments, it is concave. In some embodiments, the ridge is pointed or angular. In some embodiments, the hollow or bottom of the groove is substantially planar, and in some embodiments, it is concave and in some embodiments, it is convex. Any combination of planar, convex or concave surfaces of the groves and ridges can occur, although it is generally preferred that the nanotextured area has a repeating unit of the same geometry. Thus, in some embodiments, the surface of the ridges and/or grooves all have the same geometry, e.g., they are all substantially planar. In alternative embodiments, the ridges and/or grooves have a variety of a combination of convex, concave or substantially planar surfaces. In some embodiments, the ridges and grooves are convex and concave respectively, to provide a corrugated cross-sectional appearance.

The parallel array of grooves and ridges has a periodicity defined by the length of the shortest interval over which the structure repeats its shape. Thus, one groove, with its given width and depth is separated from the next by a ridge of a given width—the period is set by the width of the groove and the width of the separating ridge, which together, make up the repeating unit of the parallel array. The lateral dimension of the array is defined by the shortest interval over which the structure repeats its shape times the number of such repeats. In some embodiments, the nanotexture is present on material applied to a glass surface, e.g., a coverslip.

(iii) Micropatterns on the Nanopatterned Surface of the Biomimetic Culture Platform:

As described herein, the technology described herein relates to an engineered biomimetic culture platform that comprises a nanopatterned surface and on the nanopatterned surface, an array of at least one repeatable micropattern cell migration unit, that includes at least one cell permissive migration pathway directing anisotropic diffusion behavior of cells, and at least one cell non-adherent region adjacent to the migration pathway, with at least one cell loading region at the proximal end of the migration pathway.

A) Cell Migration Unit

Different micropatterning and geometries of the of the cell permissive regions can be present in a single cell migration unit. For example, FIG. 8A shows an exemplary simple cell migration unit, which shows the migration pathway (i.e., cell permissive region) as strip patterned adjacent to a cell non-adherent region, and a cell loading region present at the proximal end of the migration pathway. In such an embodiment, cells plated in the cell loading region can migrate down the migration pathway, and will not substantially enter the cell non-adherent region.

In some embodiments, a cell migration unit can have multiple migration pathways (i.e. cell permissive regions) and multiple cell non-adherent regions. For example, as shown in FIG. 8B, one embodiment of the cell migration unit can comprise n number of migration pathways, and n number of cell non-adherent regions (i.e., a 1:1 ratio of migration pathways to non-adherent regions). In such an embodiment, each migration pathway is adjacent (or parallel to) at least one cell non-adherent region. In another embodiment, a cell migration unit can comprise a centrally located cell loading region, and extending perpendicular from cell loading region are n number of migration pathways, interdispersed between n number of cell non-adherent regions.

In another embodiment, as shown in FIG. 8C, a cell migration unit can comprise n number of migration pathways, and n+1 number of cell non-adherent regions. In such an embodiment, each migration pathway has a cell non-adherent region on each side.

Figure 8D:
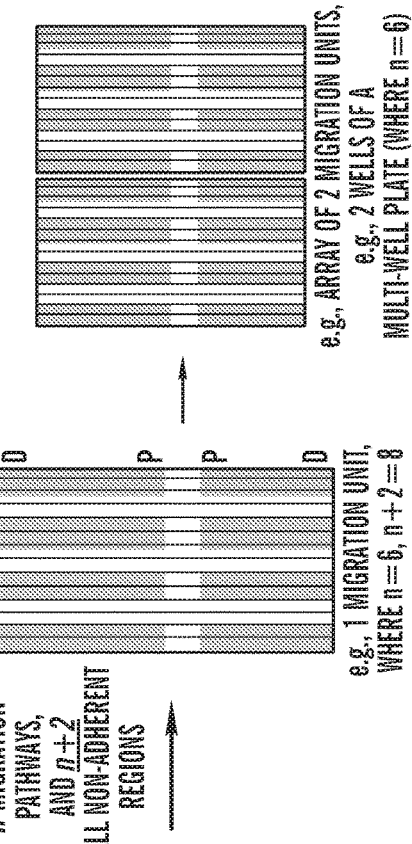
Figure 9:
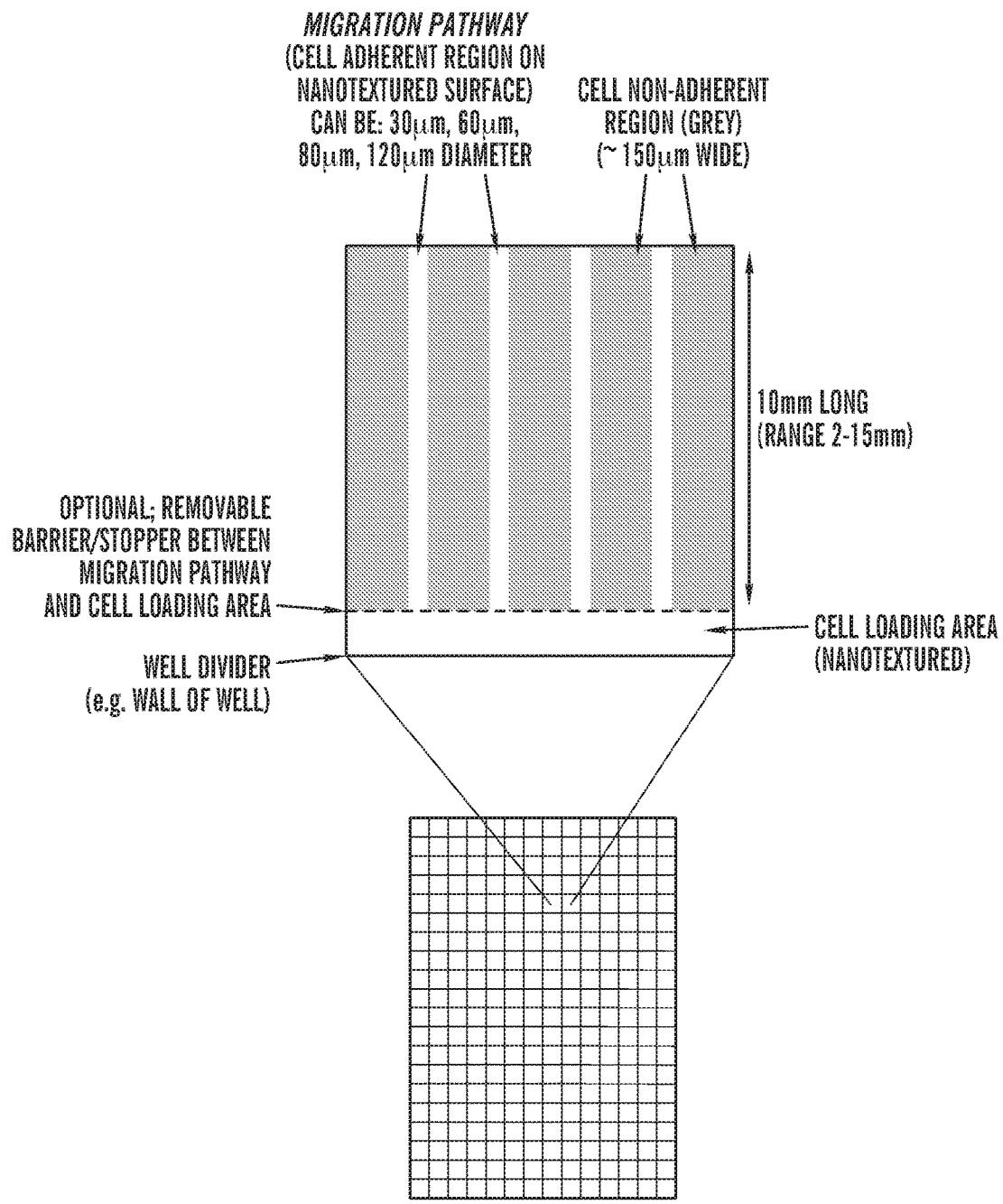
FIG. 9 is schematic of an exemplary cell migration unit present in an array. The cell migration units can be arranged in an array, e.g., of 96, or 384 format allowing HTS of migration properties of multiple cell populations at the same time.
Figure 10:
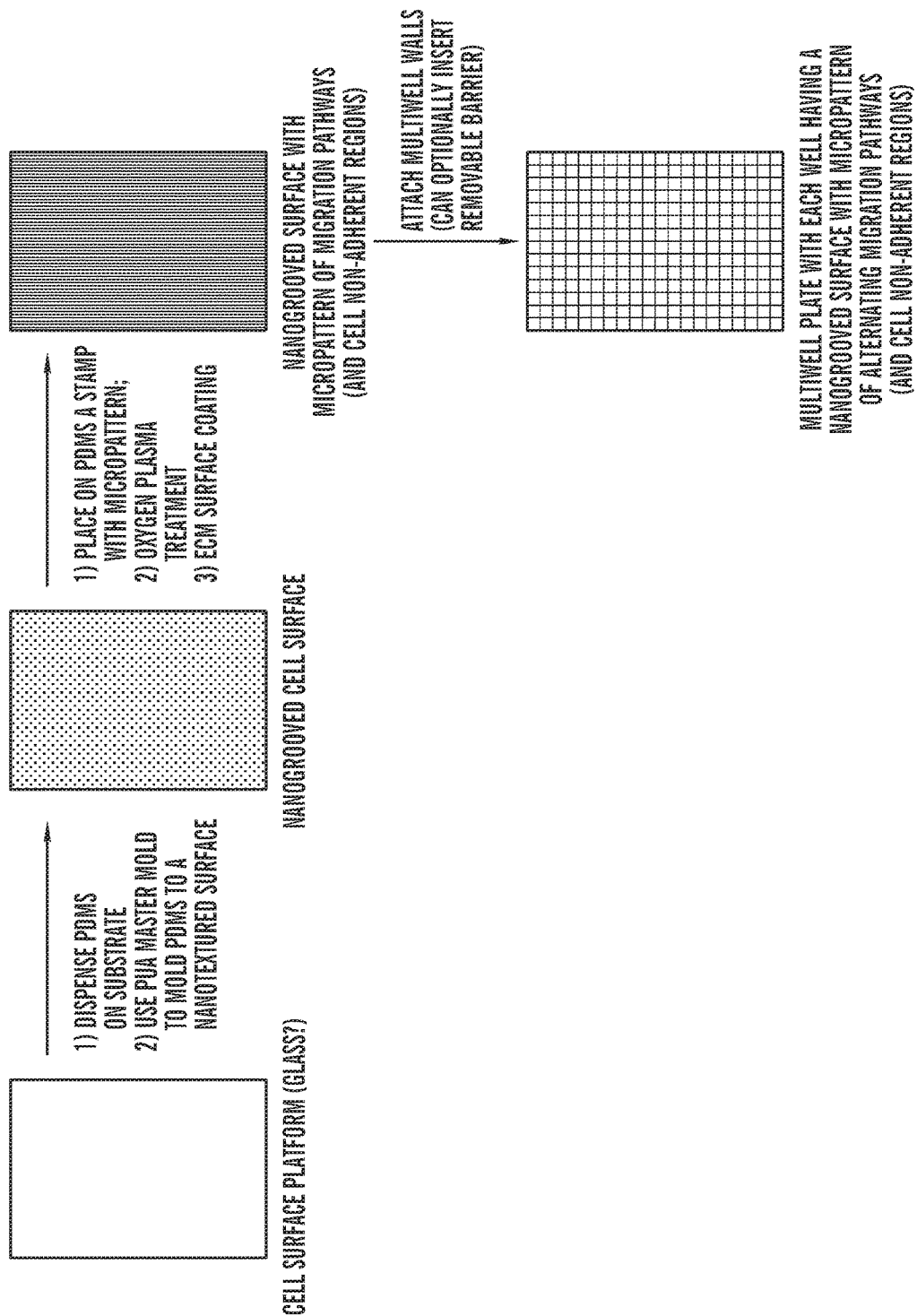
FIG. 10 is a schematic representation of the steps for fabricating the biomimetic culture platform. The surface platform is nanotextured using UV-assisted capillary force lithography, and then the nanopatterned surface is then micropatterned with the ECM-component coating using microstamp plasma lithography. A cell chamber wall/barrier can be attached or affixed to the surface of the substrate to generate a multi-well plate, or alternatively, the nanopatterning and micropatterning can be performed on the surface of a coverslip and placed in individual wells of a multi-well plate, or a directly on the culture surfaces of a multi-well plate.

In another exemplary embodiment as shown in FIG. 8D, a cell migration unit can comprise n number of migration pathways, and n+2 number of cell non-adherent regions. In such an embodiment, a cell migration unit can comprise a centrally located cell loading region, and extending perpendicular from cell loading region are n number of migration pathways, interdispersed between n+2 cell non-adherent regions, where each migration pathway has a cell non-adherent region adjacent to it.

In some embodiments, n can be, for example, 1, 2, 3, 4, 5, 6, 7, 8, 9, 10, or between 11-15, or between 15-20, or more than 20 but less than 50. In some embodiments, the cell loading region extends the entire width of the migration unit, therefore allowing the cells to migrate in any of the n number of migration pathways. Such an embodiment allows each migration pathway to be a replicate of each other.

It is encompassed that any geometry or shape of micropatterning of the migration pathways is envisioned and is not limited to the embodiments shown. For example, the cell migration unit can comprise central cell loading region with a spiral migration pathway extending therefrom, where each layer of the spiral is separated by cell non-adherent regions. Similarly, the cell migration unit can comprise a central cell loading region (e.g., circular) with multiple migration pathways extending perpendicular therefrom, i.e., in a flower-like or star-like pattern. Regardless of shape/geometry of the micropatterning of the cell migration unit, it is envisioned that the direction of the nanopatterning groove and ridges are substantially parallel with the longitudinal direction of the migration pathway.

In some embodiments, the cell migration units can be present on the nanopatterned surface as a repeating unit, and can be arranged in an array. This allows comparison of the migration properties of different cell populations in a single experiment, e.g., comparison of different cell populations (e.g., from different patient samples, or one cancer cell type versus another cancer cell type, or the migration properties in the presence or absence of an agent for screening agents which inhibit migration of cancer cells etc.). In some embodiments, the array comprises 2 cell migration units, or at least 3, or at least 4, or at least 6, or at least 8, or at least 12, or at least 16, or at least 24, or at least 48, or at least 96, or at least 384, or at least 1536. In some embodiments, the array comprises a number of cell migration units compatible with a multi-well plate and/or a multiwall slide (i.e., a multiwall culture slide or a cell chamber slide). In some embodiments, each well of a multi-well plate comprises a single cell migration unit.

In some embodiments, the migration pathways have a width of between 10 µm and 3000 µm. In some embodiments, the width is greater than 3000 µm, but smaller than 5000 µm. In some embodiments, the width of the migration pathway is selected from at least any of; at least about 10 µm, at least about 20 µm, at least about 30 µm, at least about 40 µm, at least about 50 µm, at least about 60 µm, at least about 70 µm, at least about 80 µm, at least about 90 µm, at least about 100 µm, at least about 110 µm, at least about 120 µm, at least about 130 µm, at least about 140 µm, at least about 150 µm, or greater than 150 µm but less than 3000 µm.

In some embodiments, the width of the migration pathway is selected from at least any of; no more than about 10 µm, no more than about 20 µm, no more than about 30 µm, no more than about 40 µm, no more than about 50 µm, no more than about 60 µm, no more than about 70 µm, no more than about 80 µm, no more than about 90 µm, no more than about 100 µm, no more than about 110 µm, no more than about 120 µm, no more than about 130 µm, no more than about 140 µm, no more than about 150 µm, or greater than 150 µm but less than 3000 µm.

Figure 1A:
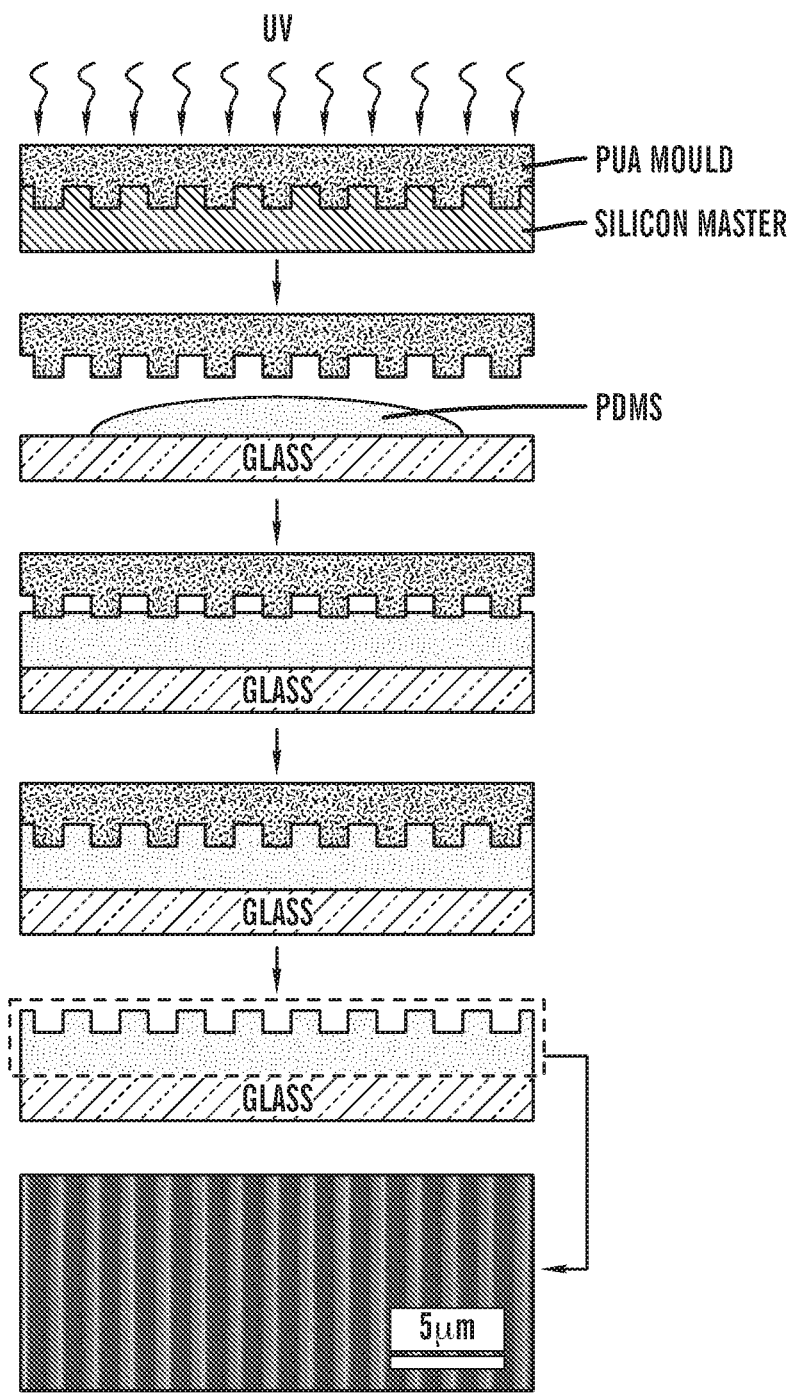
FIGS. 1A-1D show fabrication of an engineered biomimetic culture platform.

In some embodiments, where a cell migration unit comprises multiple migration pathways, the migration pathways can comprise the same width diameter (e.g., see FIG. 1C), or in some embodiments, the migration pathways can comprise different width, as disclosed in the Examples and FIG. 1A, where a cell migration unit comprises migration pathways of 30 µm, 60 µm, 80 µm and 120 µm.

In some embodiments, where there is an array of cell migration units, the migration pathways in each cell migration unit can be the same width dimensions, or alternatively they can be of different width dimensions. In some embodiments, where an array comprises multiple cell migration units, units within the array can comprise the same width of migration units, or different width. Stated another way, where different widths are included, one migration unit in the array can comprise migration pathways with a width of, e.g., 30 µm, and another cell migration unit in the same array can comprise migration pathways with a width of, e.g. 90 µm.

B) ECM-Component Coating

The cell permissive regions (i.e., cell migration pathways) of the cell migration units are coated with an ECM component. Such a coating can be selected from any, or a combination of ECM component proteins such as, fibronectin, fibrin, vitronectin, laminin, collagen, fibrinogen, silk or silk fibroin. In some embodiments, the ECM component coating is collagen. In some embodiments, the ECM component coating is laminin. In some embodiments, laminin is not used in the ECM component coating. In some embodiments, more than 1, or more than 2, or more than 3 or more than 3 but less than 10 different ECM proteins are used in the ECM component coating, e.g., a combination of collagen and laminin, etc.

In some embodiments, the ECM component coating can also comprise either, in admixture with the ECM component coating, or as a separately applied treatment, one or more growth factors, lipids, fatty acids, steroids, cytokines, hormones, or nucleic acid molecules that further promote or modulate migration of a cell, e.g., a tumor cell. In some embodiments, the ECM component coating comprises one or more growth factors, chemokines and/or chemoattractants selected from, for example, stromal-derived chemokine stromal-derived factor-1 (SDF-1), epidermal growth factor (EGF), platelet-derived growth factor (PDGF), placental growth factor (PlGF), transforming growth factor-β (TGF-β), VEGF, VEGF-A, HGF/SF (hepatocyte growth factor), monocyte chemotactic protein (MCP1) also known as CC chemokine ligand 2 (CCL2), FGF, CCL5, CXCL8/IL-8, bFGF [FGF-2], angiopoietins, and/or mechanotaxins or secreted proteases. In some embodiments, the ECM component coating comprises at least one or more of EGF, PDGF or HGF. In some embodiments, the ECM component coating comprises members of the cadherin family, e.g., E-cadherin, VE-cadherin, nectins, β-catenin or plakoglobin (γ-catenin) and the like.

In some embodiments, where collagen is present in the ECM component coating, it can be selected from collagen types I, II, III or IV or any of the 28 types of collagen described in literature (see, e.g., Tables 1 and 2 in US application No., US20100047305 for a detailed listing, which is incorporated herein in its entirety by reference). In some embodiments, the ECM component coating comprises naturally secreted ECM compositions as described in U.S. Pat. No. 6,284,284, which is incorporated herein in its entirety by reference.

In some embodiments, the ECM component coating present on the biomimetic culture platform comprises, either coated on its surface or within the ECM component coating, one or more agents selected from the group consisting of sphingosine phosphate or an analog thereof, fluoric acid, zFADvmk, cardiotropin, or a growth factor selected from the group consisting of FGF, HGF, IGF1, SDF1a, EGF, angiopoietin, BMP, erythropoietin (EPO), GDNG, c-GSF, GDF9, HDNF, GDF, thrombopoietin, TGFα, TGFβ, TNFα, PlGF, PDGF, interleukins IL1-IL17 and VEGF, CS1, RGD, domains in extracellular matrix proteins that bind to integrin receptors, and others well known to persons of ordinary skill in the art that promote or participate in cell/matrix interactions.

In some embodiments, the ECM component coating can comprise either, in admixture with the ECM component coating, or as a separately applied treatment, isolated ECM from normal epithelial tissue. In alternative embodiments, the ECM component can comprise isolated ECM from a tumor tissue, e.g., biopsy sample or other tumor ECM sample. In some embodiments, the ECM component can comprise, either, in admixture with the ECM component coating, or as a separately applied treatment, isolated ECM from cancerous epithelial tissue, e.g., mammary tumor tissue, colon cancer epithelial tissue and the like. The cell adherent regions can also comprise either, in admixture with the ECM component coating, or as a separately applied treatment, one or more growth factors, lipids, fatty acids, steroids, cytokines, hormones, or nucleic acid molecules that further promote or modulate migration of a cell, e.g., a tumor cell. In some embodiments, the cell adherent regions can comprise either, in admixture with the ECM component coating, or as a separately applied treatment, one or more cell populations that promote or support cell migration, thereby allowing essentially a co-culture of the seeded cells and the supporting cells present in or part of the ECM component coating.

In some embodiments, the ECM component coating can comprise ECM of epithelial cells. In some embodiments, the ECM component coating is specific for the cell type to be assessed on the BCP, as different tissues have different ECM types.

Thus, in some embodiments, the ECM component coating is tailored to the specific cell type present on the BCP. ECM of specific cell types are known by persons of ordinary skill in the art, for example, as disclosed in Lu et al. (2012, J. Cell Biol., 196(4); 395-406; "The extracellular matrix: a dynamic niche in cancer progression"); Hynes, R. O., (2009, Science, 326; 1216-1219; "The extracellular matrix: not just pretty fibrils"); Hynes R. O., and Naba, A. (2012, Cold Spring Harbor Perspect Biol., 4; a004903, "Overview of the Matrisome—An inventory of extracellular matric constituents and functions"); and Naba et al., (2016; Matrix Biol., 49; 10-24; "The extracellular matrix: tools and insights for the "omics" era"), each of which are incorporated herein in in their entirety by reference.

In some embodiments, the ECM component coating comprises at least one or more extracellular matrix proteoglycans selected from those listed in Table 1.

TABLE 1

Extracellular matrix proteoglycans.

HSPG2 heparan sulfate proteoglycan 2/perlecan complex
ASPN asporin
BGN biglycan
DCN decorin
FMOD fibromodulin
KERA keratocan
LUM lumican
OMD osteomodulin/osteoadherin
PRELP/prolargin (pro/arg-end/leu-rich repeat protein)
EPYC epiphycan
OGN osteoglycin/mimecan
OPTC opticin
CHAD chondroadherin
CHADL chondroadherin-like
NYX nyctalopin (probably GPI-linked)
NEPNP nephrocan (pseudogene in human)
PODN podocan
PODNL1 podocan-like 1
ACAN aggrecan
BCAN brevican
NCAN neurocan
VCAN versican
HAPLN1 hyaluronan and proteoglycan link protein 1
HAPLN2 hyaluronan and proteoglycan link protein 2
HAPLN3 hyaluronan and proteoglycan link protein 3
HAPLN4 hyaluronan and proteoglycan link protein 4
PRG2 proteoglycan 2, bone marrow PG
PRG3 proteoglycan 3
SPOCK1 testican 1
SPOCK2 testican 2
SPOCK3 testican 3
PRG4 proteoglycan 4/lubricin SO/HX
SRGN serglycin serglycin HS/CS
IMPG1 interphotoreceptor matrix proteoglycan 1 SEA domain CS
IMPG2 interphotoreceptor matrix proteoglycan 2 SEA domain CS
ESM1 endocan/endothelial cell-specific molecule 1 IB domain CS/DS In some embodiments, the EMC component coating comprises at least one or more extracellular matrix glycoproteins selected from any listed in Table 2.

TABLE 2

Exemplarly extracellular matrix glycoproteins.

Basement membrane components

Lama1-5 5 Laminin alpha subunits
Lamb1-4 3 Laminin beta subunits
Lamc1-3 3 Laminin gamma subunits
Nid1/2 2 Nidogens
Colq Collagen-like tail subunit of asymmetric acetylcholinesterase Major known ECM glycoproteins Eln Elastin
Emilin1-3 3 Emilins, elastin microfibril interfacers
Emid1/2 2 EMI domain-containing proteins
Fbln1/2/5/7 4 Fibulins
Efemp 1/2 Fibulins 3 and 4
Fbn1/2 2 Fibrillins
Fn1 Fibronectin
Fras1 Fraser syndrome 1 homolog
Gldn Gliomedin
Hmcn1/2 Hemicentins 1 and 2
Ibsp Integrin-binding sialoprotein, BSP
Matn1-4 4 Matrilin proteins
Mfap1a/b-5 6 Microfibrillar-associated proteins
Mmrn1 and 2 2 Multimerins
Npnt Nephronectin
Papln Papilin, proteoglycan-like sulfated glycoprotein
Postn Periostin, osteoblast-specific factor
Sparc/Sparcl1 Secreted acidic cysteine-rich glycoproteins SPARC and SPARC-like
Spp1/Srpx 2 Secreted phosphoprotein 1, osteopontin
Tnc/n/r/x 4-5 Tenascins
Thbs1-4 4 Thrombospondins-see also COMP/TSP5
Comp/TSP5 Cartilage oligomeric matrix protein (thrombospondin 5)

Nervous system-enriched ECM proteins

Agrn Agrin
Coch Cochlin
Ntn1-5 4 Netrins
Ntng1/g2 Netrins G1/G2
Reln Reelin
Slit1-3 3 Slit homologs
Sspo SCO-spondin
Tecta/b Tectorins c and 13

Vascular ECM proteins

Fga/b/g Fibrinogen c/13/y chains
Vtn Vitronectin
Vwf von Willebrand factor

ECM proteins of bones, cartilage, and teeth

Ambn Ameloblastin
Amelx Amelogenin X chromosome
Bglap2 Bone y-carboxyglutamate protein 2
Bglap-rs1 Bone y-carboxyglutamate protein-related sequence 1
Cilp Cartilage intermediate-layer protein, nucleotide pyrophosphohydrolase
Cilp2 Cartilage intermediate-layer protein 2
Dmp1 Dentin matrix protein 1
Dpt Dermatopontin
Dspp Dentin sialophosphoprotein
Mgp Matrix Gla protein CCN family proteins Cyr61 Cysteine rich protein 61, CCN1
Ctgf Connective tissue growth factor, CCN2
Nov Nephroblastoma overexpressed gene, CCN3
Wisp1-3 3 WNT1 inducible signaling pathway proteins, CCN4-6

Growth-factor-binding proteins

Bmper BMP-binding endothelial regulator
Igfals Insulin-like growth-factor-binding protein, acid labile subunit TABLE 2-continued Exemplarly extracellular matrix glycoproteins.

Igfbp1-7 7 Insulin-like growth-factor-binding proteins
Igfbpl1 Insulin-like growth-factor-binding protein-like 1
Kcp Kielin/chordin-like protein
Ltbp1-4 4 Latent transforming growth-factor 13-binding proteins
Other possible ECM proteins Abi3bp ABI gene family, member 3 (NESH)-binding protein
Adipoq Adiponectin, C1Q, and collagen domain-containing protein
Aebp1 AE-binding protein 1
Bsph1 Binder of sperm protein homolog 1
Cdcp2 CUB domain-containing protein 2
Creld1/2 Cysteine-rich with EGF-like domains 1 and 2
Crim1 Cysteine-rich transmembrane BMP regulator 1 (chordin like)
Crispld1/2 Cysteine-rich secretory protein LCCL domain-containing 1 and 2
Cthrc1 Collagen triple helix repeat containing 1
Ddx26b DEAD/H (Asp-Glu-Ala-Asp/His) box polypeptide 26B
Dmbt1 Deleted in malignant brain tumors 1
Ecm1 Extracellular matrix protein 1
Ecm2 Extracellular matrix protein 2, female organ, and adipocyte specific
Edil3 EGF-like repeats and discoidin I-like domains 3
Egflam EGF-like, fibronectin type III, and laminin G domains
Fgl1/2 Fibrinogen-like proteins 1 and 2
Fndc1/7/8 3 Fibronectin type III domain-containing proteins
Gas6 Growth arrest specific 6
Igsf10 Immunoglobulin superfamily, member 10
Lgi1-4 4 Leucine-rich repeat LGI family proteins
Lrg1 Leucine-rich a-2-glycoprotein 1
Mepe Matrix extracellular phosphoglycoprotein with ASARM motif
Mfge8 Milk fat globule-EGF factor 8 protein
Nell1/2 NEL-like 1 and 2
Oit3 Oncoprotein-induced transcript 3
Otog Otogelin
Pcolce/Pcolce2 2 Procollagen C-endopeptidase enhancer proteins
Pxdn Peroxidasin homolog
Rspo1-4 4 R-spondin homologs
Slamf6 SLAM family member 6
Smoc1 SPARC-related modular calcium-binding proteins 1 and 2
Sned1 Sushi, nidogen, and EGF-like domains 1
Spon1 Spondin 1, (f-spondin) extracellular matrix protein
Spon2 Spondin 2, extracellular matrix protein
Srpx2 Sushi-repeat-containing protein, X-linked 2
Svep1 Sushi, von Willebrand factor type A, EGF, and pentraxin domain-containing 1
Tgfbi Transforming growth factor 13-induced
Thsd4 Thrombospondin type I domain-containing 4
Tinag/Tinagl1 Tubulointerstitial nephritis antigen/tubulointerstitial nephritis antigen-like 1
Tnfaip6 Tumor necrosis factor a-induced protein 6
Tsku Tsukushin
Vit Vitrin
Vwa1-5 5 von Willebrand factor A domain-containing proteins
Vwc2/2l/e 3 von Willebrand factor C domain-containing proteins
VwD/E 2 von Willebrand factor D and EGF domain proteins
Zp1-4 4 Zona pellucida glycoproteins
Zp3r Zona pellucida 3 receptor
Zpld1 Zona pellucida-like domain-containing 1

TABLE 2-continued

Exemplarly extracellular matrix glycoproteins.

Novel predicted ECM proteins

2010321M09Rik RIKEN cDNA 2010321M09 gene
5430419D17Rik RIKEN cDNA 5430419D17 gene
6130401L20Rik RIKEN cDNA 6130401L20 gene
9230107M04Rik RIKEN cDNA 9230107M04 gene
A930038C07Rik RIKEN cDNA A930038C07 gene
AW551984 Expressed sequence AW551984
C330046G03Rik RIKEN cDNA C330046G03 gene
D17H6556E-3 DNA segment, Chr 17, human D6S56E 3
Gm106 Predicted gene 106
Gm414 Predicted gene 414
Gm6924 Predicted gene 6924

In some embodiments, one or more agents can be selected from the group consisting of an antibody, antigen, glycoprotein, lipoprotein, DNA, RNA, polysaccharide, lipid, growth hormone, organic compound, and inorganic compound.

In some embodiments, the ECM component coating present on the biomimetic culture platform comprises, either coated on its surface or within the ECM component coating, poly-L-lysine, poly-D-lysine, poly-ornithine, vitronectin or erythronectin.

Techniques for covalently bonding peptides to the surface of substrates such as polymers can be performed by a variety of conventional methods using known coupling agents and derivatization methods which are known to those of skill in the art. The technology described herein also relates to the covalent coupling of such peptides to the nanotextured surface of the substrate either directly or via an appropriate linking or spacer group. U.S. Pat. No. 4,789,601, incorporated by reference in its entirety, describes a polyorganosiloxane composition having a biocompatible surface. The surface of the composition is treated with a primary amine or a peptide. This patent is incorporated herein by reference as teaching methods of modifying polymer surfaces.

U.S. Pat. No. 5,733,538, incorporated herein by reference, describes surface-modifying copolymers having cell adhesion properties. The surface modification techniques and polymers described therein also may be useful in conjunction with the substrates derived herein. More particularly, the patent discusses a hemocompatible surface-modifying additive for modifying polyurethane or polyurethane urea substrates. The additive has a polyurethane or polyurethane urea hard block or an alternative block which is miscible with the poly(urethane) or poly(urethane-urea) base polymer, a polysiloxane hydrophobic soft block, an optional hydrophilic spacer and a peptide selected from the group consisting of Arg-Gly-Asp, X-Arg-Gly-Asp, Arg-Gly-Asp-X and X-Arg-Gly-Asp-X', wherein X and X' are amino acids.

In some embodiments, a peptide GRGDSP (SEQ ID NO: 1) (a Fibronectin Receptor Ligand) and/or YIGSRC (SEQ ID NO: 2) (a Laminin Receptor Ligand) can be covalently bound to the surface of the biomimetic culture platform, e.g., at the cell permissive regions to increase cell attachment. Cell attachment efficiency can be analyzed as previously described (Samarel and Engelmann, Am J Physiol 261, H1067-77, 1991). Briefly, plating efficiency is analyzed as the amount of recovered DNA from adherent cells 4 h after plating compared to the amount of DNA in the plating suspension. In the case of Type I collagen-coated plastic dishes, plating efficiency of freshly isolated neonatal rat ventricular myocytes was 68° 04% (Samarel and Engelmann, Am J Physiol 261, H1067-77, 1991). It is expected that plating efficiency will vary between flat and microtextured surfaces, and with the two peptides (whether used alone or in combination).

B2) Coatings and Modifications to the Cell Permissive Regions and/or Biomimetic Culture Platform The surface of the substrate of the biomimetic culture platform can be modified with one or more bioactive agents, deposited or adsorbed on the polymer surface, to promote tumor cell or other cell type attachment to the substrate. Accordingly, in some embodiments, the cell permissive regions of the biomimetic culture platform comprises within its polymer matrix, or on its surface, a bioactive agent or cell population (i.e., co-culture) that enhances attachment or migration of the tumor cell population. In some embodiments, a portion or the whole region of the cell permissive region, can comprise a removable substrate layer, such as a surface layer.

In some embodiments, the cell permissive region, which comprises an ECM component coating as disclosed herein, can additionally provide controlled release of bioactive factors to the migrating cell population to mimic an in vivo tumor environment, or to sustain or control subsequent cell growth and proliferation of the cells seeded in the cell loading region, or migrating along the migration pathways of the biomimetic culture platform as described herein. In such a way, a cell population present on the biomimetic culture platform can be supplied with a constant source of growth factors and other agents during use or culture on the surface of the platform.

Additionally, in some embodiments, the surface of the biomimetic culture platform can be modified to include one or more of the agents selected from following group: (a) extracellular matrix proteins to direct cell adhesion and function (e.g., collagen, fibronectin, laminin, etc.); (b) growth factors to direct cell function specific to cell type (e.g., nerve growth factor, bone morphogenic proteins, vascular endothelial growth factor, etc.); (c) lipids, fatty acids and steroids (e.g., glycerides, non-glycerides, saturated and unsaturated fatty acids, cholesterol, corticosteroids, sex steroids, etc.); (d) sugars and other biologically active carbohydrates (e.g., monosaccharides, oligosaccharides, sucrose, glucose, glycogen, etc.); (e) combinations of carbohydrates, lipids and/or proteins, such as proteoglycans (protein cores with attached side chains of chondroitin sulfate, dermatan sulfate, heparin, heparan sulfate, and/or keratan sulfate); glycoproteins [e.g., selectins, immunoglobulins, hormones such as human chorionic gonadotropin, Alpha-fetoprotein and Erythropoietin (EPO), etc.]; proteolipids (e.g., N-myristoylated, palmitoylated and prenylated proteins); and glycolipids (e.g., glycoglycerolipids, glycosphingolipids, glycophosphatidylinositols, etc.); (f) biologically derived homopolymers, such as polylactic and polyglycolic acids and poly-L-lysine; (g) nucleic acids (e.g., DNA, RNA, etc.); (h) hormones (e.g., anabolic steroids, sex hormones, insulin, angiotensin, etc.); (i) enzymes (types: oxidoreductases, transferases, hydrolases, lyases, isomerases, ligases; examples: trypsin, collagenases, matrix metalloproteinases, etc.); (j) pharmaceuticals (e.g., beta blockers, vasodilators, vasoconstrictors, pain relievers, gene therapy, viral vectors, anti-inflammatories, etc.); (k) cell surface ligands and receptors (e.g., integrins, selectins, cadherins, etc.); and (l) cytoskeletal filaments and/or motor proteins (e.g., intermediate filaments, microtubules, actin filaments, dynein, kinesin, myosin, etc.).

In some embodiments, a polymer substrate of the biomimetic culture platform as disclosed herein can also be seeded or coated with functional elements, including drugs or any type of chemotaxis agent or factor.

In some embodiments, the substrate of the biomimetic culture platform can be coated with materials that promote electroconductivity, thereby permitting the effect of an electrical impulse the migration properties of a cell population to be assessed. In some embodiments, such material can be selected from the group consisting of charcoal, graphene, graphene oxide, reduced graphene oxide (rGO), nanotubes, titanium (Ti), Ti—Al—V alloys, gold (Au), chromium, metal oxides, semiconductor oxides, metal nitrides, semiconductor nitrides, whereby electrical conductivity, or other physico-chemical property is modulated in a manner that influences the phenotype of the cells, or permits measurement or application of electrical impulses to cells on the substrate. In some embodiments, the biomimetic culture platform comprises electroactive polymer fibers, that yield fibers that exhibit crystalline structures in polar form due to strong electromagnetic fields. Exemplary systems and methods for aligning the fibers are disclosed in US Application 2009/0108503, which is incorporated herein in its entirety by reference.

In some embodiments, the substrate of biomimetic culture platform can comprise a layer of thermoresponsive material. A thermoresponsive material is one which shrinks uniformly without substantial distortion when the temperature is changed. In some embodiments, a thermoplastic material can be used to remove a substantial monolayer of migrated tumor cells along the migration pathways. For example, thermoresponsive material can be placed at the distal ⅓, or distal ⅙ or distal 1/10 of the migration pathway to allow easy removal and collection of the cells that have migrated the furthest along the migration pathway in a predetermined period of time.

A "thermoresponsive material" is intended to mean a plastic material which shrinks upon heating. In one aspect, thermoplastic materials are those which shrink uniformly without distortion. The shrinking can be either bi-axially (isotropic) or uni-axial (anisotropic). Suitable thermoplastic materials for inclusion in the compositions and methods as described herein include, for example, high molecular weight polymers such as acrylonitrile butadiene styrene (ABS), acrylic, celluloid, cellulose acetate, ethylene-vinyl acetate (EVA), ethylene vinyl alcohol (EVAL), fluoroplastics (PTFEs, including FEP, PFA, CTFE, ECTFE, ETFE), ionomers kydex, a trademarked acrylic/PVC alloy, liquid crystal polymer (LCP), polyacetal (POM or Acetal), polyacrylates (Acrylic), Poly(methyl methacrylate) (PMMA), polyacrylonitrile (PAN or Acrylonitrile), polyamide (PA or Nylon), polyamide-imide (PAI), polyaryletherketone (PAEK or Ketone), polybutadiene (PBD), polybutylene (PB), polybutylene terephthalate (PBT), polyethylene terephthalate (PET), Polycyclohexylene Dimethylene Terephthalate (PCT), polycarbonate (PC), polyhydroxyal kanoates (PHAs), polyketone (PK), polyester polyethylene (PE), polyetheretherketone (PEEK), polyetherimide (PEI), polyethersulfone (PES), polysulfone polyethylenechlormates (PEC), polyimide (PI), polylactic acid (PLA), polymethylpentene (PMP), polyphenylene oxide (PPO), polyphenylene sulfide (PPS), polyphthalamide (PPA), polypropylene (PP), polystyrene (PS), polysulfone (PSU), polyvinyl chloride (PVC), polyvinylidene chloride (PVDC), polyolefin, and spectralon.

In some embodiments, a transitional polymer can be coated onto the substrate of the biomimetic culture platform.

In one embodiment, a transitional polymer is a thermally sensitive polymer that can be dissolved to cause the release of the cells from the biomimetic culture platform. An example of such a polymer is linear, non-cross-linked poly(N-Isopropylacrylamide), which is a solid when dehydrated, and which is a solid at 37° C. (wherein the polymer is hydrated but relatively hydrophobic). However, when the temperature is dropped to less than 32° C. (where the polymer is hydrated but relatively hydrophilic), the polymer becomes a liquid, thereby releasing the polymer substrate.

In another embodiment, a transitional polymer is a thermally sensitive polymer that becomes hydrophilic, thereby releasing a hydrophobic substrate coated thereon. An example of such a polymer is cross-linked poly(N-Isopropylacrylamide), which is hydrophobic at 37° C. and which is hydrophilic at 32° C.

In yet another embodiment, the transitional polymer is an electrically actuated polymer that becomes hydrophilic upon application of an electric potential to thereby release a hydrophobic (or less hydrophilic) structure coated thereon. Examples of such a polymer include poly(pyrrole)s, which are hydrophobic when oxidized and hydrophilic when reduced. Other examples of polymers that can be electrically actuated include poly(acetylene)s, poly(thiophene)s, poly(aniline)s, poly(fluorene)s, poly(3-hexylthiophene), polynaphthalenes, poly(p-phenylene sulfide), and poly(paraphenylene vinylene)s, etc.

In still another embodiment, the transitional polymer is a degradable polymer that can be dissolved to release the biomimetic culture platform. In one example, the polymer substrate (e.g., polylactic acid, polyglycolic acid, poly(lactic-glycolic) acid copolymers, nylons, etc.) undergoes time-dependent degradation by hydrolysis. In another example, the polymer undergoes time-dependent degradation by enzymatic action (e.g., fibrin degradation by plasmin, collagen degradation by collagenase, fibronectin degradation by matrix metalloproteinases, etc.). It will be understood by those skilled in the art that the foregoing list of optional substances is not intended to be exhaustive and that other materials can be admixed with, or used in conjunction with substrates within the practice of the technology described herein.

C) Cell Non-Adherent Regions

The cell non-adherent regions of the cell migration units essentially do not allow cells to stick or attach to the surface. In some embodiments, the cell non-adherent regions are hydrophobic regions, or have been treated with a hydrophobic substrate. In some embodiments, the cell non-adherent regions is the non-treated polymer substrate material, that is, cell non-adherent regions can be defined by region left without ECM-component coating. In some embodiments, the cell non-adherent region has not undergone treatment, e.g., with oxygen plasma material or other technique to change a surface to a hydrophobic to a hydrophilic surface.

In some embodiments, the width of the cell non-adherent region between migration pathways on an array is between 20 μm and 3000 μm. In some embodiments, the cell non-adherent region has the same width as the width of the cell adherent region (i.e., if the cell adherent region has a width of 20 μm, the cell non-adherent region is also 20 μm). In some embodiments, the cell non-adherent region has a larger width than the width of the cell adherent region (i.e., if the cell adherent region has a width of 20 μm, the cell non-adherent region can be, e.g., greater than 20 μm, e.g., 40 μm). In some embodiments, the cell non-adherent region has a smaller width than the width of the cell adherent region (i.e., if the cell adherent region has a width of 80 μm, the cell non-adherent region can be, e.g., smaller than 80 μm, e.g., 60 μm, or 50 μm, or 40 μm, or 30 μm, or 20 μm).

In some embodiments, the width of the cell non-adherent region is greater than 50 μm, but smaller than 3000 μm. In some embodiments, the width of the cell non-adherent region is selected from any of at least 20 μm, or equal to or between 20-80 μm, at least about 100 μm, at least about 200 μm, at least about 300 μm, at least about 400 μm, at least about 500 μm, at least about 600 μm, at least about 700 μm, at least about 800 μm, at least about 900 μm, at least about 1000 μm, at least about 1100 μm, at least about 1200 μm, at least about 1300 μm, at least about 1400 μm, at least about 1500 μm, or greater than 1500 μm but less than 3000 μm.

In some embodiments, the width of the cell non-adherent region is selected from any of no more than about 100 μm, no more than about 200 μm, no more than about 300 μm, no more than about 400 μm, no more than about 500 μm, no more than about 600 μm, no more than about 700 μm, no more than about 800 μm, no more than about 900 μm, no more than about 1000 μm, no more than about 1100 μm, no more than about 1200 μm, no more than about 1300 μm, no more than about 1400 μm, no more than about 1500 μm, or greater than 1500 μm but less than 3000 μm.

D) Cell Loading Region

The cell loading region of the cell migration unit is configured for seeding and culturing the cell population prior to the beginning of the migration assay. In some embodiments, it is located at the proximal end of at least one migration pathway, and if the cell migration unit has multiple migration pathways, the cell loading region is connected to each migration pathway. Such an embodiment allows the migration properties of a cell population to be assessed in replicate (e.g., duplicate, triplicate etc.). The cell loading region can comprise the nanopatterning of nanogrooves, which are aligned in the direction of the migration pathways extending from the cell loading region, or alternatively, the cell loading region can comprise a substantially flat surface (e.g., lack nanogrooves).

In some embodiments, the cells are plated in the cell loading region for a pre-determined time to allow confluence or a single cell layer. In some embodiments, cells can be plated or introduced into the cell loading region in a matrix, e.g., MATRIGEL™ or other cell culture scaffold, and allowed to reach confluence or alternatively, form a single cell layer in a predetermined time, after which media is added to the well in which the cell migration unit is present, allowing the cells to migrate from the cell loading region into the migration pathways.

In some embodiments, the cell loading region has a surface area that allows for seeding of at least about 100 cells, or at least about 200 cells, or at least about 300 cells, or at least about 400 cells, or at least about 500 cells, or at least about 600 cells, or at least about 700 cells, or at least about 800 cells, or at least about 900 cells, or at least about 1000 cells, or at least about 2000 cells, or at least about 3000 cells, or at least about 4000 cells, or at least about 5000 cells, or at least about 6000 cells, or at least about 7000 cells, or at least about 8000 cells, or at least about 9000 cells, or at least about 10,000 cells or greater than 10,000 cells. In some embodiments, cells are seeded at 1000-2000 cells/mm$^2$, or at least about 1000 cells/mm$^2$, or at least about 1100 cells/mm$^2$, or at least about 1200 cells/mm$^2$, or at least about 1400 cells/mm$^2$, or at least about 1600 cells/mm$^2$, or at least about 1800 cells/mm$^2$, or at least about 2000 cells/mm$^2$.

E) Removable Cell-Impermeable Barrier

In some instances the cell loading region can be configured to allow placement of a removable cell impermeable barrier which separates the cells in the cell loading region from entering the migration pathway during the pre-defined period of time when the cells are cultured in the cell loading region (i.e., before the beginning of the assay and/or prior to monitoring the migration behavior of the cells). In some embodiments, the cells are introduced and cultured in the cell loading region and are prevented from entering and migrating along the migration pathways by a removable cell impermeable barrier. In some embodiments, the PDMS micropatterned stamp can act as a removable cell impermeable barrier, and in such an embodiment, when cells have reached confluence, the micropatterned stamp is removed and the cells allowed to enter the migration pathways.

For example, in one embodiment of a biomimetic culture platform for an epithelial cancer cell migration assay, epithelial cancer cells can be seeded on an array of migration cell units. Firstly, the substrate is nanopatterned and then the microstamp is placed on the nanotextured surface. In some embodiments, after the micropattern is applied and the ECM-component coating is present on the cell-adherent regions, before the microstamp (or stencil) is removed, cells are seeded in the cell loading region and cultured for a time sufficient to reach a single cell layer or confluence. After the cells have formed a monolayer, the microstamp is removed and the cells allowed to migrate along the migration pathways for a selected or predetermined time.

(iv) Fabrication of a Biomimetic Culture Platform (BCP).

Figure 1B:
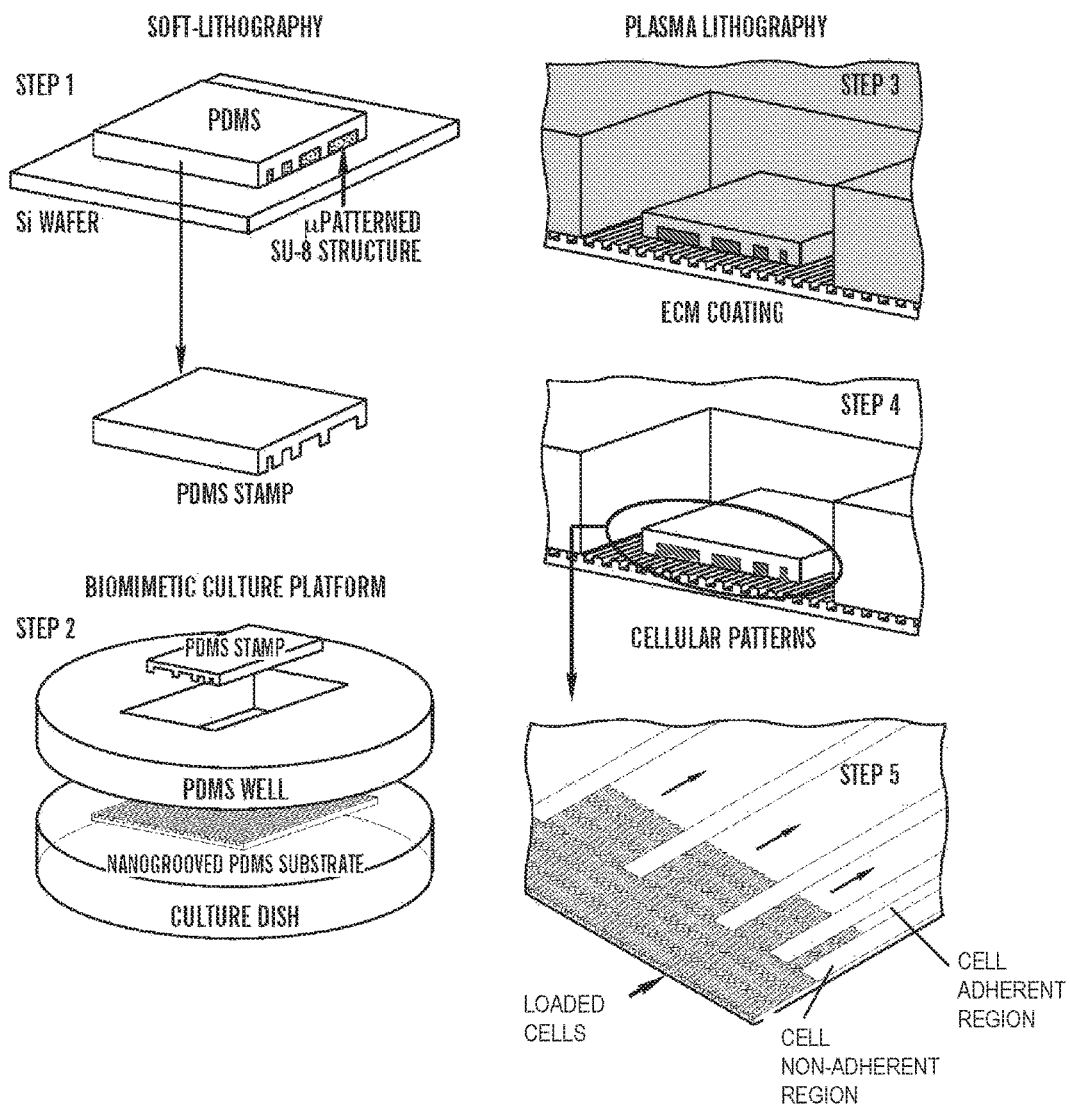

FIGS. 1A and 1B illustrate an exemplary method of fabricating the biomimetic culture platform as disclosed herein, and involves a 2 step process: Step 1 involves forming the nanotextured array of parallel grooves and ridges; and Step 2 involves micropatterning the repeatable cell migration unit, e.g., micropatterning the cell permissive regions, cell non-adherent regions and cell loading regions on the nanotextured array.

(i) Step 1: Nanofabrication of the Nanopatterned Array of Grooves and Ridges

In some embodiments, the nanotextured array of parallel grooves and ridges is generated using a process selected from the group consisting of any of capillary force lithography, nanoindentation, e-beam lithography, and electrospinning. In some embodiments, UV-assisted capillary force lithography is used.

In some embodiments, the array of parallel grooves and ridges is formed by capillary force lithography and/or thermal and UV based curing methods. In some embodiments, the array of parallel grooves and ridges on the substrate can be patterned with spatial control spanning the nanometer-length scales. This level of spatial control can be achieved via patterning techniques including but not limited to soft lithography, self-assembly, vapor deposition and photolithography. Each of these techniques is discussed, in turn, below.

Capillary Force Lithography.

Poly(urethane acrylate) (PUA) or other polymers can be used as mold material and poly(dimethylsiloxane) (PDMS) as a solvent absorbent. PUA molds are generated by drop-dispensing a PUA precursor onto a patterned silicon master wafer fabricated by standard photolithography. Next, a poly (ethylene terephthalate) (PET) film (thickness: 75 µm) is pressed lightly against the liquid drop in order to be used as a supporting backplane. Polymer replicas are fabricated by exposing the PUA to UV for a few tens of seconds and then peeling away the PET film with the polymer from the silicon master. To complete polymer curing, the replicas are exposed to UV for several hours overnight. PDMS solvent absorbers are made by mixing the PDMS precursor with the curing agent in a 10:1 mixing ratio and curing it at 60° C. for 10 hrs. The cured PDMS molds are manually removed and cut prior to use. These molds are now available for capillary force lithography. The substrate is nanotextured using nanoimprint lithography. In brief, glass coverslips are washed with isopropyl alcohol for 30 min in a water sonicator and dried under a nitrogen stream. Polymer or hydrogel solution is prepared in the relevant solvent, e.g. chloroform, and drop-dispensed onto the glass coverslip. A flat PDMS mold is placed on the dispensed solution to absorb the solvent and obtain a smooth, flat polymer layer. A light pressure (~10 kPa) is applied to evenly disperse the polymer on the PDMS mold for 5 min. Coverslips are placed on a preheated plate (120° C.) for 5 min to remove residual solvent and increase adhesion between the polymer and the cover glass. Next, a nanopatterned PUA mold is placed onto the polymer coated glass and the polymer is embossed with the nanopattern by applying constant pressure (~100 kPa) and heat (120° C.) for 15 min. After this thermal imprinting process, the assembled substrates are cooled to room temperature and the PUA mold carefully peeled off. Finally, the prepared nanotextured substrate is stored in a desiccator to remove residual solvent before step 2 begins (e.g., micropatterning of the cell adherent, cell non-adherent and cell loading regions). For UV assisted CFL, UV is used instead of thermal curing to polymerize the polymer.

a) Soft Lithography:

In soft lithography, structures (particularly those with features measured on the scale of 1 nm to 1 µm) are fabricated or replicated using elastomeric stamps, molds, and conformable photomasks. One such soft lithography method is microcontact printing using a polydimethylsiloxane stamp. Microcontact printing has been realized with fibronectin, laminin, vitronectin and fibrinogen and can be extended to other extracellular matrix proteins including, but not limited to collagens, fibrin, etc. Other polymers can be used as well, as this soft lithography method is quite versatile. There are few, if any, limitations on the geometry of the polymer structure(s) beyond the types of patterns that can be created in the polydimethylsiloxane stamps used for microcontact printing. The range of patterns in the stamps, in turn, is presently limited only by the current microprocessing technology used in the manufacture of integrated circuits. As such, available designs encompass nearly anything that can be drafted in modern computer-aided-design software. Multiple layers of polymers can be printed on top of one another using the same or different stamps with the same or different proteins to form an integrated poly-protein (poly-polymer) layer that can subsequently be released and used.

b) Self Assembly:

Various polymers will spontaneously form self-assembled structures. Examples, without limitation, of self-assembly include assembly of collagen into fibrils, assembly of actin into filaments and assembly of DNA into double strands and other structures depending on base-pair sequence. The self-assembly can be directed to occur on the transitional layer to create a nanometer-scale spatially organized polymer layer. Further, self-assembly can be combined with soft lithography to create a self-assembled layer on top of a soft lithographically patterned polymer; alternatively, the processes can be carried out in the reverse order. The self-assembled polymer, depending on the strength and stability of intermolecular forces, may or may not be stabilized using a cross-linking agent (for example, glutaraldehyde, formaldehyde, paraformaldehyde, etc.) to maintain integrity of the polymer layer upon release from the transitional layer.

Otherwise, existing intermolecular forces from covalent bonds, ionic bonds, Van der Waals interactions, hydrogen binding, hydrophobic/hydrophilic interactions, etc., may be strong enough to hold the polymer substrate together.

c) Vapor Deposition:

Using a solid mask to selectively control access to the surface of the transitional polymer, polymers can be deposited in the accessible regions via condensation from a vapor phase. To drive polymers into a vapor phase, the deposition is performed in a controlled environmental chamber where the pressure can be decreased and the temperature increased such that the vapor pressure of the polymer approaches the pressure in the environmental chamber. Polymer surfaces produced via vapor deposition can be combined with polymer surfaces created by self-assembly and/or by soft lithography.

d) Patterned Photo-Cross-Linking:

Patterned light, x-rays, electrons or other electromagnetic radiation can be passed through a mask by photolithography; alternatively, the radiation can be applied in the form of a focused beam, as in stereolithography or e-beam lithography, to control where the transitional polymer polymers attach. Photolithography can be used with polymers that intrinsically photo-cross-link or that change reactivity via the release of a photolabile group or via a secondary photosensitive compound to promote cross-linking or breaking of the polymer chains so that the surface areas that are exposed to light are rendered either soluble or insoluble to a developing solution that is then applied to the exposed polymer to either leave only the desired pattern or remove only the desired pattern. The polymer is provided in an aqueous solution of polymer intrinsically photosensitive or containing an additional photosensitive compound(s).

Polymer Release and Substrate Formation.

The transitional polymer layer dissolves or switches states to release the polymer structure(s). For example, a transitional polymer layer formed of PIPAAm (non-cross-linked) will dissolve in an aqueous media at a temperature less than 32° C. In another example, a transitional polymer layer is formed of PIPAAm (cross-linked) will switch from a hydrophobic to hydrophilic state in an aqueous media at a temperature less than 32° C. The hydrophilic state will release the polymers. In yet another embodiment, the transitional polymer layer includes a conducting polymer, such as polypyrrole, that can be switched from a hydrophobic to hydrophilic state by applying a positive bias that switches the conducting polymer from a reduced to oxidized state. In additional embodiments, the transitional polymer layer can include a degradable polymer and/or polymer that undergoes time-dependent degradation by hydrolysis (as is the case, for example, for polylactic and polyglycolic acid) or by enzymatic action (for example, fibrin degradation by plasmin). These polymer structure(s) can then be further manipulated for the desired application.

The techniques of microfabrication and micromachining have been used to create precisely controlled biomaterial surfaces via photopatterning and etching (Desai et al., Biotechnol Bioeng 57:118-120, 1998; Bhatia et al, Biotech. Prog. 14:378-387, 1998; Chen et al., Biotech Prog. 14:356-363, 1998). Microfabricated substrates can provide unique advantages over traditional biomaterials due to their ability to control surface microarchitecture, topography, and feature size in the nanometer and micron size scale, and control of surface chemistry in a precise manner through biochemical coupling or photopatterning processes. With the capability to design components spanning from the millimeter down to the nanometer range, few other engineering technologies can so closely parallel the microdimensional scale of living cells and tissues.

Traditionally, microfabrication has only been applied to semiconductor materials due to their oxidation and etching properties, using expensive microfabrication equipment. However, techniques to translate micromachined structures from inorganic to organic polymeric materials have been introduced (Schmidt and von Recum, Biomaterials, 12: 385-389, 1991; Bucaro et al, IEEE Conference Transactions 0-7803-3869-3/97:217-219, 1997). This opens up unique opportunities in biological and tissue engineering applications.

The ability to spatially localize and control interactions of cell types on polymeric materials presents an opportunity to engineer hierarchically and more physiologically correct tissue analogs for mechanical, biochemical, and functional testing. The arrangement of cells in more complex two and three dimensional arrangements has beneficial effects on cell differentiation, maintenance, and functional longevity.

The substrates as described herein can provide a transparent biocompatible surface with specific nanoarchitectures upon which cells, e.g., tumor cells and other cell types can be grown. In an exemplary procedure, the nanotextured substrates are prepared using silicone membranes. Starting with a clean silicon wafer, a 5 µm conformal layer of light sensitive photoresist (Michrochem SU8-5, Michrochem Corp., Newton, Mass.) is spun onto the wafer at 1500 RPM for 30 seconds and soft baked at 90° C. for 6 minutes. A photomask is used to define the pattern on to the photoresist layer upon exposure to UV light. Arrays of ridges can be photolithographically defined. The resulting photoresist structure is developed and hard baked. Subsequently, the surface is spray coated or dipped into adhesion demoter and a thin layer of parylene is deposited on the photoresist/silicon substrate. The parylene deposition layer is approximately 25 microns in thickness. The parylene layer forms a flexible mold for the elastomeric silicone. Subsequently, silicone (polydimethysiloxane), which is prepared by mixing elastomer and catalyst (A 103 Factor II Inc.) in a 10:1 ratio, is deposited on top of the parylene mold and allowed to cure at room temperature for 24-48 hours. The silicone can then be peeled off the parylene and cut to the desired shape and size.

The process for creating nanogrooves is similar except that a positive photoresist is used. Shipley 1818 photoresist is spun on the wafer at 500 RPM for 180 seconds. After a 5 minute soft bake the wafer is patterned with a mask aligner for 13 seconds at 20 mW. This can result in longitudinal grooves of 5 nm depth. The width and spacing of the grooves can be adjusted as desired according to the mask. The wafer is placed in developer (351 Shipley) for 0.9 minutes with continuous motion and rinsed with deionized water. The longitudinal grooves orient the myocytes and also to provide a greater surface area for lateral attachment.

(ii) Step 2: Micropatterning of the Nanotextured Substrate.

FIG. 1B shows an exemplary method of micropatterning the nanotextured substrate to produce the biomimetic culture platform disclosed herein.

In an exemplary method, microstamp-assisted plasma lithographic techniques are used for micropatterning of the cell migration unit and for the ECM component coating in the cell permissive regions (i.e., migration pathways). A microchannel-patterned PDMS stamp (referred to as a "microstamp" or "micropatterned stamp" herein) can be fabricated using soft-lithographic techniques and molding into PDMS. The dimensions/width of the ridges or raised surfaces on the microstamp corresponded to the widths of the cell non-adhesive regions, and the grooves or indentations of the microstamp correspond to the cell permissive regions (i.e., migration channels) and cell loading regions. Stated another way, the surface of the microstamp surface is inverse to the micropattern, where the grooves/indents of the microstamp will correspond to the ECM-component coating and the cell-adhesive regions and cell loading regions, and the raised surfaces (which contact the nanotextured substrate when the microstamp is placed on the surface of the nanotextured substrate) correspond to the cell non-adhesive regions.

In some embodiments, the exact spatial structure of the micropattern can be changed by altering the features of a polydimethylsiloxane (PDMS) micro stamp used for microcontact printing and/or by printing multiple times at different angles. In some embodiments, a micropatterned stamp is a PDMS master stamp. In some embodiments, a micropatterned stamp comprises an array of 2, 3, 4, 6, 8, 12, 24, 96, 384 or 1526 cell migration units compatible with a multi-well plate comprising 2, 3, 4, 6, 8, 12, 24, 96, 384 or 1526 wells, respectively, useful for patterning an array of migration units for a multiplex array. The microstamp can be configured to be used to pattern a nanotextured surface that is at the bottom surface of a microwell place, or alternatively for micropatterning a nanopatterned substrate where well dividers/walls are then affixed or otherwise secured to the substrate to generate a multi-well plate.

When the microstamp is placed on the nanotextured/nanopatterned substrate, the nanotextured substrate is prepared for plasma lithographic patterning using oxygen plasma treatment, which changes the exposed surfaces of the hydrophobic nanogroove-patterned PDMS to a hydrophilic surface. The non-exposed surfaces of the nanopatterned substrate, i.e., areas in contact with the ridges of microchanneled PDMS stamp (i.e., the microstamp) remain hydrophilic (and become the cell non-adherent regions).

Next, the ECM component coating is applied when the microstamp is still placed on the surface of the nanotextured substrate. In some embodiments, collagen type I (e.g. at about 10 µg/mL or about g/mL, or about 30 µg/mL, or about 40 µg/mL, or about 50 µg/mL, or about 60 µg/mL, or about 70 µg/mL, or about 80 µg/mL, or about 90 g/mL, or about 100 µg/mL or anywhere between 20-50 µg/mL, or 50-80 µg/mL or 10-100 µg/mL or greater than 100 µg/mL) is applied for a pre-determined period of time. In some embodiments, the ECM component coating as disclosed herein can be applied for at least 2, or at least about 3, or at least about 4, or at least about 5, or at least about 6, or at least about 7, or at least about 8, or at least about 9, or at least about 10, or at least about 12, or at least about 24, or at least about 36 or more than 36 hours, but less than 7 days.

After incubation with the ECM component coating, the microstamp can be carefully removed. The removal of PDMS microstamp results in the biomimetic culture platform with various widths of ECM-coated regions (i.e., cell adherent regions) and non-cell adherent regions, as well as cell loading region. Alternatively, cells can be plated in a cell loading region on the substrate and the microstamp removed after cells have been cultured for a predetermined time in the cell loading region and after the cells have reached monolayer.

Another method for applying the micropattern includes, for example "micro-contact printing." The term "microcontact printing" refers to the use of the relief patterns on a PDMS stamp to form patterns of self-assembled monolayers (SAMs) of an image-forming material on the surface of a thermoplastic material through conformal contact. Nanocontact printing differs from other printing methods, like inkjet printing or 3D printing, in the use of self-assembly (especially, the use of SAMs) to form micropatterns of various image-forming materials. Such methods are known in the art (Cracauer et al, U.S. Pat. No. 6,981,445; Fujihira et al, U.S. Pat. No. 6,868,786; Hall et al, U.S. Pat. No. 6,792,856; Maracas et al, U.S. Pat. No. 5,937,758).

In alternative embodiments, the micropatterning can be applied to the nanotextured substrate by a variety of methods known to one skilled in the art, such as printing, sputtering and evaporating. The term "evaporating" is intended to mean thermal evaporation, which is a physical vapor deposition method to deposit, for example, a thin film of metal on the surface of a substrate. By heating a metal in a vacuum chamber to a hot enough temperature, the vapor pressure of the metal becomes significant and the metal or deposited composition (e.g., graphene) evaporates. It recondenses on the target substrate. As used herein, the term "sputtering" is intended to mean a physical vapor deposition method where atoms in the target material are ejected into the gas phase by high energy ions and then land on the substrate to create the thin film on the surface of the substrate. Such methods are known in the art (Bowden et al. (1998) Nature (London) 393: 146-149; Bowden et al. (1999) Appl. Phys. Lett. 75: 2557-2559; Yoo et al. (2002) Adv. Mater. 14: 1383-1387; Huck et al. (2000) Langmuir 16: 3497-3501; Watanabe et al. (2004) J. Polym. Sci. Part 6: Polym. Phys. 42: 2460-2466; Volynskii et al. (2000) J. Mater. Sci. 35: 547-554; Stafford et al. (2004) Nature Mater. 3:545-550; Watanabe et al. (2005) J. Polym. Sci. Part 6: Polym. Phys. 43: 1532-1537; Lacour et al. (2003) Appl. Phys. Lett. 82: 2404-2406).

In some embodiments, the micropatterning be applied to the nanotextured substrate using "pattern transfer." The term "pattern transfer" refers to the process of contacting an image-forming device, such as a mold or stamp (i.e., microstamp), containing the desired pattern, with thermoplastic material. After releasing the mold, the pattern is transferred to thermoplastic material. In general, high aspect ratio pattern and sub-nanometer patterns have been demonstrated. Such methods are known in the art (Sakurai, et al, U.S. Pat. No. 7,412,926; Peterman, et al, U.S. Pat. No. 7,382,449; Nakamura, et al, U.S. Pat. No. 7,362,524; Tamada, U.S. Pat. No. 6,869,735).

It should be understood that given the teachings as described herein it will be possible for those of skill in the art to produce arrays that correspond to dimensions smaller or larger than those exemplified here and still produce a surface useful for the arrangement and growth of cells, e.g., tumor cells or other cell populations.

These platforms can provide a transparent biocompatible surface with specific nanoarchitectures and micropatterns that provide both direct contact cues for ansiotropically aligned cells (provided by the nanotexture) and trajectory directional cues (provided by the cell permissive regions of the cell migration units). In particular, the nanotopography as disclosed herein provides anisotropic or directional growth cues for cell migration, the micropatterning provides trajectory directional guidance cues for cell migration and thus, can recreate in vivo tissue architecture at the cellular and subcellular level in a reproducible fashion. Importantly, the data obtained with the BCPs described herein using cells from normal and transformed and aggressive tumor cells agrees well with the phenotypes of the cells in question. That is, non-transformed cells migrate slower than transformed cells, which migrate slower than aggressive or metastatic tumor cells, indicating that the migratory behavior of cells on the platform, and accurately reflect tumor phenotype, rendering the platform described herein well suited for both diagnostic/prognostic uses, as well as for screening purposes to identify agents that modulate such behavior.

(iii) Fabrication of the BCP as a Multi-Well Plate.

In some embodiments, the BCP is configured for high throughput screening (HTS). In some embodiments, the biomimetic culture platform can be fabricated in a multi-well format for multiplex analysis. This multi-well format permits the examination or analysis of multiple cell populations at once, and thus permits assessment of either different cell populations (e.g., migration of breast cancer cells from different patients, or effect of a mutation or SNP on the migration potential of a cell), or effect of a compound on a particular cell population (e.g., at inhibiting or reducing the EMT or inhibiting or reducing at least one migration property of a cell).

As the biomimetic culture platform can be configured as a multi-well format, it allows comparison of multiple different cancer cell types and/or agents in a single assay. As such, a multi-well engineered biomimetic culture platform permits rapid, simple screening of migratory behavior that can be employed for research and clinical applications, such as personalized medicine. Moreover, a multi-well array format of biomimetic culture platform is a miniaturization of a migration assay allowing complex analysis of multiple cancer populations in a HTS, requiring only ~100 cells per individual cell migration unit.

In some embodiments, the biomimetic culture platform can be fabricated with an array of cell migration units, and in some embodiments, each well of a multi-well plate comprises at least one cell migration unit, thereby forming a multiplex assay. In some embodiments, walls or well-dividers are affixed or otherwise secured to the surface of a biomimetic culture platform to form a multi-well plate comprising 2, 3, 4, 6, 8, 12, 24, 96, 384 or 1526 wells in an array of migration units for a multiplex array.

In alternative embodiments, the biomimetic culture platform (i.e., nanotextured surface with at least one cell migration unit micropattern) is generated on the bottom surface of each well of a multi-well plate, e.g., a multi-well plate comprising 2, 3, 4, 6, 8, 12, 24, 96, 384 or 1526 wells. In some embodiments, a biomimetic culture platform (i.e., nanotextured surface with at least one cell migration unit micropattern) is generated on a glass coverslip, and a coverslip is placed in each well of a multi-well plate comprising 2, 3, 4, 6, 8, 12, 24, 96, 384 or 1526 wells.

In some embodiments, the cell migration units can be present on the nanopatterned surface as a repeating unit, and can be arranged in an array. This allows comparison of the migration properties of different cell populations in a single experiment, e.g., comparison of different cell populations (e.g., from different patient samples, or one cancer cell type versus another cancer cell type, or the migration properties in the presence or absence of an agent for screening agents which inhibit migration of cancer cells etc.). In some embodiments, the array comprises 2 cell migration units, or at least 3, or at least 4, or at least 6, or at least 8, or at least 12, or at least 16, or at least 24, or at least 48, or at least 96, or at least 384, or at least 1536. In some embodiments, the array comprises a number of cell migration units compatible with a multi-well plate and/or a multi-well slide (i.e., a multiwall culture slide or a cell chamber slide). In some embodiments, each well of a multi-well plate comprises a single cell migration unit.

Additionally, a multi-well format is extremely helpful in rapidly characterizing the independent effects of both nano-topography (i.e., the nanogroove dimensions) and micropatterns (i.e., width of the migration pathways) on one or more of a cell's migration properties (e.g., migration speed, alignment, persistence). Additionally, a multi-well format could be used in patient specific assessment of migration properties of a cell population or cancer cell population. In some embodiments, the BCP can be used in mid and high-throughput screens and analysis systems.

II. Cell Populations and Cancer Cells

Any adherent cell or cell type can be assayed using the BCP as described herein to evaluate migratory behavior or potential. That is, the BCP as disclosed herein can be used to assess the invasive potential and/or migration properties of any desired cell type or cell population, including but not limited to a population comprising cancer cells. Non-transformed cells can be used as a reference or standard for comparison. However, often, the cells of interest will be cancer cells or tumor cells, including cancer stem cells. In some embodiments, a biological sample comprising a population of cancer cells or tumor cells is seeded into the cell loading region of the BCP and migration along the migration pathways assessed.

In some embodiments, the population of cells seeded into the cell loading region comprise epithelial cells. In some embodiments, the cancer cells are human cancer cells. In some embodiments, the cancer cells are cancer cells from an epithelial tissue. In some embodiments, the population of cells comprises breast cells, and/or breast cancer cells. In some embodiments, the population of cells comprises cancer stem cells. In some embodiments, the population of cells comprises human cells.

In some embodiments, the biological sample comprising a population of cancer cells can be a single cell or, for example, homogenized cancer biopsy sample. In some embodiments, the biological sample comprises cancer cells which have been cultured in vitro. In alternative embodiments, the biological sample is a portion of a biopsy sample obtained from a subject, and can be seeded or placed into the cell loading region of the BCP to assess the migration properties of cells in the cell population, e.g., of cells present in a solid tumor.

In some embodiments, a biological sample comprises a population of cancer cells, and can be selected from any or a combination of a biopsy sample, ex vivo cultivated sample, ex vivo cultivated tumor sample, surgically dissected tissue sample, a lymph fluid sample or a primary ascite sample.

The use of the BCP as described herein is contemplated with other cell populations including, for example, blood cells, skin cells, keratinocytes and fibroblasts, neurons and supporting cells such as oligodendrocyte cells, Schwann cells and the like. In some embodiments, the BCP as described herein is contemplated for use with epithelial cells or cells of epithelial tissue origin. In some embodiments, the epithelial cells are normal epithelial cells (i.e., non-cancer epithelial cells or epithelial cells from normal tissue), for example, from mammary tissue, skin, colon and the like. In some embodiments, the epithelial cells are tumor epithelial cells (i.e., cancer epithelial cells or epithelial cells from cancerous tissue), derived for example, from mammary, skin or colon tumors and the like.

In some embodiments, the BCP as disclosed herein can be used in methods to assess the invasive potential and/or migration properties of a cell population comprising cancer cells, and/or comprising cancer stem cells. Cancers to be assayed in such a manner can include, but are not limited to, bladder cancer; breast cancer; brain cancer including glioma, glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS associated leukemias and adult T-cell leukemia lymphoma; intraepithelial neoplasms including Bowen's disease and Paget's disease, liver cancer; lung cancer including small cell lung cancer (SSC) and non-small cell lung cancer; lymphomas including Hodgkin's disease and lymphocytic lymphomas; neuroblastomas; oral cancer including squamous cell carcinoma; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer, testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilm's tumor.

In some embodiments, a BCP as disclosed herein can be used in methods to profile multiple samples isolated from patients with breast cancer (e.g., after a breast biopsy or mastectomy), prostate cancer (e.g., tumor samples from prostatectomy), as well as brain and bone cancers, or melanoma. In an alternative embodiment, the BCP as disclosed herein can be used in methods to assess the invasive potential and/or migration properties of a population of cells which do not comprise glioma and/or brain cancer cells.

In one embodiment, a BCP as disclosed herein can be used in methods to assess if a subject from whom the cell population was obtained is at risk of having a metastasis or malignant cancer, the method comprising assessing the migration properties of cells obtained from the subject according to the methods disclosed herein, and if one or more of the migration properties (e.g., migration speed, alignment and persistence) are above a pre-determined reference threshold level, the subject is identified as being at risk of having a metastasis or a malignant cancer. In some embodiments, the reference threshold level is based on the cell migration properties of a non-metastatic cancer or a control cell line (e.g., fibroblast cells), or cells from a normal tissue sample, where the tissue sample is from a tissue matched, species matched and optionally, age matched biological sample. In some embodiments, the reference level is from a non-malignant, matched tissue sample. In some embodiments, the reference level is a reference sample from a non-malignant tumor tissue sample.

III. Method of Assessing Migration Properties of a Population of Cells.

As disclosed herein, the biomimetic culture platform can be used to assess one or more migration cell properties, e.g., selected from alignment (i.e., anisotropy), migration speed and persistence. The biomimetic culture platform described herein provides, at a basic level, a method of measuring the migration or migration potential of a cell. In this methods, cells are seeded into the cell loading region of a cell migration unit in the array, cultured for a predetermined period of time (e.g., to permit monolayer formation at or near confluence), and at a selected start point, the cells are allowed to migrate along the migration pathways for a selected or predetermined period of time, after which the distance traveled and alignment of the cells assessed. The combination of nanoscale and microscale cues provided by the biomimetic culture platform provide an environment in which cell migration behavior reflects the migratory potential or migratory activity of the same cells in vivo—that is, the migratory activity of the tumor cells in the assay described herein reflects metastatic potential or activity of the tumor cells.

The biomimetic culture platform as disclosed herein can be used in a method for measuring the invasive potential and/or migration properties of a population of cancer cells. In some embodiments, the migration properties of a plurality of different populations of cancer cells can be assayed at one time, allowing for a high-capacity and high-throughput migration assay. In such embodiments, a biological sample comprising a population of cells is in the cell loading region of the BCP, followed by measurement of the cell migratory behavior. In general, cells that exhibit greater migratory activity under these conditions have more invasive potential than those with less migratory activity. A tumor with greater invasive potential or activity in this assay is more likely to reoccur after resection or other cancer treatment.

In some embodiments, the methods for performing a high-capacity migration assay as disclosed herein can be automated, e.g., using a robotics system. Advantages of the biomimetic culture platform assay and the methods of using it include that they can be performed rapidly, with high-capacity and on a cost effective basis without having to wait for a metastasis to occur in the subject. The assay and methods as disclosed herein are efficient, in that an investigator can readily compare a variety of different populations of cancer cells from one or more tumor sites in one or more subjects, and can compare behavior to cancer cells with known metastatic potential and invasive capacity. The biomimetic culture platform in the methods as disclosed herein can be conducted economically, as they require relatively few cells and therefore minimal amounts of media and agents to be tested. Furthermore, by selecting a variety of reference cancer cell populations (e.g. having a defined or known degree of metastatic potential or invasive capacity or a preference for a specific site of metastasis), the method can be used to identify the degree of metastatic potential and invasive capacity of a large number of cancer cell populations at one time. In some embodiments, the biomimetic culture platform assay as disclosed herein can also be used in screens to identify anti-metastatic agents which affect different stages of metastasis, and/or which are directed against metastases to particular tissues, or to identify agents which inhibit or reduce at least one migration property and/or the EMT of a population of cells, including tumor cells.

A cell population, e.g., a cancer cell population as described herein can be seeded onto the cell loading region of each cell migration unit in an array on a BCP as described herein. This is generally accomplished by simply adding as suspension of the cells to the cell loading region in each well of a multi-well plate comprising the BCP, generally with an appropriate tissue culture medium. In some embodiments, the cancer cells are cultured in the cell loading region for a pre-determined time prior to the beginning of the assay (i.e., before being allowed to migrate along the migration pathways). In such embodiments, the cells can be cultured in the cell loading region for a pre-defined period of time, for example, for at least about 1 hour, or at least about 2 hours, or at least about 6 hours, or at least about 12 hours, or at least about 24 hours, or at least about 48 hours, or at least about 3 days, or at least about 5 days, or at least about 7 days, or at least about 14 days, or any time between 1-48 hours, or between about 3-14 days. Timing will depend, for example, on the density of seeding and plating efficiency, but it is preferred that the cells are at, or near confluence when cell migration down the migration pathway is permitted.

In some embodiments, the cells are seeded in a matrix (e.g., matrigel or the like) and cultured to reach confluence, and then media applied to the surface of the BCP to start the assay and allow the cells to migrate along the migration pathway. In alternative embodiments, when the cells are seeded in the cell loading region, there is a cell impermeable barrier between the cell loading region and the beginning (proximal end) of the migration pathway, preventing the cells from entering the migration pathway. When the cell impermeable barrier is removed (i.e. at the start of the migration assay), cells can begin to migrate along the migration pathway.

In some embodiments, the cells are allowed to migrate along the migration pathway for a selected, or pre-defined period of time, e.g., any of 20 mins, 30 mins, 1, 2, 3, 6, 8, 10, 12, 24, 36, 48 hours, or more than 48 hours, or any appropriate time period between 20 mins and 48 hours. The pre-determined incubation time to allow migration of the cells along the migration pathway can be determined by one of ordinary skill in the art to allow the cancer cells to migrate to one or more migration pathways. In some embodiments, the pre-determined period of time is between 2-6 hours, or between 6-12 hours, or between 12-24 hours, or between 24-48 hours, or between 48-36 hours or more than 36 hours. In some embodiments, the pre-determined period incubation time is at least about 2 hours, or at least about 4 hours, or at least about 6 hours, or at least about 12 hours, or at least about 24 hours, or at least about 48 hours, or at least about 3 days, or at least about 5 days, or at least about 7 days, or at least about 14 days, or any time between about 2-48 hours, or between 3-5 days, or between about 3-14 days. In some embodiments, a BCP migration assay can be incubated for about 24 hours, or about 2 days, or about 3 days or about 4 days or about 5 days.

In some embodiments, after a pre-determined period of time, the distance the cells have migrated is determined by time-lapse images taken at desired intervals, providing a series of images during the selected period of time. In some embodiments, for example, images are taken at approximately 20-minute intervals, or any number between 1 minute and 48 hour intervals; wherein the series of images are e.g., 10-36 images during 8-16 hours in culture, 36-300 images during 24 hours in culture, or any desired regular or irregular capture of images during any desired culture period.

In alternative embodiments, the cells that have migrated along the migration pathways are analyzed and quantified, using cell proliferation reagents (e.g., Alamar Blue) or fluorimetric assays (e.g., calcein stain). Alternatively, in some embodiments, cells in each migration pathway can be fixed and quantified with fluorescent labeling agents (e.g. SYTOX to label DNA, Phalloidine to label F-actin) and visualized and analyzed using any conventional method (fluorescent microscope, fluorescent or luminescence scanner, phosphorimager, gel imager, colorimetric imaging etc.).

After the cells have been allowed to migrate after a predetermined time period, the migration distance of at least one individual cell, or a number of cells is measured. The migration distance is used to calculate migration speed, e.g., µm/hr, and persistence (min) of an individual cell or population of cells in the pre-determined time period.

In some embodiments, a population of cancer cells that have migrated furthest along a migration pathway in the pre-determined period of time are collected, for example, a population of cancer cells located in the distal one-third (33%), or distal ¼ (25%), or distal ⅙ (16%), or distal ⅛ (12%) or distal ⅒ (10%) of the migration pathway are collected. It is contemplated that such a collected population of cells will comprise cancer stem cells. In some embodiments, these cells are an isolated population of cells (i.e., an isolated cell population) from the heterogeneous population that was seeded in the cell loading region. In some embodiments, the collected population of cells are cultured and cells expressing stem cell markers are collected and analyzed.

In some embodiments, the BCP can be used to collect migrated cells. For example, the inventors have demonstrated that higher contractile forces and anisotropic stiffness of metastatic cancer cells have been discovered to promote the progression of cancer malignancy (data not shown). In some embodiments, the biomimetic culture platform can be used in a Rapid Analysis of Cell Migration Enhancement (RACE) method, where cells which have migrated to a specific portion of the migratory pathway (e.g., distal ⅓rd or less) are collected and analyzed, or alternatively cultured and re-seeded on another biomimetic culture platform, and the process repeated. In some embodiments, such a procedure can be used to identify highly migratory cancer cells, and in some instances, cancer stem cells.

In some embodiments, gene expression analysis is performed on the population of cells collected from each well of the array. The level of gene expression of cells can be analyzed, for example, using standard assays known in the art, e.g., Northern analysis, ribonuclease protection assays, or reverse transcription-polymerase chain reaction (RT-PCR) (see, e.g., Sambrook et al., Molecular Cloning: A Laboratory Manual (3rd ed. 2001)). Given the small number of cells, gene expression is perhaps most readily analyzed via RT-PCR or by quantitative RT-PCR (QRT-PCR) methods. The isolated cells can optionally be expanded for one or more generations to facilitate analysis.

Changes in gene expression can be assayed using known genome-wide analysis techniques. For example, an Affymetrix GeneChip® can be used to perform transcriptome analysis; Illumina Deep Sequencing can be used to perform the analysis of coding and regulatory RNAs (e.g. micro RNA or miRNA). Gene expression and regulatory RNA profiles can be compared to known profiles for cells grown ex vivo and in vivo. In some embodiments, expression profiling and flow cytometry analysis of the migrated or collected cells can be used to characterize the migrated cells differentiation state.

The collected cells, or cells expanded from them in culture, can also be used to analyze protein levels, by methods such as by Western analysis or other immunoassays. Proteins, carbohydrates and metabolites from the cellular material can be analyzed by known global profiling methods such as those based on mass spectrometry (e.g. shotgun proteomics, metabolomics) or NMR spectroscopy. In some embodiments, protein expression can be measured by a method selected from the group consisting of: immunoblot analysis; immunohistochemical analysis; ELISA, isoform-specific chemical or enzymatic cleavage; protein array and mass spectrometry. In some embodiments, protein expression can be measured by contacting the biological sample with at least one protein binding agent selected from the group consisting of: antibodies; recombinant antibodies, chimeric antibodies, tribodies, midibodies, small molecules, recombinant proteins, peptides, aptamers, avimers and derivatives or fragments thereof.

In some embodiments, cells can be enzymatically removed from the migration pathways, or alternatively thermodynamically removed, as disclosed herein using a thermoresponsive material layer on the distal portion of the substrate (e.g., at the distal one-third (33%), or distal ¼ (25%), or distal ⅙ (16%), or distal ⅛ (12%) or distal 1/10 (10%) of the substrate).

In some embodiments, the number of cells collected can be characterized using standard cytometry assays, e.g., by flow-cytometry analysis, hemocytometer, automated cell counter etc. Such flow-cytometry methods are useful where it is desirable to assess the number of live, apoptotic, and necrotic cells and to perform cell cycle analysis of the cell population in a migration pathway. In some embodiments, fluorescent reporters or cell tracer dyes can be used to label the cells in each migration pathway and/or to trace the origin of each migrated cell. For example, in some embodiments, cancer cells in a biological sample can be labeled with a fluorescent marker, e.g., a fluorescent labeled antibody to a specific cell-surface marker, to characterize and trace the migration of specific cell types into the migration pathways.

In some embodiments, a comparative transcriptome profiling of the cancer cells collected from the migration pathways can provide novel insight on transformations that occur to cancer cells during migration. For example, the inventors surprisingly discovered herein that cells that migrated furthest along the migration pathway increased their speed of migration the further they migrated along the migration pathway during the pre-defined time period. For example, an initial migration speed when cells first enter the proximal end of the migration pathway can be affected, e.g., by a forward pressure or force from the cells behind it, yet once a cell is freely able to migrate using the contact guidance cues of the nanogrooves, the migration speed increases to the optimal speed for that cell type. Analysis of gene expression changes during this process can provide new targets for modifying migratory/invasive behavior.

Certain embodiments will employ conventional techniques of molecular biology (including recombinant techniques), microbiology, cell biology, biochemistry, and immunology, which are known to those of ordinary skill of the art. Such techniques are described in, e.g., "Molecular Cloning: A Laboratory Manual", third edition (Sambrook et al, 2001); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

In some embodiments, the number or proportion of cells that have migrated in each migration pathway can be automatically determined using automated analysis software, which can optionally include data analysis of the number of cells that have migrated a particular distance of the migration pathway (i.e., number of cells that have migrated 1%, or 5% or 10% the distance of the migration pathway, or have migrated at least 10 µm, or at least 20 µm, or at least 30 µm, or at least 40 µm, or at least 50 µm, or at least 60 µm, or at least 70 µm, or at least 80 µm, or at least 90 µm, or at least 100 µm towards the distal end of the migration pathway in a pre-defined period, e.g., 10 mins, or at least 30 mins, or at least 1 hour, or least about 2 hours, or at least about 4 hours, or at least about 6 hours, or at least about 12 hours, or at least about 24 hours, or at least about 48 hours, or at least about 3 days, or at least about 5 days, or at least about 7 days or more than 7 days.

IV. Determining Metastatic Potential of Cancer Cells.

As described herein, another aspect of the technology described herein relates to use of the biomimetic culture platform in a method for prognosis of aggressive cancer, for example, to assess the migratory behavior of a tumor sample (e.g., tumor biopsy) obtained from a subject with cancer.

In some embodiments, if the migration speed of the tumor cells in the sample is above a certain threshold, e.g., at least 0.5-fold faster than control/non-metastasis cancer cell; or e.g., if the cells have a migration speed of at least 20 µm/hr, the tumor cells are identified to have a high migratory potential and the subject is identified as having an aggressive or metastatic cancer. Such a subject may have a poor prognosis and is selected for a more aggressive cancer treatment as compared to a subject whom has a tumor where the cells migrate at speed of, e.g., less than 20 µm/hr.

Another aspect of the technology described herein relates to use of the biomimetic culture platform in a method for determining cell heterogeneity in a population of tumor cells, such as, tumor cells obtained from a subject. In some embodiments, the biomimetic culture platform can be used to determine is a subject has tumor comprising a high proportion of migratory cancer cells, and therefore has an aggressive cancer, and/or a heightened risk of cancer reoccurrence.

As disclosed herein, the technology described herein provides methods to assess the metastatic potential of a population of cancer cells using the biomimetic culture platform in an assay as disclosed herein. After incubation of cells in the cell migration units of the BCP for a predetermined period of time, the migration of cells along each migration pathway is quantified. This can be measuring the distance that individual cells, or a population of cells, or a % of the total cell population seeded into the cell loading region have travelled along a migration pathway by any of the methods described above to determine the migration of the cells from the cell loading region.

Typically, one or more of the migration properties are assessed selected from alignment (e.g., anisotropy), migration speed and/or persistence. The amount of migration of the cancer cells from the cell loading region (or in a defined section of the migration pathway, i.e., distal ⅓ of the migration pathway) is a function of (e.g., proportional to) the metastatic potential (ability, activity, capacity) of the cell. The distance of cancer cell migration into one or more migration pathways, or into a defined section of the migration pathway (e.g., the distal ⅓ of the migration pathway) during a pre-defined time period can be determined using image capture technology, or measuring the number of cells present, e.g., using imaging (e.g., detection of a fluorescent marker or luciferase) or other quantitative methods such as gene expression analysis as described herein or known in the art.

Migration properties and invasive potential of a cancer cell population can be determined a variety of different ways using a variety of different parameters measurable with the BCPs described herein. Exemplary methods to determine the invasive potential of a cancer cell population are disclosed herein; however, other calculations are encompassed in the technology described herein. Examples of evaluations involving measurement of alignment/anisotropy, migration speed and persistence in a predefined period of time are provided and discussed in further detail below (see, e.g., FIGS. 3C and 5D and 5E-5F).

In some embodiments, a migration speed of a population of cells in a pre-determined time period which is above a predetermined level of accidental migration (or random walk) indicates that the cancer cell population comprises a population of metastatic cancer cells, i.e., cancer cells with invasive properties. In some embodiments, if the migration speed of the tumor cells in the sample is above a certain threshold, e.g., at least 0.5-fold faster than control/non-metastasis cancer cell; or e.g. has a migration speed of at least 20 μm/hr on a 120 μm width migration pathway, the cancer cell population is identified to have a high migratory potential and comprises cancer cells with an invasive and/or metastatic potential. In such embodiments, a subject is identified as having an aggressive or metastatic cancer.

In some embodiments, if a cell population has a migration speed of at least 25 μm/hr on a migration pathway with a width between 30 μm-80 μm, or a migration speed of at least 30 μm/hr on a 30 μm width migration pathway, the cancer cell population is identified to have a high migratory potential and comprises cancer cells with an invasive and/or metastatic potential. In such embodiments, a subject is identified as having an aggressive or metastatic cancer. In some embodiments, the subject may have a poor prognosis and is selected for a more aggressive cancer treatment as compared to a subject whom has a tumor where the cells migrate at a speed of, e.g., less than 20 μm/hr (on a 120 μm width migration pathway), or less than 25 μm/hr (on a 30-80 μm width migration pathway), or less than 30 μm/hr (on a 30 μm width migration pathway).

In some embodiments, a population of cells that has a persistence time of equal to, or more than 100 min in a pre-determined time period, or which is above a predetermined level of accidental migration (or random walk) indicates that the cancer cell population comprises a population of metastatic cancer cells and cancer cells with invasive population. In some embodiments, if the persistence time of the population of cancer cells in the sample is above a certain threshold, e.g., at least 0.5-fold higher than control/non-metastasis cancer cell; or e.g. has a persistence time of at least 100 min on a 120 μm width migration pathway, the cancer cell population is identified to have a high migratory potential and comprises cancer cells with an invasive and/or metastatic potential. In some embodiments, if the persistence time of the population of cancer cells in the sample is above a certain threshold, e.g., at least 0.5-fold higher than control/non-metastasis cancer cell; or e.g. has a persistence time of at least 200 min on a 80 μm width migration pathway, the cancer cell population is identified to have a high migratory potential and comprises cancer cells with an invasive and/or metastatic potential. In some embodiments, if the persistence time of the population of cancer cells in the sample is above a certain threshold, e.g., at least 0.5-fold higher than control/non-metastasis cancer cell; or e.g. has a persistence time of at least 300 min on a 60 μm width migration pathway, the cancer cell population is identified to have a high migratory potential and comprises cancer cells with an invasive and/or metastatic potential. In some embodiments, if the persistence time of the population of cancer cells in the sample is above a certain threshold, e.g., at least 0.5-fold higher than control/non-metastasis cancer cell; or e.g. has a persistence time of at least 400 min on a 30 μm width migration pathway, the cancer cell population is identified to have a high migratory potential and comprises cancer cells with an invasive and/or metastatic potential. In such embodiments, a subject is identified as having an aggressive or metastatic cancer. In some embodiments, the subject may have a poor prognosis and is selected for a more aggressive cancer treatment as compared to a subject whom has a tumor where the cells have a persistence time of, e.g., less than 100 min on 120 μm with migration pathway, or less than 200 min on a 80 μm width migration pathway, or less than 300 min on a 60 μm width migration pathway, or less than 400 min on a 30 μm width migration pathway.

In some embodiments, the number of cells present in the distal ⅓ of the migration pathway in a pre-defined time period is also a measure of migration potential. In such embodiment, the presence of cells in the distal ⅓ of a migration pathway which is above a predetermined level of accidental migration indicates the cancer cell population comprises a population of metastatic cancer cells and cancer cells with invasive properties.

As described herein, another aspect of the technology described herein relates to use of the biomimetic culture platform in a method for determining cell heterogeneity in a population of tumor cells, e.g., tumor cells obtained from a subject. In some embodiments, the biomimetic culture platform can be used to determine if a subject has tumor comprising a high proportion of migratory cancer cells, and therefore has an aggressive cancer, and/or a risk of cancer reoccurrence. In such an embodiment, a representative calculation to determine the heterogeneity of a cell population, and in effect, the metastatic potential of a population of cancer cells can be based on % of the population of cells from the total cell population that migrate along the migration pathway from the cell loading region.

In such an embodiment, a cell loading region can be seeded with a predefined number of cancer cells (e.g., total starting population) and the cells permitted to migrate. After a predefined time of migration, the number of cells in a defined portion of the migration pathway, e.g., distal $⅓^{rd}$ (e.g., the migrated population) can be calculated as a % of the total starting population of cancer cells in the cell loading region. In some embodiments, the % of cells which have migrated to the defined region of the migration pathway (e.g., distal ⅓ of the migration pathway) (% migrated cells) is a measure of the invasive capacity of the cancer cell population and is predictive of the metastatic potential of the cancer cell population. In some embodiments, where at least about 5%, or at least about 10% or more than 10% of the total cell population has migrated to the distal ⅓ of the migration pathway, it indicates the population of cells has cancer cells with invasive capacity and is predictive of the metastatic potential of the cancer cell population. Nonetheless, in general, the greater the proportion of the population exhibiting strong migratory behavior, the more aggressive the tumor from which the cells were taken.

To illustrate, if the % of migrated cells reaching a defined portion of the migration pathway in a given time ranges between 0-4% migrated cells, it indicates a negligible invasive capacity and very low risk of the cell population comprising metastatic cancer cells, whereas a 5-10% range of migrated cells indicates a low level invasive capacity and low risk of the cell population comprising metastatic cancer cells, whereas an 11-20% range of migrated cells indicates a medium level invasive capacity and medium risk of the cell population comprising metastatic cancer cells, and where a % migrated cells above 20% indicates a high level invasive capacity and high risk of the cell population comprising metastatic cancer cells and predicts the cancer is a metastatic cancer.

One of ordinary skill in the art can determine the time and selected distance to best gauge or assess the cell population migratory behavior and can employ, if necessary or desired, cancer cells of known degrees of aggressiveness to help establish threshold for migratory behavior indicative of a particular level of metastatic potential. The number of migrated cells reaching a given area depends on the number of hours or days over which migration occurs. As but one illustration, for a given migration distance, in some embodiments, a migration of 11-20% of cells over a 3-5 day migration period can indicate a medium level invasive capacity and medium risk of the cell population comprising metastatic cancer cells, whereas a migration of above 20% of cells over a 3-5 day period can indicate a high level invasive capacity and high risk of the cell population comprising metastatic cancer cells and predicts the cancer is a metastatic cancer. In this example, a less than 11% migration of cells over a 3-5 day period can indicate that the cells are non-invasive cells, and have a low to negligible risk of the cells comprising metastatic cancer cells.

To illustrate this further, in some embodiments, a migration of <5-10% of cells, e.g., between about 5-10%, or about 5%, or about 6%, or about 7%, or about 8% or about 9%, or about 10%, over a time period of 1-2.9 days migration period indicates a medium level invasive capacity and medium risk of the cell population comprising metastatic cancer cells, whereas a migration of above 10% of cells over a time period of 1-2.9 day period indicates a high level invasive capacity and high risk of the cell population comprising metastatic cancer cells and predicts the cancer is a metastatic cancer. In such embodiments, a less than 10% migration of cells over a 1-2.9 day period indicates that the cells are non-invasive cells, and have a low to negligible risk of the cells comprising metastatic cancer cells.

In further embodiments, the amount of cells measured in the cell loading region after a predetermined incubation period (e.g., the non-migrating population) can also be compared to the amount of cells present in the migration pathways (e.g., a comparison of the total starting population of cells and/or a predetermined number of cancer cells with the number of cells in the cell loading region post-migration). In some embodiments, a decrease of about 5%, or about 10%, or about 20% of cells, or a decrease of more than 20%, of cells in the cell loading region post-migration (or after the defined time period) as compared to the total starting population of cells (e.g., a the predetermined number of cells loaded in the cell loading region) is indicative that the population of cancer cells comprises cancer cells with invasive capacity and is predictive of the metastatic potential of the cancer cell population.

In some embodiments, where a decrease of about 0-4% of cells in the cell loading region (as compared to the total starting population in the cell loading region at the beginning of the assay) indicates a negligible invasive capacity and very low risk of the cell population comprising metastatic cancer cells, whereas a 5-10% decrease of cells in the cell loading region indicates a low level invasive capacity and low risk of the cell population comprising metastatic cancer cells, whereas an 11-20% decrease of cells in the cell loading region indicates a medium level invasive capacity and medium risk of the cell population comprising metastatic cancer cells, and where a decrease greater than 20% of cells in the cell loading region indicates a high level invasive capacity and high risk of the cell population comprising metastatic cancer cells and predicts the cancer is a metastatic cancer.

It is envisioned that in some embodiments, where the amount of cells measured on the cell loading region prior to the pre-defined time period (e.g., total starting population) is compared to the amount of cells remaining after the pre-defined period, (e.g., the non-migrating population), or the amount of cells measured in the migration pathways (e.g., the migrated population), that cell proliferation of the cells on the BCP (either in the cell loading region or in the migration pathways) that occurs during the incubation period should be taken into account and factored into the calculation, and/or adequate controls established to measure such proliferation.

In another embodiment, a representative calculation to determine the metastatic potential of a population of cancer cells can be based on % of migration as compared to a reference cancer cell line. In some embodiments, a reference cancer cell line is a cancer cell line of known metastatic potential and invasive capacity. In some embodiments, a positive reference cancer cell line is a highly-metastatic cancer cell line, for example but not limited to, a breast cancer cell line such as MDA-MB-231, or a prostate cancer cell line such as highly invasive PC-3 and DU-154 metastatic cancer cell lines isolated from bone and brain metastases. Other highly metastatic reference cell lines can also be used, for example, LM2, HeLa cells, known carcinoma and sarcoma cell lines, lung adenocarcinoma line Anip 973, breast cancer cell lines MDA-MB-468 and MDA-MB-435, human glioblastoma line 324 and mouse melanoma B16 among others. In some embodiments, a positive reference cancer cell line is a low-metastatic cancer cell line, including but not limited to, the weakly invasive cancer cell lines LNCaP and CWR-22. In some embodiments, a reference cell line is a negative reference cell line, such as a normal cell line, for example but not limited to, normal prostate epithelial cells (RWPE-1) and fibroblasts (HIN 3T3).

In another embodiment, because cell migratory behavior on the BCP's described herein faithfully reflects the in vivo migratory/metastatic potential, a representative calculation to determine the metastatic potential of a test population of cancer cells can be based on measuring the migration properties of cells on a BCP, and comparing the migration properties with a reference cell population on the BCP, where the % of cells that migrated to a defined portion of the migration pathway (e.g., the distal $\frac{1}{3}^{rd}$) can be used as a baseline for the level of metastatic potential and invasive capacity. Accordingly, in such embodiments both positive and/or negative reference cell populations can serve as internal controls on the receiving substrate as a measure of a cancer cells invasive capacity.

To illustrate, assume that that the migration speed of a positive, highly-metastatic reference cancer cell population is set to an arbitrary value of 10, and the migration speed of negative reference cell population is set to an arbitrary value of 0, which establishes a scale, or an "invasive scale" for an invasive potential of a cancer cell line. Accordingly, the migration speed of a test population on a BCP of the same nano- and micropatterned cell migration unit dimensions can be directly compared to the migration speed from a positive reference cell line and/or optionally from a negative reference cell line. In some embodiments, a positive reference cell population of a low-metastatic cell line can be used to establish a scale of invasive potential of a cancer cell population. A comparison of the migration speed of cancer cells of the test cancer cell population with the migration speed of positive reference cell line (e.g., a highly-invasive population or a low-invasive population) and/or the migration speed a negative cell line (e.g., a non-migrating population) can be used to determine the level of invasive potential of a test cancer cell population.

For example, where the migration speed of the test cancer cell population is greater than the migration speed from the positive reference cell population, the test cell population will have an arbitrary value of greater than 10, and will be indicative of a highly metastatic cancer cell population. Similarly, where the migration speed of the test cancer cell population is less than the migration speed of cells from the (highly-metastatic) positive reference cell population, but more than the migration speed of cells from the negative reference cell population, the test cancer cell population will have an arbitrary value of greater than 0 but less than 10, and will be indicative of a metastatic cancer cell population. In some embodiments, the migration speed of the test cancer cell population can be compared to the migration speed from a low-metastatic positive reference cell population and scaled accordingly.

In some embodiments, the migration speed of the test cancer cell population can be compared as a % (or fold increase or decrease) of the migration speed of a positive (both highly-metastatic and/or low-metastatic) reference cell population and/or a % (or fold-increase) of the migration speed of a negative reference cell population. For example, where the migration speed of the test cell population is at least about 20%, or at least about 30%, or at least about 40% of the migration speed of highly-invasive positive reference cell line, it is indicative of a low metastatic potential and invasive capacity of the test cancer cell population, whereas where the migration speed of the test cell population is at least about 50%, or at least about 60%, or at least about 70%, or at least about 80%, or at least about 90%, or at least about 95%, or at least about 100%, or more than 100%, e.g., at least about 1.2-fold, or about 1.5-fold or 2-fold, or 3-fold or more than 3-fold the migration speed of a highly-invasive positive reference cell line, it is indicative of a high metastatic potential and high invasive capacity of the test cancer cell population.

Additionally in some embodiments, a negative reference cell population (e.g., a negative control) can be a positive reference cell line (e.g., a highly-metastatic and/or low-metastatic reference cell population) which has been combined (or cultured in the presence) with an inhibitor of actin-based motility. Such inhibitors of actin-based mobility are known in the art, and include for example, cytoclasin D and the like. Other negative controls also include the test population of cancer cells combined with an inhibitor of actin-based motility.

In some embodiments, one can use other calculations, such as, but not limited to, % of cancer cells with a specific marker that migrated into a specific portion of the migration pathway (e.g., distal ⅓ of the pathway); distance of total migration in predefined time period, persistence and/or orientation of cells or cells that have specific geometry.

V. Use of the Biomimetic Culture Platform in Screening Methods.

Other aspects of the technology described herein relates to the use of the biomimetic culture platform to screen for agents and compounds capable of influencing, i.e., inhibiting or reducing cell migration, e.g., reducing any one or more of speed of migration, persistence, etc., and thereby inhibiting the metastatic potential of a cancer cell population. The methods, compositions and assays comprising a biomimetic culture platform assay as disclosed herein provides a highly sensitive assay system capable of mimicking the in vivo tumor environment and the extracellular matrix (ECM).

The BCP comprising nanoscale and microscale cues for cell migration has been found to promote the epithelial-to-mesenchymal transition (EMT) in certain cell populations. This provides an approach to examine the events of the transition and to identify agents that modify or inhibit the transition. Thus, in another aspect, the biomimetic culture platform can be used in a method to screen for agents and compounds capable of inhibiting or reducing the EMT (epithelial-to-mesenchymal transition) which occurs as tumor cells acquire the capacity for metastasis. In some embodiments, cells can be monitored on a BCP for evidence of the EMT in the presence and absence of a candidate agent, to select an agent that modifies the transition. In some embodiments, EMT transition can be assessed using markers, such as vimentin (marker of mesenchymal cells) and cadherin (marker of epithelial cells). For example, cadherin is present (expressed) in normal epithelial cells and vimentin is essentially not. After EMT, or as part of the EMT process, cadherin expression levels decrease and vimentin expression levels increase. Therefore, an agent which allows cells to maintain the same level of cadherin expression and/or prevents a downregulation of cadherin and/or prevents an upregulation of vimentin expression levels is identified as a candidate agent that reduces or inhibits EMT.

As discussed above, the biomimetic culture platform as disclosed herein can be used in a screening method to identify candidate agents for inhibiting migration and/or inhibiting EMT of tumor cells. For example, a composition comprising a BCP with a population of tumor cells can be contacted with a test agent, and the effect, if any, of the test agent on a parameter associated with migration or EMT is determined. Such parameters can also include: migration speed, persistence, alignment and/or expression of endothelial or mesenchymal markers and the like.

In some embodiments, the technology described herein relates to a method of measuring migration properties, e.g., in some instances, the distance of cell migration or migration speed, of a population of cancer cells towards the distal end of a migration pathway in a selected period of time in the presence of a test agent. The measured migration properties can be compared to the migration properties, such as, distance of cell migration of the same population of cancer cells, in the presence of different concentrations of the test agent, and/or the presence of an agent known to inhibit cell migration (e.g., positive control), and/or the presence of an agent known to promote cell migration (e.g., negative control).

Other aspects of the technology described herein relate to the use of the biomimetic culture platform as disclosed herein as a research tool, e.g., to isolate tumor cells that have a high migratory potential, e.g., that have a higher migratory speed and/or persistence as compared to other cancer cells, and in some embodiments, to isolate cancer stem cells. This can be, for example, an iterative process which cells with a high migratory capacity are isolated, and optionally expanded, and re-plated on a BCP before again isolating the most rapidly migrating cells.

In some embodiments, migration properties in the presence of a test agent are compared relative to the cell migration properties of a population of cells that do not migrate (e.g., negative/non-migratory control cells), and/or to the cell migration properties of a population of cells known to migrate (e.g., positive migratory/invasive control cells/metastatic cells) in the absence of the test agent.

Another aspect of the technology described herein relates to use of the biomimetic culture platform in a method for prognosis of aggressive cancer, for example, to assess the migratory behavior of a tumor sample (e.g., a biological sample comprising a tumor biopsy) obtained from a subject with cancer, and where the migration speed of the tumor cells in the sample is above a certain threshold, e.g., at least 0.5-fold faster than control/non-metastasis cancer cell; or e.g. having a migration speed of at least 20 μm/hr, the tumor cells are identified to have a high migratory potential and the subject is identified as having an aggressive or metastatic cancer.

Another aspect of the technology described herein relates to use of the biomimetic culture platform in a method for determining cell heterogeneity in a population of tumor cells, such as, e.g., tumor cells obtained from a subject. In some embodiments, the biomimetic culture platform can be used to determine is a subject has tumor comprising a high proportion of migratory cancer cells, and therefore has an aggressive cancer, and/or a risk of cancer reoccurrence Accordingly, other aspects of the technology described herein relate to the use of the biomimetic culture platform to screen for agents and compounds capable of influencing, i.e., inhibiting cell migration, e.g., reducing any one or more of speed of migration, persistence, etc., and thereby inhibiting the metastatic potential of a cancer cell population. The methods, compositions and assays comprising a biomimetic culture platform assay as disclosed herein provides a highly sensitive assay system capable of mimicking the in vivo tumor environment and the extracellular matrix (ECM).

Other aspects of the technology described herein relate to the use of the biomimetic culture platform in a method to screen for agents and compounds capable of inhibiting or reducing EMT (epithelial-to-mesenchymal transition) of tumor cells, thereby inhibiting the metastatic potential of a cancer cell population.

Other aspects of the technology described herein relate to the use of the biomimetic culture platform as disclosed herein as a research tool, e.g., to isolate tumor cells that have a high migratory potential, e.g., that have a higher migratory speed and/or persistence as compared to other cancer cells, and in some embodiments, to isolate cancer stem cells.

In some embodiments, the population of cells are obtained from a subject with cancer, e.g., breast cancer or cancer of epithelial origin.

By way of example only, a drug screening method could be as follows: A 96 (8×12) multi-well plate, with each well comprising a cell migration unit can be used. 8 different cancer cell populations can be assessed, and 12 drugs can be tested on each cancer cell population. As each person is different, not all drugs will have the same effects on inhibiting or reducing cancer migration and/or EMT. Such a platform will allow the screening of drugs in a diverse cancer cell population. Alternatively, each well can comprise the same cancer cell population and the migration properties of the cells in the presence of 96 different drugs (including some +ve and −ve/no agent controls) be assessed.

The development of a novel "off-the-shelf" migration assay using the BCP as disclosed herein for a simple, efficient high throughput drug screening would have wide applicability both for safety testing and for the identification of new therapeutic compounds.

Another aspect of the technology described herein relates to methods to screen for agents, for example any entity or chemical molecule or gene product, which affects (e.g. increase or decrease) the migration of a cancer cell population in the presence of the agent as compared to a control agent, or the absence of an agent. In such an embodiment, an agent which increases or decreases a migration property as disclosed herein can affect the metastatic potential of a cancer cell population.

In some embodiments, any agent which decreases the migration speed, or persistence of a population of cancer cells by a statistically significant amount, or by at least about 10% as compared to in the absence of an agent, is identified to have decreased migration of the cancer cell population. If an agent decreases the migration speed, or persistence by at least about 10% or by at least about 15% or at least about 20% or at least about 30%, or least about 40% or at least about 50% or more than 50% as compared to the migration speed, or persistence in the absence of the agent, it is identified to have modulated/decreased the migration of the cancer cell population.

In alternative embodiments, the BCP can be used in a method to screen for genetic variants and mutations which affects (e.g. increase or decrease) the migration of a cell population. For example, random mutagenesis, or cells that have been genetically modified to have a particular mutation and/or polymorphism, can be used to identify genetic modifications that specifically alter the migration potential of cells, including but not limited to cancer cells or cancer stem cells, and lead to a more aggressive cancer phenotype. For example, any genetic variation which increases the migration speed, or persistence of the cell population by a statistically significant amount, or by at least about 10% as compared to when the mutation is lacking, is identified to have a positive influence on migration of the cell population. If a cell carrying a specific genetic variant increases the migration speed, or persistence by at least about 10% or by at least about 15% or at least about 20% or at least about 30%, or least about 40% or at least about 50% or more than 50% as compared to the migration speed, or persistence of the cell in the absence of the genetic variation, the genetic variant is identified to have a positive influence on (i.e., increase) the migratory potential of a population of cells. The protein or pathway(s) affected by such variant are thus identified as potential targets for agents that modify migratory/metastatic potential. Therefore, in some aspects, the technology described herein permits high-throughput screening of agents and genetic variants for personalized medicine and/or pharmacogenetics. Therefore, cancer cells carrying a specific genetic variant, and/or the effect of an agent can be easily assessed in a HTS using the methods and BCP as disclosed herein, and provides important information regarding the metastatic potential of the cancer cells for personalized medicine purposes.

The agent used in screening methods as disclosed herein can be selected from a chemical, small molecule, nucleic acid, nucleic acid analog, aptamer, protein or polypeptide or analogue or fragment thereof. In some embodiments, the nucleic acid is DNA or RNA, and nucleic acid analogues, for example can be PNA, pcPNA and LNA. A nucleic acid can be single- or double-stranded, and can be selected from a group comprising a nucleic acid encoding a protein of interest, oligonucleotides, PNA, etc. Such nucleic acid sequences include, but are not limited to, nucleic acid sequence encoding proteins that act as transcriptional repressors, antisense molecules, ribozymes, and small inhibitory nucleic acid sequences, including, but not limited to RNAi, shRNAi, siRNA, micro RNAi (mRNAi), etc. A protein and/or peptide agent or fragment thereof, can be any protein of interest, including, but not limited to: mutated proteins; therapeutic proteins; truncated proteins, wherein the protein is normally absent or expressed at lower levels in the cell. Proteins of interest can further include mutated proteins; genetically engineered proteins; peptides; synthetic peptides; recombinant proteins; chimeric proteins; antibodies; humanized proteins; humanized antibodies; chimeric antibodies; modified proteins and fragments thereof.

An agent can contact the cell population in the cell loading well, or in the migration pathways, by, for example, applying the agent to a medium in a multi-well plate, where each well comprises at least one cell migration unit with cell seeded thereon. Alternatively, an agent can be expressed intracellularly as a result of introduction of a nucleic acid sequence into the cell population and its transcription to result in the expression of a nucleic acid and/or protein agent within the cell. An agent as used herein also encompasses any action and/or event or environmental stimulus, e.g., as non-limiting examples, an action can comprise any action that triggers a physiological change in the cell population, including, but not limited to oxygen deprivation, ischemia, heat-shock, ionizing irradiation, cold-shock, electrical impulse (including increase or decrease in stimuli frequency and/or stimuli intensity), mechanical stretch, hypoxic conditions, light and/or wavelength exposure, UV exposure, pressure, increased and/or decreased oxygen exposure, exposure to reactive oxygen species (ROS), fluorescence exposure, etc. Environmental stimuli also include intrinsic environmental stimuli.

The exposure (e.g. contacting) of a cells to agent may be continuous or non-continuous. In some embodiments, where the exposure (e.g. contacting) of the cells to an agent is a non-continuous exposure, the exposure to one agent can be followed with the exposure to a second agent, or alternatively, by a control agent (e.g. a washing step). In some embodiments, a cell population is exposed to at least one agent, or at least 2, or at least 3, or at least 4, or at least 5, or more than 5 agents at any one time, and this exposure can be continuous or non-continuous, as discussed above.

In some embodiments, the agent is an agent of interest including known and unknown compounds that encompass numerous chemical classes, primarily organic molecules, which may include organometallic molecules, inorganic molecules, genetic sequences, etc. An important aspect of the technology described herein is to evaluate candidate drugs, including toxicity testing; and the like. Candidate agents also include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Also included as agents are pharmacologically active drugs, genetically active molecules, etc. Compounds of interest include, for example, chemotherapeutic agents, hormones or hormone antagonists, growth factors or recombinant growth factors and fragments and variants thereof. Exemplary of pharmaceutical agents suitable for the methods described herein, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

The agents include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, as well as libraries of compounds prepared for analysis; and the like. Samples of interest include compounds being assessed for potential therapeutic value, e.g. drug candidates.

Agents such as chemical compounds, including candidate agents or candidate drugs, can be obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for effect on a composition comprising the BCP and cells by adding the agent to at least one and usually a plurality of BCPs or migratory units thereof containing cells. A change in a parameter of a cell in response to the agent is measured, and the result is evaluated by comparison to a reference cell on a BCP of the same configuration. A reference composition comprising the BCP and cells can include, but is not limited to, a composition comprising the BCP and the same cells in the absence of the same agent, or the BCP and the same cells in the presence of a positive control agent, where the agent is known to cause an increase or decrease in at least one parameter of migration behavior being assessed. In alternative embodiments, a reference composition comprising a BCP and cells is a negative control, e.g. where composition comprising a BCP and cells is not exposed to an agent (e.g. there is an absence of an agent), or is exposed to an agent which is known not to have an effect on at least one migration parameter being assessed.

In some embodiments, the agents can be conveniently added in solution, or readily soluble form, to the cells cultured on the BCP. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells present on a BCP, followed by the second fluid. In a single solution method, a bolus of the test compound is added to the volume of medium on the BCP. The overall concentrations of the components of the culture medium should not change significantly with the addition of the bolus, or between the two solutions in a flow through method. In some embodiments, agent formulations do not include additional components, such as preservatives, that have a significant effect on the overall formulation. Thus, preferred formulations consist essentially of a biologically active agent and a physiologically acceptable carrier, e.g. water, ethanol, DMSO, etc. However, if an agent is a liquid without a solvent, the formulation may consist essentially of the compound itself.

A plurality of assays can be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, e.g. at zero concentration or below the level of detection of the agent or at or below the concentration of agent that does not give a detectable change in the phenotype, e.g., a change in a migratory property or characteristic of the cells.

Optionally, cells used in a screen as described herein can comprise cells which have been manipulated to express a desired gene product. Gene therapy and genetic modification can be used to either modify a cell to replace a gene product or add a heterologous gene product, or alternatively knockdown a gene product endogenous to the cell.

Where genes are introduced or modified either for screening purposes (e.g., introduction of an shRNA expressing construct) or to modify a cell, a construct can be transfected into the cell using any of a variety of techniques. Preferably, the gene is transfected into the cell using an expression vector. Suitable expression vectors include plasmid vectors, viral vectors (such as replication defective retroviral vectors, herpes virus, adenovirus, adeno-virus associated virus, and lentivirus). Non-viral delivery agents, include, e.g., liposomes or receptor ligands can also be used.

A desired gene is usually operably linked to its own promoter or to a foreign promoter which, in either case, mediates transcription of the gene product. Promoters are chosen based on their ability to drive expression in restricted or in general tissue types, for example in mesenchymal cells, or on the level of expression they promote, or how they respond to added chemicals, drugs or hormones. Other genetic regulatory sequences that alter expression of a gene may be co-transfected. In some embodiments, the host cell DNA may provide the promoter and/or additional regulatory sequences. Other elements that can enhance expression can also be included such as an enhancer or a system that results in high levels of expression.

Methods of targeting genes in mammalian cells are known to those of skill in the art (U.S. Pat. Nos. 5,830,698; 5,789,215; 5,721,367 and 5,612,205). By "targeting genes" it is meant that the entire or a portion of a gene residing in a chromosome of a cell is replaced by a heterologous nucleotide fragment. The fragment may contain primarily the targeted gene sequence with specific mutations to the gene or may contain a second gene. The second gene may be operably linked to a promoter or may be dependent for transcription on a promoter contained within the genome of the cell. In a preferred embodiment, the second gene confers resistance to a compound that is toxic to cells lacking the gene. Such genes are typically referred to as antibiotic-resistance genes. Cells containing the gene may then be selected for by culturing the cells in the presence of the toxic compound.

Methods of gene targeting in mammals are commonly used in transgenic "knockout" mice (U.S. Pat. Nos. 5,616, 491; 5,614,396). These techniques take advantage of the ability of mouse embryonic stem cells to promote homologous recombination, an event that is rare in differentiated mammalian cells. Recent advances in human embryonic stem cell culture may provide a needed component to applying the technology to human systems (Thomson; 1998).

The technology described herein is further illustrated by the following examples which in no way should be construed as being further limiting. The contents of all cited references, including literature references, issued patents, published patent applications, and co-pending patent applications, cited throughout this application are hereby expressly incorporated by reference.

The technology described herein has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

In some embodiments, the technology described herein may be defined in any of the following numbered paragraphs:

1. An array for assessing cell migration comprising: (a) nanopatterned substrate comprising parallel grooves and ridges, wherein the groove width is between 200 nm to 3000 nm, the ridge width is between 200 nm to 3000 nm, and depth of the groove is between 200 nm to 3000 nm; and (b) an array of at least one cell migration unit on the nanopatterned substrate, each cell migration unit comprising:
    i. at least one migration pathway having a proximal and distal end,
    ii. at least one cell non-adherent region having a proximal and distal end, and
    iii. at least one cell loading region;
    wherein the at least one migration pathway comprises a cell adherent surface having a width between 10 µm-500 µm, aligned parallel to the grooves and ridges,
    wherein the at least one cell non-adherent region is aligned parallel to the grooves and ridges and is adjacent to the at least one migration pathway; and wherein the at least one cell loading region is located at the proximal end of the at least one migration pathway and optionally, at the proximal end of at least one cell non-adherent region.
2. The array of paragraph 1, wherein the at least one migration pathway is coated with an extracellular matrix (ECM) component coating.
3. The array of paragraph 2, wherein the ECM component coating is collagen.
4. The array of paragraph 2, wherein the ECM component coating is not laminin.
5. The array of paragraph 2, wherein the ECM component coating further comprises at least one growth factor or chemotaxis agent.
6. The array of paragraph 1, wherein the cell migration unit comprises n migration pathways, n cell non-adherent regions, and at least one cell loading region located at the proximal end of the n migration pathways and n cell non-adherent regions.
7. The array of paragraph 1, wherein the cell migration unit comprises n migration pathways, n+1 cell non-adherent regions, and at least one cell loading region located at the proximal end of the n migration pathways and n+1 cell non-adherent regions, wherein each of the n migration pathways has a cell non-adherent region located on either side.

8. The array of paragraph 1, wherein the cell migration unit comprises n migration pathway, n+2 cell non-adherent regions, and at least one cell loading region located at the proximal end of the n migration pathways and n+2 cell non-adherent regions, wherein each of the n migration pathways has a cell non-adherent region located on either side.

9. The array of paragraph 6, wherein n is 2 and each cell migration unit comprises at least 2 migration pathways, at least 2 cell non-adherent regions and at least one cell loading region.

10. The array of any of paragraphs 6-8, wherein n is selected from, 2, 3, 4, 5, 6, 7, 8, 9, 10, between 11-15, between 16-20 or more than 20 but less than 50.

11. The array of any of paragraphs 6-10, wherein the migration pathways are of the same width.

12. The array of paragraph 11, wherein the migration pathway has a width selected from 10 μm, 20 μm, 30 μm, 40 μm, 50 μm, 60 μm, 70 μm, 80 m, 90 μm, 100 μm, 110 μm, 120 μm, 130 μm, 140 μm, 150 μm, or greater than 150 μm but less than 3000 μm.

13. The array of any of paragraphs 6-10, wherein the migration pathways are of different widths.

14. The array of paragraph 13, wherein the different widths of the migration pathways are selected from any or a combination of: 10 μm, 20 μm, 30 μm, 40 μm, 50 μm, 601 μm, 70 μm, 801 μm, 90 μm, 100 μm, 110 μm, 120 μm, 130 μm, 140 μm, 150 μm, or greater than 150 μm but less than 500 μm.

15. The array of any of paragraphs 1 to 14, wherein the cell non-adherent region is between 50 μm-500 μm in width.

16. The array of paragraph 15, wherein the cell non-adherent region is between 150 μm-500 μm in width.

17. The array of any of paragraphs 1 to 16, wherein the groove width is between 200 nm-800 nm, the ridge width is between 200 nm to 800 nm, and ridge height is between 200 nm to 800 nm.

18. The array of any of paragraphs 1 to 16, wherein the groove width is between 800 nm-1200 nm, the ridge width is between 800 nm to 1200 nm, and ridge height is between 800 nm to 1200 nm.

19. The array of any of paragraphs 1 to 16, wherein the groove width is between 1000 nm-2000 nm, the ridge width is between 1000 nm-2000 nm, and ridge height is between 1000 nm-2000 nm.

20. The array of any of paragraphs 1 to 16, wherein the groove width is between 2000 nm-3000 nm, the ridge width is between 2000 nm-3000 nm, and ridge height is between 2000 nm-3000 nm 21. The array of any of paragraphs 1 to 20, wherein the at least one migration pathway and the at least one cell non-adherent region is between 0.5 mm-10 mm in length.

22. The array of any of paragraphs 1 to 20, wherein the at least one migration pathway and the at least one cell non-adherent region is between 10 mm-20 mm in length.

23. The array of any of paragraphs 1 to 22, wherein the array comprises at least 2 cell migration units.

24. The array of any of paragraphs 1 to 23, wherein the array comprises at least 3 cell migration units.

25. The array of any of paragraphs 1 to 24, wherein the array comprises at least 6 cell migration units.

26. The array of any of paragraphs 1 to 25, wherein the array comprises at least 8 cell migration units.

27. The array of any of paragraphs 1 to 26, wherein the array comprises at least 12 cell migration units.

28. The array of any of paragraphs 1 to 27, wherein the array comprises at least 24 cell migration units.

29. The array of any of paragraphs 1 to 28, wherein the array comprises at least 96 cell migration units.

30. The array of any of paragraphs 1 to 29, wherein the array comprises at least 384 cell migration units.

31. The array of any of paragraphs 1 to 30, wherein the array comprises at least 1536 cell migration units.

32. The array of any of paragraphs 1 to 31, wherein the array is configured as a multi-well plate, each well of the multi-well plate comprising at least one cell migration unit.

33. The array of paragraph 32, wherein the multi-well plate comprises any of: 2, 3, 4, 6, 8, 12, 24, 48, 96, 384 or 1526 wells.

34. The array of any of paragraphs 1 to 33, further comprising a removable barrier located at the proximal end of the at least one migration pathway and optionally at the proximal end of the at least one cell non-adherent region, wherein the barrier prevents cells present in the cell loading region from entering the migration pathway.

35. The array of paragraph 32, wherein the removable barrier is a micropatterned stamp.

36. The array of any one of paragraphs 1-35, further comprising a population of mammalian cells.

37. The array of paragraph 36, wherein the population of mammalian cells comprises cells attached to the substrate at least in the cell loading region.

38. The array of either of paragraphs 36-37, wherein the cells are human cells.

39. The array of any one of paragraphs 36-38, wherein the cells are tumor cells.

40. A micro-well plate comprising the array of any of paragraphs 1-39.

41. A method for assessing the metastatic potential of a population of tumor cells, comprising:
   a. seeding a population of tumor cells onto a nanopatterned substrate comprising parallel grooves and ridges, wherein the groove width is between 200 nm to 3000 nm, the ridge width is between 200 nm to 3000 nm, and height is between 200 nm to 3000 nm, wherein the tumor cells are seeded at a cell loading region of at least one cell migration unit; wherein the cell migration unit comprises,
      i. at least one migration pathway having a proximal and distal end,
      ii. at least one cell non-adherent region having a proximal and distal end, and
      iii. at least one cell loading region;
      wherein the at least one migration pathway is aligned parallel to the grooves and ridges and comprises a cell-adherent surface, and is between 10 μm-500 μm in width;
      wherein the at least one cell non-adherent region is aligned parallel to the grooves and ridges and is adjacent to the at least one migration pathway; and
      wherein the at least one cell loading region is located at the proximal end of the at least one migration pathway and optionally, at the proximal end of at least one cell non-adherent region;
   b. culturing the tumor cells in the cell loading region to form a monolayer;

c. optionally removing a barrier located between the proximal end of the at least one cell migration pathway and the cell loading region;
d. culturing the tumor cells for a selected period of time to allow migration of the cancer cells along the migration pathway towards the distal end;
e. measuring the distance of cell migration of the population of tumor cells towards the distal end of the migration pathway in the selected period of time.

42. A method for measuring cell migration, the method comprising:
a. seeding a population of cells onto a nanopatterned substrate comprising parallel grooves and ridges, wherein the groove width is between 200 nm to 3000 nm, the ridge width is between 200 nm to 3000 nm, and height is between 200 nm to 3000 nm, wherein the cancer cells are seeded at a cell loading region of at least one cell migration unit; wherein the cell migration unit comprises,
   i. at least one migration pathway having a proximal and distal end,
   ii. at least one cell non-adherent region having a proximal and distal end, and
   iii. at least one cell loading region;
   wherein the at least one migration pathway is aligned parallel to the grooves and ridges and comprises a cell-adherent surface, and is between 10 μm-500 μm in width;
   wherein the at least one cell non-adherent region is aligned parallel to the grooves and ridges and is adjacent to the at least one migration pathway; and
   wherein the at least one cell loading region is located at the proximal end of the at least one migration pathway and optionally, at the proximal end of at least one cell non-adherent region;
b. culturing the population of cells in the cell loading region to form a monolayer;
c. optionally removing a barrier located between the proximal end of the at least one cell migration pathway and the cell loading region;
d. culturing the population of cells for a selected period of time to allow migration of the cells along the migration pathway towards the distal end;
e. measuring the distance of cell migration of the population of cells towards the distal end of the migration pathway in the selected period of time.

43. The method of paragraphs 41 or 42, wherein the selected period of time is a sufficient time to permit cell migration along the migration pathway towards the distal end.

44. The method of paragraph 43, wherein the selected period of time is selected from any of: 20 mins, 30 mins, 1, 2, 3, 6, 8, 10, 12, 24, 36 or 48 hours.

45. The method of paragraphs 41 or 42, further comprising capturing time-lapse images at desired intervals for a series of images during the selected period of time.

46. The method of paragraph 45, wherein the desired intervals are approximately 20-minute intervals.

47. The method of paragraphs 41 or 42, further comprising measuring the distance of cell migration of a population of cells towards the distal end of the migration pathway in the selected period of time in the presence of a test agent, relative to the distance of cell migration of a population of the same cells in the absence of the test agent.

48. The method of paragraphs 41 or 42, further comprising determining the migration speed of the population of cells in the selected period of time.

49. The method of paragraph 48, further comprising determining the migration speed of a population of cells in the selected period of time in the presence of a test agent, relative to the migration speed of the same population of cells in the absence of the test agent.

50. The method of paragraphs 41 or 42, wherein the barrier between the proximal end of the at least one cell migration pathway and the cell loading region is a micropatterned stamp.

51. The method of paragraphs 41 or 42, wherein the population of cells is seeded in the cell loading region in a gel or hydrogel.

52. The method of paragraphs 41 or 42, wherein the at least one cell migration unit is present in an array according to any of paragraphs 1 to 39.

53. The method of paragraph 42, wherein the population of cells comprises tumor cells.

54. The method of paragraph 42, wherein the population of cells comprises blood cells, neuronal cells, keratinocytes, fibroblasts, oligodendrocytes, cartilage, or Schwann cells.

55. The method of paragraphs 41 or 53, wherein the tumor cells are invasive tumor cells or cells of epithelial origin.

56. The method of paragraph 55, wherein the invasive tumor cells are invasive breast cancer cells.

57. The method of paragraph 55, wherein the invasive tumor cells are selected from the group consisting of: prostate cancer cells, colon cancer cells, melanoma cancer cells, ovarian cancer cells, cervical cancer cells, hepatic cancer cells, lung cancer cells and SSC.

58. The method of paragraphs 41 or 53, wherein the cancer cells are not brain tumor cells or glioblastoma cells.

59. The method of paragraphs 41 or 42, further comprising collecting a population of cells from the migration pathway after the selected period of time.

60. The method of paragraph 59, wherein a population of cells that have migrated furthest along the migration pathway in the selected period of time are collected.

61. The method of paragraph 41 or 42, wherein a population of cells located in the distal one-third of the migration pathway after the selected period of time are collected.

62. The method of paragraph 41 or 42, further comprising measuring the distance of cell migration of a population of tumor cells towards the distal end of the migration pathway in the selected period of time in the presence of a test agent, relative to the distance of cell migration of a population of the same tumor cells in the presence of different concentrations of the test agent, and/or the presence of an agent known to inhibit cell migration, and/or the presence of an agent known to promote cell migration.

63. The method of paragraph 41 or 42, further comprising measuring the distance of cell migration of a population of tumor cells towards the distal end of the migration pathway in the selected period of time in the presence of a test agent, relative to the distance of cell migration of a population of cells known to migrate at a particular rate.

64. The method of paragraph 41 or 42, further comprising measuring the proportion of cells in a cell population that migrate one or more chosen distances in the selected period of time.

65. The method of paragraph 48, wherein when a migration speed of more than 20 μm/h is detected on a 120 μm width migration pathway with nanogrooves of 800 nm ridge width, 800 nm groove width and 600 nm groove depth, the cell population is identified to comprise metastatic cells.

66. The method of paragraph 65, further comprising, when the cell population is identified to have a migration speed of more than 20 μm/h, selecting the subject from whom the cells were obtained for a more aggressive cancer therapy than indicated when the cells are not metastatic.

67. A method for identifying an agent which influences the migration of a population of cancer cells, the method comprising the method of any of paragraphs 41-58, performed in the presence and absence of a test agent.

68. The method of paragraph 67, wherein an agent that inhibits the migration of the cancer cells along the migration pathway in a selected period of time by at least 10% relative to migration in the absence of the agent is identified as an inhibitor of migration of the cancer cells.

69. A method of fabricating an array of paragraph 1, comprising:
   a. providing a nanopatterned substrate, wherein the nanopatterned stamp comprises parallel grooves and ridges, wherein the groove width is between 200 nm to 3000 nm, the ridge width is between 200 nm to 3000 nm, and height is between 200 nm to 3000 nm;
   b. placing a micropatterned stamp on the nanopatterned substrate, wherein the micropatterned stamp comprises an array of at least one unit, each unit comprising:
      i. a ridge having a width of between 50 μm-500 μm, wherein the ridge has a proximal and distal end;
      ii. a groove having a width of between 10 μm-300 μm, wherein the groove has a proximal and distal end; and
      iii. a void at the proximal end of the groove and, optionally at the proximal end of the ridge;
   c. treating the nanotextured substrate comprising the micropatterned stamp to change the exposed nanotextured substrate from a hydrophobic surface to a hydrophilic surface, wherein the non-exposed substrate is a cell non-adherent surface;
   d. coating the nanotextured cell surface with an extracellular matrix component coating.

70. The method of paragraph 69, comprising an initial step of generating the nanopatterned substrate, comprising using a nanopatterned stamp to disperse PDMS on a substrate to generate a nanopattern on the substrate, and removing the nanopatterned stamp after the nanopattern is generated, wherein the nanopatterned stamp comprises grooves and ridges, wherein the groove width is between 200 nm to 3000 nm, the ridge width is between 200 nm to 3000 nm, and height of the ridge is between 200 nm to 3000 nm.

71. The method of paragraph 70, wherein treating the nanotextured substrate to change the substrate from a hydrophobic surface to a hydrophilic surface comprises oxygen plasma treatment.

72. The method of paragraph 71, wherein the substrate is glass.

73. The method of paragraph 71, wherein the nanopatterned stamp is a PUA master stamp.

74. The method of any of paragraphs 70-73, wherein the micropatterned stamp is a PDMS master stamp.

75. The method of paragraph 69, wherein the micropatterned stamp comprises an array of 2, 3, 4, 6, 8, 12, 24, 96, 384 or 1526 units compatible with a multi-well plate comprising 2, 3, 4, 6, 8, 12, 24, 48, 96, 384 or 1526 wells.

76. The method of paragraph 69, optionally comprising adding walls of a micro-well plate to generate a multi-well plate comprising 2, 3, 4, 6, 8, 12, 24, 48, 96, 384 or 1526 wells.

77. The method of paragraph 70, wherein the nanopatterned stamp is configured to generate a nanopatterned cell surface in each well of a 2, 3, 4, 6, 8, 12, 24, 48, 96, 384 or 1526 multi-well plate.

78. The method of paragraph 69, wherein the micropatterned stamp comprises an array of 2, 3, 4, 6, 8, 12, 24, 48, 96, 384 or 1526 units and is configured such that each unit generates a micropattern on a nanopatterned cell surface in each well of 2, 3, 4, 6, 8, 12, 24, 48, 96, 384 or 1526 multi-well plate.

79. The method of paragraph 69, wherein the substrate comprises a glass coverslip.

80. The method of paragraph 69, wherein the nanopatterned substrate is present on a glass coverslip.

81. The method of any of paragraphs 79 or 80, wherein the glass coverslip can be inserted into a well of a 2, 3, 4, 6, 8, 12, 24, 48, 96, 384 or 1526 multi-well plate.

82. The method of any of paragraphs 69-81, wherein the extracellular matrix component coating comprises collagen, laminin, or a combination thereof.

83. The method of paragraph 82, wherein the extracellular component matrix coating is collagen.

84. The method of paragraph 82, wherein the extracellular matrix component coating is not laminin.

85. The method of any of paragraphs 69-81, wherein the extracellular matrix component coating further comprises at least one growth factor.

86. A kit for measuring migration properties of a cell, the kit comprising the array of paragraph 1.

87. A kit comprising a nanopatterned substrate, a micropatterned stamp, and reagents for an ECM component coating, wherein the nanopatterned substrate comprises parallel grooves and ridges, wherein the groove width is between 200 nm to 3000 nm, the ridge width is between 200 nm to 3000 nm, and height is between 200 nm to 3000 nm.

88. A kit comprising a nanopatterned stamp, a micropatterned stamp, reagents for an ECM component coating, wherein the nanopatterned substrate comprises parallel grooves and ridges, wherein the nanopatterned stamp is configured to generate a parallel grooves and ridges, wherein the groove width is between 200 nm to 3000 nm, the ridge width is between 200 nm to 3000 nm, and height is between 200 nm to 3000 nm.

89. The kit of any of paragraphs 86-88, wherein the micropatterned stamp comprises an array of at least one unit, each unit comprising: (i) a ridge having a width of between 50 μm-500 μm, wherein the ridge has a proximal and distal end, (ii) a groove having a width of between 10 μm-300 μm, wherein the groove has a proximal and distal end; and (iii) a void at the proximal end of the groove and, optionally at the proximal end of the ridge.

EXAMPLES

Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments. Any variations in the exemplified methods which occur to the skilled artisan are intended to fall within the scope of the present invention.

Methods & Methods

Fabrication of Nanotextured Substrates Having Topographically-Defined Cell Culture Substrates Using UV-Assisted Capillary Force Lithography.

As an exemplary illustration, to prepare micro- and nano-patterned substrate, having a topographically nanogroove-patterned of a nanogroove of: 800 nm width, 600 nm height with 800 nm spacing) elastomeric substrate, a mold made of polyurethane acrylate (PUA) was fabricated from a silicon master patterned via e-beam lithography (JBX-9300FS, JEOL) including photoresist development (MF320, Shipley), deep reactive ion etching (STS ICP Etcher), and ashing process (BMR ICP PR Asher) as previously described.[51-52] Successively, as shown in FIG. 1A, UV-curable PUA was dispensed onto the silicon master and the PET film was brought into contact with the dropped PUA solution followed by UV curing (MT-UV-A21, Minfita Technology) for 15 seconds. The PUA mold (thickness: 0.5 mm) was peeled off from the silicon master and additionally cured overnight. The topographically nanogrooved PDMS substrate was then fabricated using capillary-molding techniques[28,51]. Mixed PDMS solution was dispensed on PET film and the PUA mold was directly placed onto the surface. The PDMS solution filled the cavity of the mold by means of capillary force and was cured at 75° C. for 100 min. After curing the mold was peeled off from the PDMS substrate.

Fabrication of Nanotextured Substrates.

Ultrastructural analysis of the myocardial ECM shows aligned fibrils approximately 100 nm in diameter, consistent with previous reports of collagen fibrils varying in diameter in the 30-120-nm range (Perumal, S. et al., PNAS, 2008. 105(8): p. 2824-9). To account for possible variability, the widths of the grooves and ridges can be varied in the designed patterns (e.g., substantially parallel) from 150-50 nm ridge width and 800-800 nm groove width) and from 200 nm to 500 nm in height. Nanoscale features can be extended to tissue dimension (>3 cm) to facilitate functional analyses at tissue-level (e.g. macroscopic contraction, optical mapping etc.), while also allowing large coverage of infarct (>10 cm$^2$).

To fabricate various nanotextured features of PEG, PUA, PLGA, or any other polymer that can be cured with UV or temperature, any of the following techniques can be employed: capillary force lithography, nanoindentation, ebeam lithography. For UV assisted capillary force lithography, see references as previously described (Kim, et al., Langmuir, 2006. 22(12): p. 5419-5426; Kim, D. H., et al., Integr Biol (Camb), 2012. 4(9): p. 1019-3; Kim, et al., PNAS, 2010. 107(2): p. 565-570; Kim, D. H., et al., Advanced Functional Materials, 2009. 19(10): p. 1579-1586; You, M. H., et al., Biomacromolecules, 2010. 11(7): p. 1856-1862). Briefly, the cover glass is washed with isopropyl alcohol (IPA) for 1 min, cleaned using distilled water and dried in N$_2$. PEG-GelMA prepolymer solution (100 µL) is be drop-dispensed on the glass and kept at 40° C. to prevent premature gelation. Nanopatterned polyurethane acrylate (PUA) mold is placed on the coated polymer layer and embossed into the prepolymer, and prepolymer capillarity fills the nanofeatures of the PUA master. The polymer is then exposed to UV light (360-480 nm) for ~50 sec. to polymerize and assume the nanotextures.

For thermal assisted capillary force lithography, cover glass (25 mm typically) is washed with isopropyl alcohol for 30 min in a water sonication and dried in nitrogen stream. The prepared 100 µl of polymeric solution (15%, w/v) in chloroform is dropped on the cover glass. A flat PDMS is placed on the dispensed polymeric solution to remove solvent and obtain a smooth flat layer. A metal mass is placed to evenly press on PDMS mold for 5 min. The cover glass is placed on preheated plate (120° C.) to remove residual solvent and increase adhesion between polymer and cover glass for 5 min. Then, a nanopatterned PUA mold is placed on the polymer coated glass and embossed with constant pressure using metal mass (1,500 g) at preheated plate (120° C.) for 15 min. After thermal imprinting process, the assembly substrates is cooled to room temperature, and the PUA mold is carefully peeled off from the polymer coated glass. Finally, the prepared nano-patterned substrate stored at desiccator for removing residual solvent.

Characterization:

High pattern fidelity and physical integrity of nanofabricated polymeric biomaterials can be optionally assessed by SEM and AFM measurements. Elastic modulus and hardness of the resulting cured nanotextured substrates are measured by using nanoindentation (Nano Indenter XP, MTS).

PUA Mold Fabrication:

In order to generate high-fidelity nanoscale grooved substrates, polyurethane acrylate (PUA) molds were fabricated from a silicon master for subsequent replications. PUA precursor (MINS 201RM, Minuta Tech.) was drop-dispensed onto a silicon master which was fabricated using standard lithography techniques. Transparent poly(ethylene terephthalate) (PET) film (Skyrol®, SKC Company) was pressed gently into the PUA precursor and silicon master for use as a supporting backplane. The PUA was then cured by exposure to UV light (λ=250-400 nm) for 50 sec. After curing, the PET film and attached PUA, in the form of the negative of the silicon master, were peeled from the silicon master and exposed to UV light for an additional 12 hours to complete curing.

Glass Nanofabrication:

To prepare glass surfaces for fabrication, glass surfaces, e.g., the bottom of a multiwall plate, or, in some embodiments, cover glass slides (e.g., 25 mm diameter circular cover glass slides (Fisher)) are wiped or placed in isopropyl alcohol for 30 min in a water sonicator and then dried under a nitrogen stream. Capillary force lithography was used to fabricate the anisotropic nanogrooved substrates from the PUA master. Briefly, a thioester prepolymer (NOA 83H, Norland Products, Inc.) was drop-dispensed onto the center of a glass slide and the PUA mold was placed pattern-face-down on top. A rubber roller was then used to evenly spread the prepolymer across the surface of the glass slide. The thioester polymer was then cured by exposure to UV light for 60 sec. After curing, the PUA mold was carefully peeled off the glass slide, leaving behind the nanopatterned substrate with 800 nm wide ridges and grooves with a ridge height of 500 nm (FIG. 1). The cover glass slides could then be placed into the well of a multi-well dish for cell culture.

Flat control substrates were created using a similar method as described above. However, instead of placing the PUA nanopatterned mold onto the thioester prepolymer on the glass slide, a piece of PET film was gently placed on top. A rubber roller was again used to evenly disperse the prepolymer over the glass slide before UV curing.

Microstamp-Assisted Plasma Lithography for Spatial Migration Pathway Patterning.

The process of making the migration pathway patterns on the substrate is composed of two different lithographic techniques. Photolithographic and plasma lithographic techniques were used to fabricate a microchannel-patterned PDMS stamp and create selective hydrophilic micropatterns, respectively. Thus creating a hydrophilic and hydrophobic array allows for cell adhesion on alternating lines (FIG. 1B), where the hydrophilic region is the cell migration pathway and is cell adherent, and the hydrophobic regions are substantially cell non-adherent.

First, a microchannel-patterned stamp was fabricated using soft-lithographic techniques and molding into PDMS as described previously[71,72]. Briefly, a micropatterned template stamp is prepared where the width of the ridges (that contact the nanopatterned substrate) correspond to the width of the hydrophobic regions in the migration unit, and the width of the grooves which do not contact the nanopatterned substrate correspond to the width of the migration pathway. The micropatterned template was prepared by fabricating a SU-8 master composed of various microchannels using standard soft-lithography techniques. A Si wafer was coated (Solitec spin coater) with photoresist (SU-8, MicroChem, MA), exposed to UV light (ABM mask aligner) through a chrome mask (Fineline Imaging, CO) to polymerize the photoresist, and finally the unexposed photoresist was washed away. 10 to 1 mixed PDMS prepolymer was dispensed onto the silicon master and then cured for 2 hours at 75° C. thereafter. Then, the 3D patterned PDMS stamp (14 mm (L)×10 mm (W)×2 mm (H)) was peeled off from the silicone master (step 1 in FIG. 1B).

Next, the surface of the substrates were modified using plasma lithographic techniques[50,73] with the 3D microchannel patterned (20, 40, 60, and 100 μm width straight lines, 15 lines each) stamp to make spatial cellular patterns and to direct the cellular migration as shown in FIG. 1B. First, a culture platform was composed of the 3D micropatterned PDMS stamp, a PDMS barrier used for trapping cells, a topographically nanogroove-patterned PDMS substrate, and a coverglass. The PDMS stamp was placed in conformal contact with the surface of flat and nanogrooved substrates surrounded by a large PDMS well (step 2 in FIG. 1B). The cell culture platform was then exposed to atmospheric plasma (CUTE, Femto Science) set at 80 W and 0.5 Torr for 3 min (step 3 in FIG. 1B). Due to the physical channels formed between the 3D stamp and the substrate, the substrates were selectively and chemically modified by the plasma, creating micropatterns that serve as the only passageways for cell migration. To improve attachment, movement, and mimic the primary protein ECM component of the tumor stroma, collagen type I (50 μg/mL) solution was subsequently injected into the large PDMS well (14×12×8 mm), which was made to trap cells only on the patterned area. The microchannels were fully filled with the injected ECM solution within 5 min, and the culture platform was then incubated. After 3 hours of incubation, the filled ECM solution was removed by air blast, and the microchannels were washed with 1×PBS twice followed by air drying (step 4 in FIG. 1B). Finally, 0.2 mL of culture media was added into the PDMS well, and after the microchannels were filled with the media, cells were seeded into the well with defined seeding density. After one day of incubation, the 3D stamp was removed, and the culture platform was incubated for an additional 6 hours until the monolayered cells at both ends of the patterns created 150 μm extended arms of cells into the patterns (step 5 in FIG. 1B). Cellular migration along the micropatterns was imaged using a live cell imaging microscope for 18 hours.

Coating of Proteins/Peptides Matrix Molecules on Nanotextured Substrates

The nanotextured substrates can be coated with a variety of proteins, peptides and matrix molecules by applying aqueous solution of the desired molecules on the surface of nanotextured platform, and coating for 1-24 hours at multiples of concentrations. In multi-well nanotextured platforms, conditions can be varied by varying multiples of concentration of the desired molecule in each well. The extent of coating and evenness of coating can be measured using fluorescent labeled molecules to coat (when available), or by immunostaining.

Coating of Lipid Molecules on Nanotextured Substrates

To immobilize biolipid molecules, e.g. sphingosine 1-phosphate (SIP) to nanotextured substrates, various amounts of S1P dissolved in sterile phosphate buffered saline is placed on substrates and dried for 1 hour at 4° C. The efficiency of S1P complexation to various nanopatterned substrates is determined using enzyme-linked immunosorbant assay (ELISA), or X-ray photoelectron spectroscopy (XPS). Since S1P-nanotextured polymeric platform is non-conducting, aS-probe spectrophotometer containing monochromatized Al Kα X-ray and a low energy electron flood gun for charge neutralization can be used. The amount of nitrogen and phosphate are expected to be significantly higher in comparison to the control unconjugated substrates. Further analysis of C1s line shape should indicate that peaks assigned to COOH decrease after S1P coating.

Few-Layer Graphene Oxide and Reduced Graphene Oxide Coating on Nanotextured Substrates GO consists of single atomic layer of carbon atoms arranged in honeycombs, bonded to oxygen atoms in the form of carboxyl, hydroxyl, or epoxy groups[7-9]. Reduced GO can be prepared from GO via chemical, thermal, hydrothermal and electrical reduction, thereby removing the oxygen functional groups (refs). For fabrication of few-layered graphene coating on the PEG substrate, graphene oxide (GO) suspension is first prepared using well established Hummus method from graphite (refs). The prepared GO suspension was then rinsed in deionized water three times and the resulting GO suspension had a concentration of 5 mg/ml. The few-layered GO was coated on previously prepared PEG nanostructure by chemically adsorbing the GO flakes to PEG overnight via covalent and non-covalent interactions. The electrical and chemical properties, including electrical conductivity, oxygen functional group species and density can be modulated by changing the duration of chemical reduction, concentration of reducing chemical agents, changing temperature in thermal and hydrothermal reduction and changing applied current in electrical reduction. The GO can be characterized using raman spectroscopy, 4-point probe, scanning electron microscopy (SEM), atomic force microscopy (AFM) and conductive atomic force microscopy (cAFM) are used to measure the nanoscale topology, surface chemistry and electrical conductivity of the samples.

Single-Layer Graphene Coating and Controlled Oxidation for Tunable Chemical Functionality and Electrical Properties Single-layer Graphene was grown on copper (Cu) foil by chemical vapor deposition (CVD) at 990° C. using methane as precursor. Following deposition, a thin film of poly (methyl methacrylate) (PMMA) was spin-coated on the graphene. The Cu foil was then be etched away in dilute HNO3, and graphene/PMMA was rinsed twice in deionized water. In order to avoid graphene/PMMA film from folding up, the transfer of graphene took place at an air-water interface, where surface tension of water will keep graphene flat. The transfer of graphene onto patterned PEG substrates was done while floating graphene/PMMA flat at air-water interface with the graphene side facing down. The PEG substrate will then be placed in water with the patterned PEG side facing up underneath the graphene/PMMA, and brought up through the air-water interface at an angle to make a confluent contact with graphene. Once the graphene/PMMA is transferred on top of the PEG substrate, the PEG/graphene/PMMA was left in the hood to dry. During the drying process, capillary force allowed graphene film to fill in the grooves and make the desired patterned graphene. Finally, the PMMA was removed in acetone and isopropanol alcohol in order and the resulting graphene/PEG nanostructure was rinsed in de-ionized water twice.

The surface composition of oxygen functional groups and resulting electrical conductivity of prepared single-layer graphene coated PEG nanopattern was controlled by introducing oxygen defects onto graphene surface. The defects could be successfully introduced by oxygen, argon and carbon dioxide plasma treatment. A single-layer of graphene or GO can be characterized and analyzed using Raman spectroscopy, 4-point probe, scanning electron microscopy (SEM), atomic force microscopy (AFM) and conductive atomic force microscopy (cAFM) are used to measure the nanoscale topology, surface chemistry and electrical conductivity of the samples.

Graphene (G) and Graphene-Oxide (GO) Coating on Nanotextured Substrates

Graphene-oxide (GO) consists of carbon atoms bound in a single-atom-thick sheet as honeycombs, bonded to oxygen atoms in the form of carboxyl, hydroxyl, or epoxy groups (Yang, K., et al., Biomaterials, 2012. 33(7): p. 2206-14; Dreyer, D. R., et al., Chem Soc Rev, 2010. 39(1): p. 228-40; Andre Mkhoyan, K., et al., Nano Lett, 2009. 9(3): p. 1058-63). Nanogrooves are cleaned with 10 mM APTES-toluene solution, followed by a toluene+ethanol wash. GO-water solution is dispersed through ultra-sonication, and substrates submerged in the solution to facilitate GO self-assembly coating process, washed with ethanol and dried in $N_2$. Raman spectroscopy and atomic force microscopy (AFM) is used to measure the extent and evenness of coating. The characterization of conductivity of the substrate is done using conductive AFM, scanning electron microscopy, in addition to measuring resistance to current flow.

Cell Culture and Targeted Knockin of the PIK3CA Oncogene.

All studies in this article were performed using stable lines of human-derived MCF-10A breast epithelial cells and MCF-10A mutant PIK3CA knockin cells. Culture procedures for the MCF-10A line and its derivatives has been described previously[22-24]. Briefly, MCF-10A cells and the PIK3CA knockin cell line were propagated in Dulbecco's Modified Eagle's Medium (DMEM)/F12 (1:1) (Life Science) supplemented with 5% horse serum, 20 ng/mL EGF, 10 g/mL insulin, 0.5 g/mL hydrocortisone, and 0.1 g/mL cholera toxin. All supplements were purchased from Sigma-Aldrich, unless otherwise noted. To generate the PIK3CA knockin line, targeting vectors were designed to introduce a single oncogenic mutation within PIK3CA. Vector transduction, colony selection, clone screening, and Cre recombinase removal of the neomycin resistance gene have been described previously[74,75]. For cell patterning, cell suspensions were introduced into the device, at the cell loading region, at volumetric cell densities sufficient to achieve a subconfluent density, tested from 1300 cells/mm$^2$ to 1800 cells/mm$^2$, and then cells were allowed to adhere to the flat or nanogrooved elastomeric substrates. Prior to the start of imaging and data acquisition, cells were additionally cultured in the cell loading region, which can have a flat stencil or a nanopatterned surface, and are prevented the cells entering the migration pathway, therefore allowing the cells to create a dense cell monolayer as described above, prior to the beginning of the assay.

Quantitative Analysis of Cell Migration and Modeling.

Figure 1C:
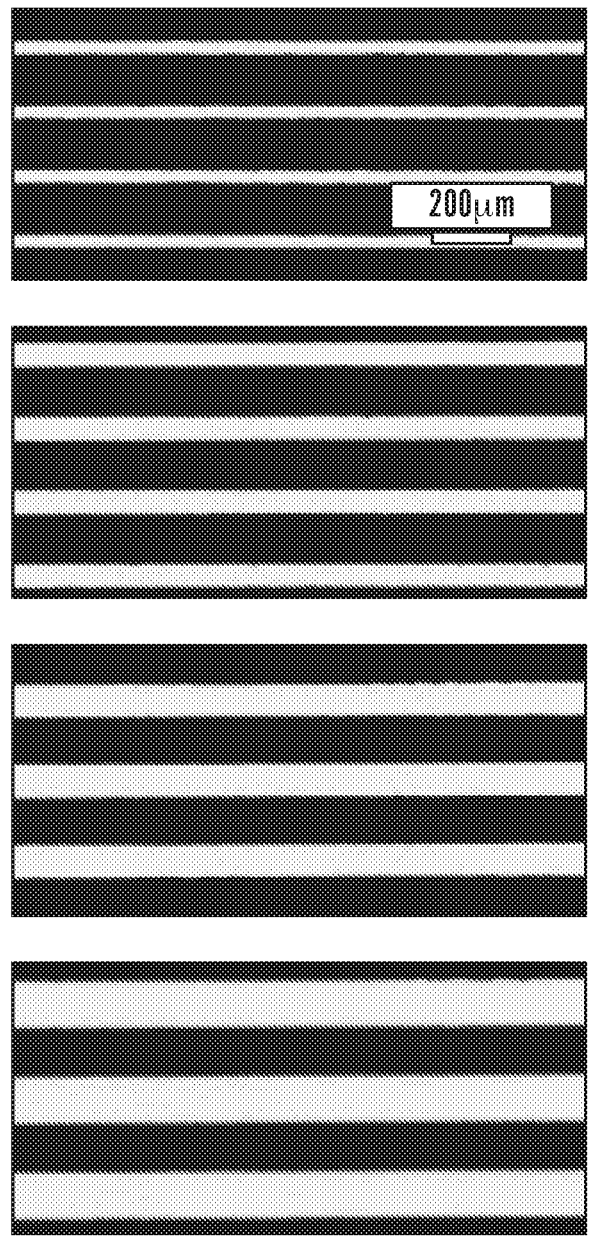
Figure 1D:
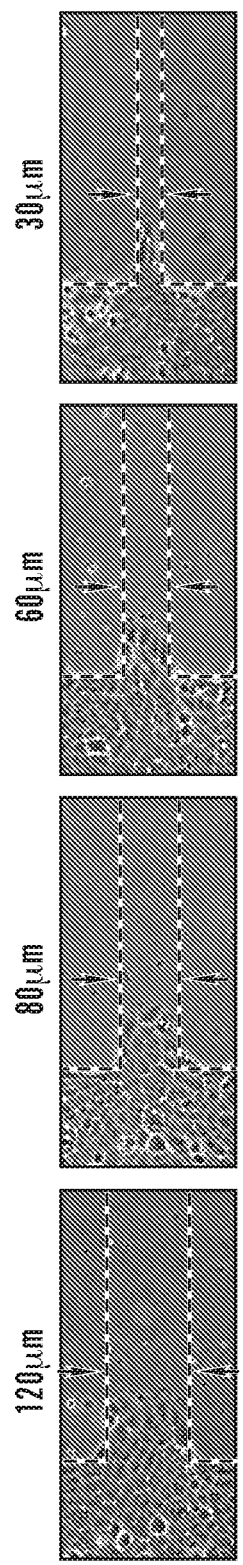

After initial cellular patterns were created, as shown in FIG. 1D, cell motility was measured by acquiring images at multiple locations, e.g., at every 20 minutes for 18 hours using an automated live cell microscope (Eclipse Ti, Nikon). Other intervals for acquiring images are encompassed, e.g., at 5-min, 10-min, 20-min, 30 min, 1 hr intervals, for approximately 1 hr to 48 hrs, or 3 days, or 4 days or 5 days or more than 5 days. The cell nucleus was tracked at each time point and custom computational routines were implemented in MATLAB 8.1 (The MathWorks, Natick, Mass.) to plot trajectory and calculate the migration speed and persistence time parameterized by a persistence random work model[60-62]. Migration speed was measured by calculating displacement per time. Individual cell speeds and persistence times from each experiment were averaged to obtain a single experiment's parameter means and the associated standard errors. Each experiment was technically replicated at least three times with the number of 40-100 cells for each experiment. Associated error bars represent ±2 SE and were derived using standard propagation of error techniques. Finally, statistical analysis was carried out by student's t-test for between two groups (MCF-10A vs. PIC3CA knockin cells, flat vs. nanogrooved), and two way ANOVA test followed by post-hoc (Duncan method) analysis for different pattern widths versus cell type or substrate type. P values less than 0.05 were regarded as statistically significant.

To implement the diffusion anisotropy model presented here, particles (representing cells) perform a random walk within geometrically constrained two-dimensional space (i.e., the migration pathway) (varying constraint in the y direction). Following random walk behavior a particle moves stepwise in a random direction. That is, at each time step ($\Delta t$) the particle undergoes a displacement ($\delta$) along a randomly chosen direction. Here the trajectory direction vector is limited so the x component is in the positive direction to account for constraints imposed by cells behind the leading edge in collective migration. Likewise, the particle displacement is constrained by restricting movement outside of the defined y boundary.

Example 1

The malignant progression of breast tumors is a multi-step process driven by specific oncogenic alterations and loss of tumor suppressor gene function (Hanahan et al., 2011, Cell, 144, 646-674). In particular, the PI3K pathway is frequently dysregulated in numerous malignancies[17-19], making it an attractive target for cancer therapy. Indeed, PI3K is the subject of therapeutic exploitation along with other key downstream effectors (e.g. AKT, mTOR etc.), as PI3K pathway signaling regulates numerous critical behaviors required of transformed cells, including growth, survival and invasion[22, 23]. Recent studies show that PIK3CA, the p110α catalytic subunit of PI3K, is frequently mutated in a number of different human cancers, including those of the breast[17-19]. Interestingly, the recent success of generating PIK3CA knockin modification in human breast epithelial cells provides an excellent cancer model to investigate the role of PI3K signaling in breast cancer and identify new therapeutic targets associated with oncogenic PIK3CA mutations[22-24]. Thus, although studies have implicated PIK3CA mutations with features of transformation, e.g. see References 20 and 21, definitive mechanisms describing how these mutations lead to changes in cell morphology, growth and motility have not been fully elucidated. Here we seek to understand if aberrant PI3K signaling confers an advantage for cells migrating within an in vivo micro/nanoenvironment conducive to invasion and metastasis (i.e. collagen bundle spacing and alignment in the tumor stroma and tracking along collagenous fibers to intravasate[6, 14, 25]). To this end, the inventors have combined innovative micro and nanofabrication techniques and surface-modified biomaterials to mimic the mechanical and structural properties found in the in vivo Tumor microenvironment (TME).

Cell patterning on a defined substrate is a critical challenge in the field of cell biology in order to address fundamental biological questions about cell-cell or cell-substrate interactions and the systematic mechanisms driving their behavior in response to the local environment[26-29,30,31]. Precisely controlled geometry can be achieved using defined engineering of the surface properties of biocompatible materials to provide a framework for cell adhesion and motility. For instance, a number of cell patterning techniques, such as microscale plasma-initiated patterning[33], microcontact printing[34,35], the use of polyelectrolyte multilayers as an adhesion layer[36], microelectrode arrays[37,38], microfluidics-based methods[39], inkjet printing[40, 41], and photolithography[42], to generate ECM mimetic substrate models have been developed for cell and tissue engineering applications[33-48]. To allow independent control of substrate topography and pattern geometry, the micropatterning technique should be compatible with nanostructural design and elastomeric substrate materials. Other important considerations when selecting a patterning technique for the investigation of cell migration is its high-spatial resolution and the long-term stability of the patterns, since the patterns act not as a geometric settlement, but as a migratory conduit with the defined various widths for precise control. To address these issues, plasma lithography[42,49-50] has been developed and applied to investigate cell migration in a defined microenvironment. Plasma lithography creates surface modified geometry based on selective plasma surface functionalization of polymeric materials such as PDMS. Such modified geometry can be utilized to tune a wide range of mechanical and biochemical properties. This technology provides long-term stability, reproducibility, scalability, and cost-effectiveness. Nanotopography can also be created on various materials using capillary force lithographic techniques[5-53]. For instance, this method can be used to fabricate nanogroove patterns on elastomeric substrates, allowing for a wide range of applications due to cost effectiveness, scalability, and reproducibility[54-56]. In the working Examples disclosed herein, UV-assisted capillary force lithography and plasma lithography were used to fabricate nanotopographic features and ECM micropatterns on elastomeric substrate to provide both non-transformed and transformed cells with contact guidance cues operant in breast cancers.

To this end, described herein is the design of an innovative engineered biomimetic platform with nanostructured surface patterning, which allows for the integrative study of complex stimuli that include micro and nanotopographic cues, and selective ECM composition and adhesiveness, to elucidate the roles of these critical factors and their interrelationship in the regulation of cell migration. Capillary force lithography and plasma lithography patterning was performed on PDMS substrates with different geometries to guide and promote cell migration. The results demonstrated that human breast epithelial cells and their genetic derivatives collectively sense and respond to the engineered microenvironment by integrating the microstructural and mechanical properties of the substrate during cell migration. Furthermore, this work demonstrates the applicability of the biomimetic approach to modulate substrate-mediated cell migration phenomena and shows that these factors influence migration speed and persistence time of oncogenic PIK3CA knockin mutants of human breast epithelial cells, signifying a correlation between oncogene activation and tumor cell metastatic potential.

Rational Design and Fabrication of an Engineered Biomimetic Culture Platform

Three different lithographic techniques were applied to create spatial patterns of migration pathways on nanogrooved elastomeric substrates. Namely, the engineered biomimetic culture platform was composed of three major parts; a nanogrooved elastomeric substrate fabricated by UV-assisted capillary force lithography and PDMS molding, a microchannel patterned PDMS stamp fabricated by soft-lithography, and selectively modified ECM patterns prepared by plasma lithographic process. The large area nanogroove pattern on a silicon master (2 inches by 2 inches) was successfully transferred to the thin PUA template fabricated by UV-assisted capillary force lithography. The SEM image shown in FIG. 1A (bottom) represents a complete nanofabricated PDMS substrate successfully cured over the PUA template. PDMS substrates were obtained from up to 50 replicas from a PUA template without any topographic defects. The thickness of the patterned PDMS substrates was less than 0.6 mm for microscopic observation. Consequently, the successful fabrication process of the large number of copies from a single template shows an inexpensive, mass producible, and reproducible nature of the capillary force lithography.

PDMS microstamp-assisted plasma lithographic techniques were used to create spatial surface patterns for MCF-10A culture on the nanogroove patterned elastomeric substrates (FIG. 1B, step 3). A PDMS microstamp was fabricated with photolithography to have nanopatterned substrate contact area (non-plasma treated) and open area (plasma treated). The open area (i.e. excluding the contact area with the stamp) was successfully modified and characterized by microscopic inspection of aqueous medium with dye. The restricted wetting confirmed a successful micro surface patterning.

The inventors demonstrate herein, two types of plasma lithographic patterns, straight-edged flat patterns as a control and 10 mm migration pathway patterns with 30 μm (33±1), 60 μm (60±1), 80 μm (80±2), and 120 μm (119±2) widths (15 migration pathways for each dimension with approx. 150 μm spacing/hydrophobic regions between each migration pathway) were created. The regular spacing between two migration pathways regardless of their width was suitable for preventing interrelation between migrating cells along each ECM-coated migration pathway. This process was accomplished within 5 minutes and we confirmed that the technique provided long-term stability (>2 month) and high spatial resolution (>200 nm). Additionally, Collagen Type I was coated on the modified patterns of migration pathways (FIG. 1B, step 4) to enhance cellular attachment and movement by mimicking the primary protein ECM component of the tumor stroma. Successful surface modification and migration pathway patterned structures were characterized by microscopic inspection of the collagen type I (50 µg/mL) with fluorescent dye wetted on only plasma treated areas as shown in FIG. 1C. Moreover, it was confirmed that the collagen was uniformly coated on the nanostructured surface including the inward regions of the nanogrooves by measurement of the cross-sectional fluorescent intensity of patterned microchannels.

Breast epithelial cells were dispersed on the cell loading region of the substrate, and in this case, the cell loading region was enclosed by a PDMS well with an optimized seeding density of 1600 cells/mm² for all experimental conditions (FIG. 1B, step 5). The dispersed cells were prevented from entering migration pathways, as the PDMS formed a barrier, allowing the same seeding density in the cell loading area. Removing the barrier, in this case, the PDMS stamp when a complete monolayer was created to prevented the cells from settling on the ECM-coated migration pathways and permits the monolayered cells, not individual cells, to enter into the ECM-coated migration pathways at the same time as shown in FIG. 1D. The monolayered cells were selectively placed on the cell loading region (which can be flat or have a nanogrooved surface) resulting in successful cellular pattern formation as the breast epithelial cells were confined to the plasma treated, and ECM coated, hydrophilic areas. The width of monolayered cells patterned at the left side shown in each microscopic image as well as the straight-edged flat patterns shown in FIG. 2A-D was designed 1 mm wide to diminish the effect of proliferation rate on directed cell migration. Further experiments were relatively short (much shorter than their doubling time of ~24-30 hrs[57,58] so the effect of proliferation rate on migration speed was minimal and only non-dividing cells were tracked. By microscopic inspection, leading cells at the moving front and following cells entering into the ECM coated migration pathways have different migratory speeds, but once the cells fully enter the migration pathway, the migration speed of the cells become essentially equivalent for a given cell type regardless of the migration pathway width.

Therefore images were captured from the time point when the cells clearly entered at least 150 µm into the migration pathway. Consistent with the inventors' prior validation using dye, the breast epithelial cells migrated along the migration pathways and leave the patterns. Consequently, the inventors have demonstrated that plasma lithography can efficiently be used to form micropatterns with ECM component coating, e.g., form migration pathways on nanogroove-patterned PDMS substrates. The nanotopography on the elastomeric substrate allows the cells to move in a directed fashion, with the migration pathways with ECM component coatings acting as geometric conduits, while nanotopography provides contact guidance to direct migration direction and enhance migration speed of the cells. Therefore, the engineered biomimetic culture platform having a nanogrooved surface and micropatterns of ECM coated migration pathways allows independent control of geometric guidance and migratory trajectory to investigate directed migration of normal and transformed cells.

Example 2

Nanoscale Contact Guidance Cues Promote Directed Collective Cell Migration

Figure 2A:
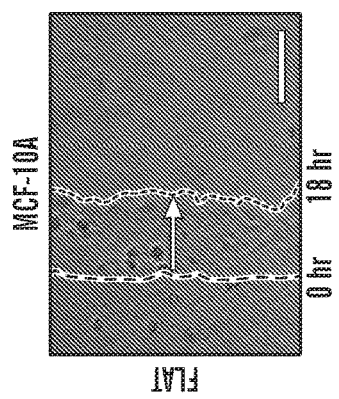
FIGS. 2A-2J show migration of cells along straight edge migration pathways on flat and nanogroove-patterned PDMS substrate.
Figure 2C:
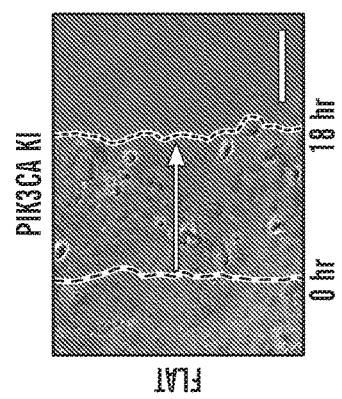
Figure 2E:
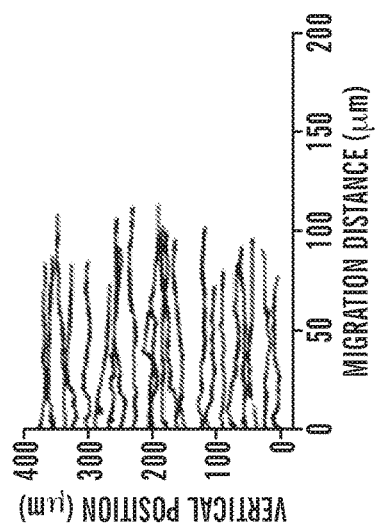
Figure 2B:
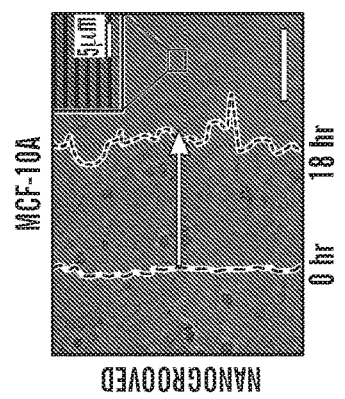
Figure 2D:
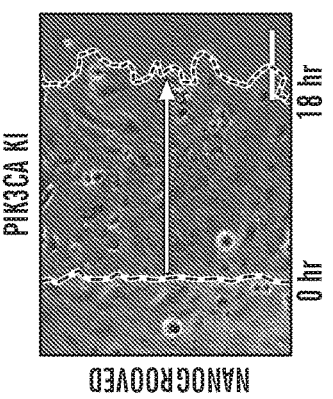
Figure 2F:
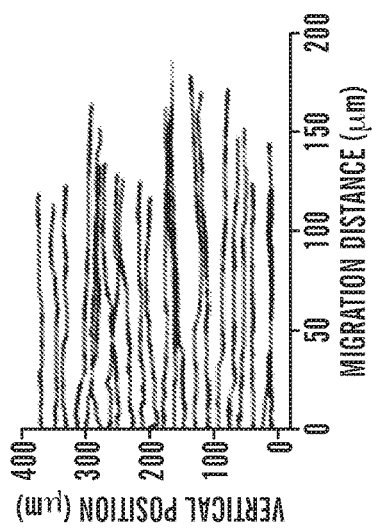

The inventors' previous studies demonstrated that substrate nanotopography allows cardiac cells to align along the nanogroove direction and promotes cellular attachment[51,59]. Here, the inventors have quantitatively determined the influence of the combination of nanotopology and multiscale cues (e.g., micropatterns of the ECM coated migration pathways) on cells, for example, cells with and without an intrinsic perturbation (i.e. oncogenic mutation). First, straight-edged monolayers (1 mm wide, 14 mm long) of the breast epithelial cell line MCF-10A and its derivative, knockin of mutant PIK3CA, were generated on the ECM-coated elastomeric substrates using stencil-assisted plasma lithography as shown in FIG. 2. When the cell monolayer of MCF-10A breast epithelial cells, or PIK3CA cells occurred in the cell loading region, the barrier preventing access of the cells to the migration pathways was removed (in this case, the stencil was removed) and image analysis confirmed the presence of wide straight-edged monolayers of either MCF-10A or PIK3CA knockin cells on flat substrates (FIGS. 2A and C) or on nanogrooved PDMS substrates (FIGS. 2B and D). Second, subsequent analysis of cell migration of both cell types demonstrates that the cells follow a persistent random walk model[60-62] parameterized by cell migration speed and directional persistence time[63,64], defined as the average time between significant changes in the direction of a cell's translocation[60]. The speed of each cell was determined by dividing the root mean-square displacement (MSD) of the path of each migrating cell, tracked for N sequential positions by the constant time interval $\Delta t$, calculated using the method of non-overlapping intervals[65]. Each cell's persistence time was fit using nonlinear least-squares regression by inserting its speed into the persistent random walk model. The paths of individual cells migrating on both flat and nanogrooved substrates were analyzed over 18 hours with interval time-lapse imaging (N=54, $\Delta t$=20 min) by tracking individual cell positions within each image.

Figure 2G:
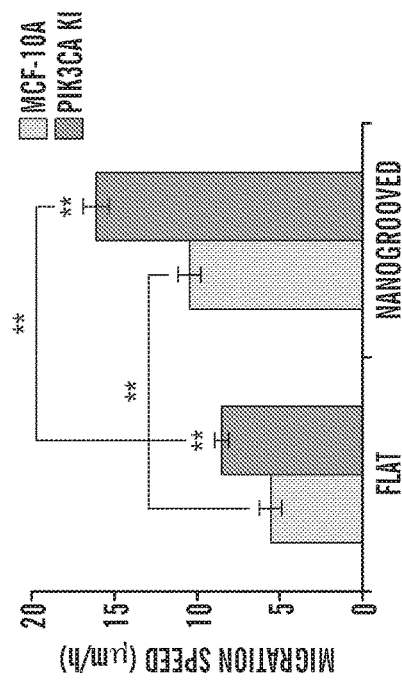
Figure 2I:
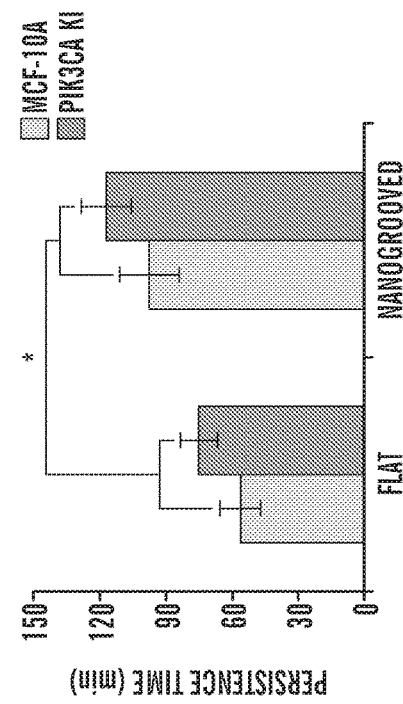
Figure 2H:
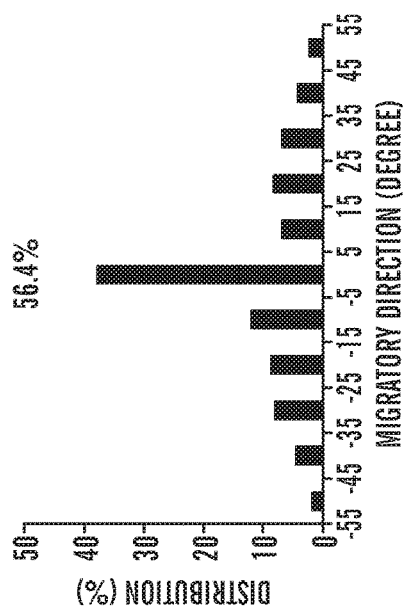

Quantitative analysis of the clear qualitative differences in cell migration (FIG. 2A-D) demonstrates a significant difference (p<0.01) in migration trajectories (migration distance and direction) of MCF-10A cells on flat (FIG. 2E) versus nanogrooved (FIG. 2F) PDMS substrates. Similar findings were determined with mutant PIK3CA cells (data not shown). Furthermore, results demonstrate that human breast epithelial cells on nanogrooved substrates exhibited a more linear migration trajectory, with a longer migration distance within a defined experimental time (FIG. 2F) than the same cells on flat substrates (FIG. 2E), demonstrating a strong contact guidance mediated migration along the direction of the nanogrooves. Likewise, migratory direction of individual paths defined as the angular deviation from the fabricated nanogroove direction was measured (FIGS. 2G and H). The angle represents the degree by which cells deviate from the long axis of the nanogroove with 0 degree indicating that the direction of migration is in complete congruity to the direction of nanogrooves. The proportion of migration paths that were within ±15 degrees from the nanogrooves was calculated to specifically assess an effect of the nanogrooves on migratory contact guidance. From this analysis, the inventors discovered that 56.4% of migration paths on the flat substrate and 73.2% on the nanogrooved substrate are within ±15 degree of the primary axis. Thus, nanotopographic features within microscale constrained migration regions (e.g., the migration pathways)

further promote directed cell migration, with the addition of nanogrooves contributing significantly to contact guidance by producing an ~30% increase in directional migration compared to migration on flat substrates.

Figure 2J:
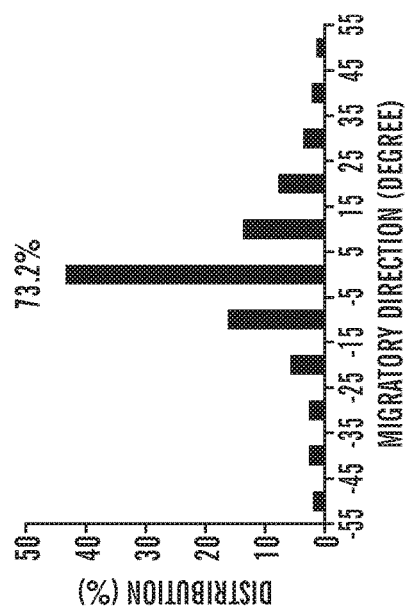

In order to further elucidate the influence of nanotopography on directed cell migration, the inventors fit the mean-squared displacement of the cell path data to the persistent random walk model, as described above, to obtain migration speed (FIG. 2I) and persistence time (FIG. 2J). Interestingly, both the MCF-10A wild type cells and mutant PIK3CA knockin cells migrate on average 87% (±2%) faster (p<0.001) along nanogrooved substrates as compared to on flat substrates, demonstrating that the topographic nanogrooves alters motility dynamics to enhance migration speed. Moreover, oncogenic PIK3CA knockin cells migrate on average 53% (±2%) faster (p<0.001) on both flat and nanogrooved substrates as compared to their wild type counterpart MCF-10A cells, demonstrating that oncogenic mutations of PI3K enhance cell migration, consistent with the concept that PIK3CA may promote breast cancer metastasis. Additionally, directional persistence of both cell types (FIG. 2J) in the presence of nanoscale guidance cues showed a significant increase (p<0.01), providing further evidence that contact guidance architecture enhances directed migration through increased persistence. Hence, these result demonstrate that the cells on nanopatterned substrates migrate for a longer average time without significant changes in the direction, and with enhanced speed, as compared to their migration on flat substrates, which is due to a straightforward contact guidance mediated migration along the direction of the nanogrooves.

Example 3

The Width of Microscale ECM-Coated Migration Pathways Influences Directed Cell Migration.

The inventors biomimetic culture platform disclosed herein not only promotes increased cell migration speed and persistence via nanoscale contact guidance cues, but also facilitates the identification of significant differences in migration of cells as a function of varying microscale geometric constraints achieved by the ECM-coated migration pathways.

Figure 3A:
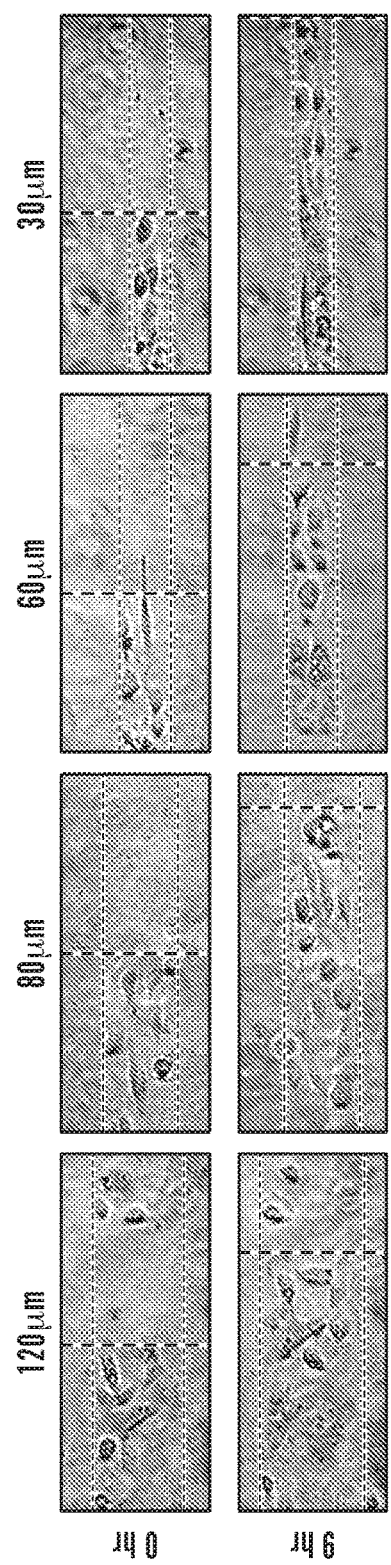
FIGS. 3A-3C show cell migration along ECM-coated migration pathways using plasma lithographic techniques.
Figure 3B:
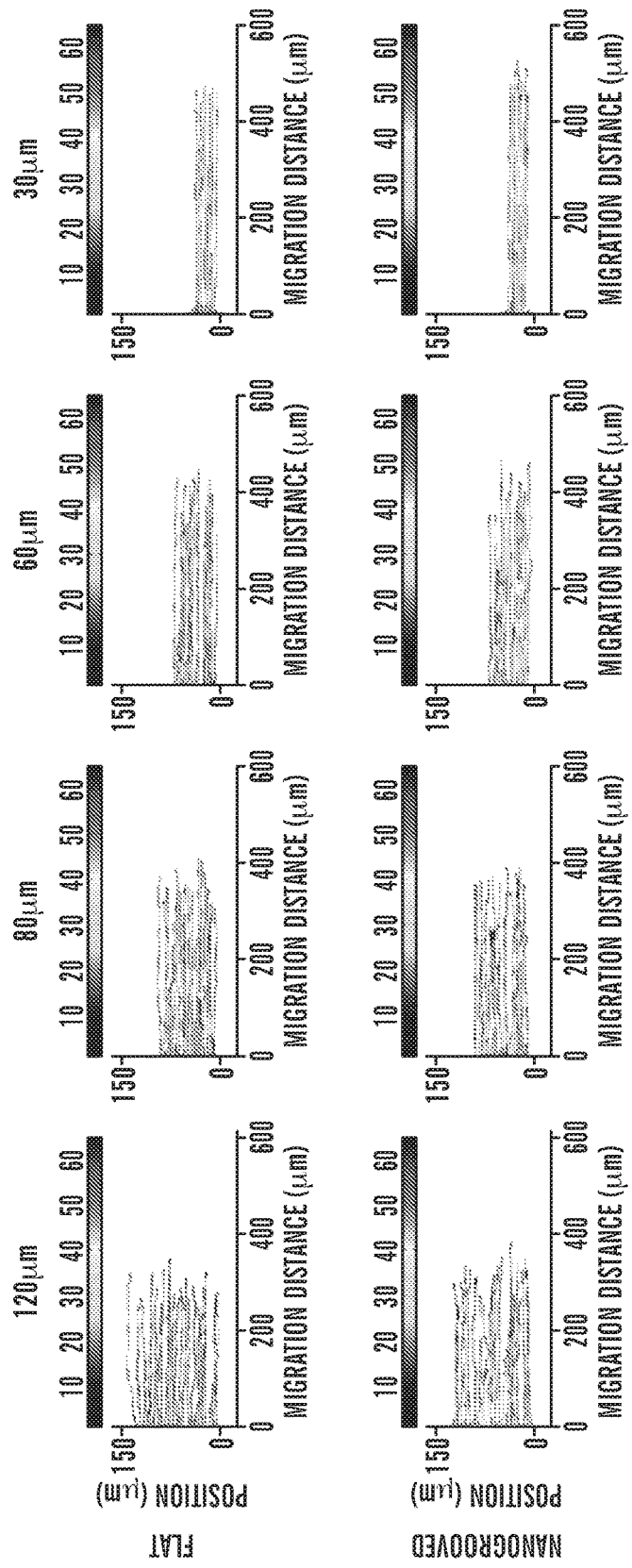
Figure 3C:
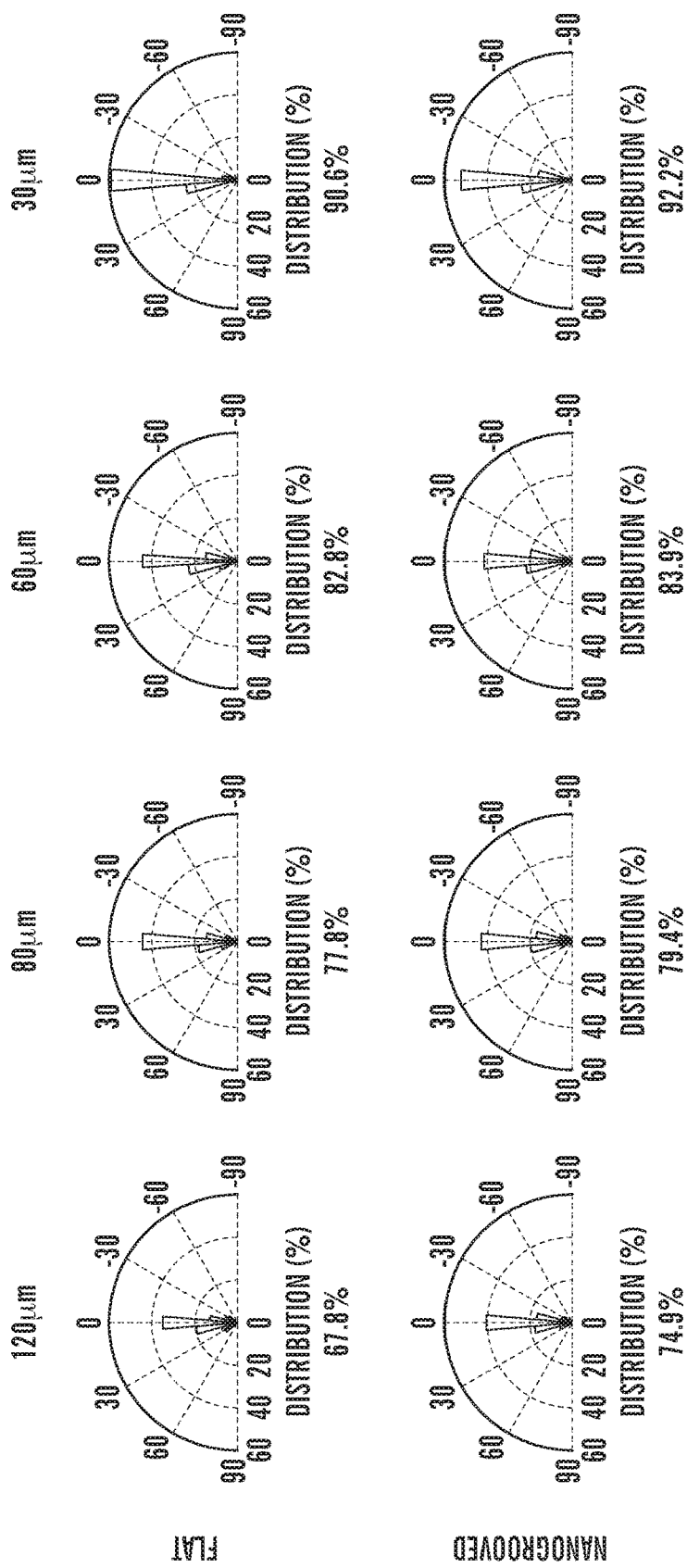

To further explore the influence of multiscale cues imparted by the ECM-coated migration pathways, nanogrooved substrates were created with different microscale migration pathway widths by using PDMS microstamp-assisted plasma lithography. This enabled the inventors to create spatial migration pathway patterning on the surface of the nanotextured substrate that mimics the characteristic heterogeneity found within the normal and diseased in vivo tissue environment[67]. As an exemplary example, the inventors generated a nanopatterned substrate with migration pathways which were 10 mm long straight lines of collagen coated on the nanogrooves that had 30, 60, 80, and 120 μm widths, in order to elucidate the influence of the microscale spatial cue in the width direction. Cells were plated in the cell loading region as described above and migrated only on the micropatterned ECM-coated migration pathways with defined geometry. Consistent with the inventors' previous findings (FIG. 2), the cells migrated only within the ECM-coated migration pathways without a remarkable difference in migration speed between cells in the middle and at the edge of the migration pathway, and did not migrate into the surrounding hydrophobic regions either side of the migration pathways during experiment. For quantitative analysis of cell migration, the paths of individual migrating PIK3CA knockin cells on flat PDMS substrates along the length of the migration pathways were assessed for 12 hours using time-lapse imaging (N=36, Δt=20 min) to measure trajectories including migration direction and distance (FIG. 3B). The results demonstrate that as the width of the micropattern of the migration pathway become narrower (from 120 μm to 30 μm), the total migration distance of the cells along the migration pathway for all conditions becomes longer.

Figure 4A:
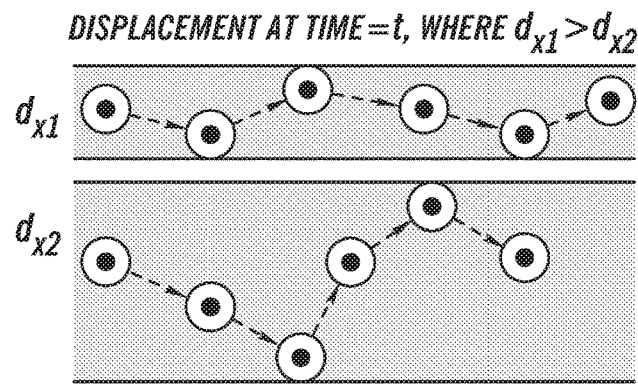
FIGS. 4A-4C shows directed migration from microscale geometric constraints conforms to diffusion anisotropy behavior.

Therefore, the inventors have discovered that the increase in migration distance as the width of the micropatterned migration pathway becomes narrower is consistent with confined anisotropic diffusion behavior of cells, and as such, the observed changes in cell migration behavior as a function of micropattern width occurs by a random walk diffusion anisotropy model. The inventors developed a stochastic model where cells undergoing a random walk are constrained by boundaries (i.e. width of an ECM-coated migration pathway or channel and cells behind the leading edge). As expected, as the migration pathway width becomes much larger than the migration persistence length, the model predicts classic random 2D migration behavior for cells undergoing a random walk (FIG. 4A bottom). Likewise, as the width becomes relatively small, the output approaches a purely 1D directed migration regime (FIG. 4A top). Here, the model predicted that as migration pathway width decreases, the migration distance would vastly increase, which is consistent with experimental data (see FIG. 4C for an example of shifting the geometric constraint by a factor of 4). As such, model predictions strongly suggest that the inventors' discovery of increased cell migration by confined microscale directed migration cues is the result, at least in part, of a thermodynamically driven random motility process directed by the geometrically constrained environment.

Example 4

Microscale Extrinsic Guidance Cues (i.e., Migration Pathways) and Cell Intrinsic Cues Work Synergistically to Promote Migration.

Figure 4B:
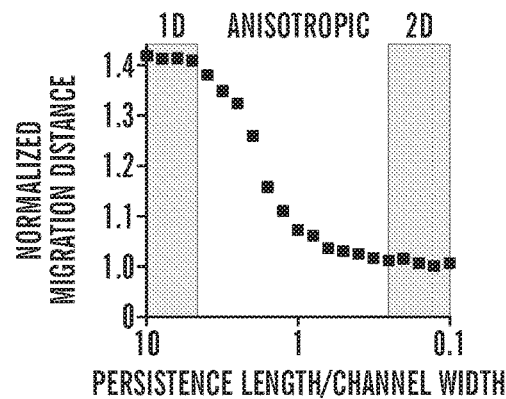
Figure 4C:
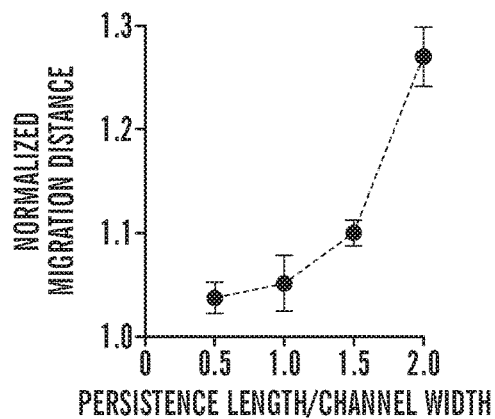

To define the collective impact of (i) micron scale constrained migration cues, (ii) nanoscale contact guidance cues, and (iii) intrinsic cellular perturbations, the inventors generated micropatterns of ECM-coated migration pathways of varying widths possessing flat or nanogrooved surfaces and quantified the response to the cues in parental and PIK3CA MCF-10A lines. On nanotextured surfaces, cells migrated only on the ECM-coated migration pathways, with no remarkable difference in migration speed between cells in the middle and at the edge of the migration pathways, consistent with earlier experiments. In an exemplary embodiment, the nanotopography dimensions for contact guidance were as follows: 800 nm ridges, 800 nm grooves, with a height of 600 nm, as shown in FIGS. 1 and 2. For quantitative analysis of cell migration, the paths of individual migrating PIK3CA knockin cells on flat and nanogrooved PDMS substrates along the ECM-coated migration pathways were tracked with time-lapse imaging (N=36, Δt=20 min over 12 hours) to measure trajectories including migration direction and distance (FIGS. 3B and C). Consistent with the inventors results for flat substrates (FIG. 4B top), the inventors demonstrated that, on a nanogrooved PDMS substrate, as the migration pathway width become narrower (from 120 μm to 30 μm), the total migration distance of the cells along the migration pathways for all conditions becomes longer (FIG. 4B bottom). The inventors also discovered that the migration speed increased as migration pathway width decreased or narrowed (FIG. 3A and data not shown). Furthermore, the inventors discovered that the addition of nanoscale contact guidance cues (e.g., the nanogrooved surface) within migration pathways promotes collective migration, albeit quite modestly, particularly relative to the robust increase in migration observed in wide migration pathways (i.e. FIG. 2). Thus, to further assess the influence of nanoscale contact guidance cues (e.g., nanogrooved surface) within each constrained ECM-coated migration pathway (ranging from 30-120 µm widths), the direction of individual migration paths were quantified. The inventors analyzed the percentage of knockin cells with migration directions within ±15 degrees from the ECM-coated migration pathway, representing highly persistent directionality of the migration (FIG. 3). Therefore, the inventors have demonstrated that as the width of ECM-coated migration pathway become narrower from 120 µm to 30 µm, on both flat or nanogrooved surface substrates, migrating cells display an increase in directionality along the length of the migration pathway, consistent with prediction from the diffusion anisotropy model (FIG. 4).

However, although nanotopography enhances directed migration, the increase in the straight directionality between flat and nanogrooved substrates when the width of ECM-coated migration pathway becomes narrower than 80 µm is quite modest (FIG. 4D). Therefore, the inventors have discovered that as the ECM-coated migration pathway width diminishes, micronscale directed migration cues become more dominant, appearing to exceed the influence of nanotopography induced contact guidance for collective cell migration in this context.

Figures 5A, 5B, 5C, 5D, 5E, 5F:
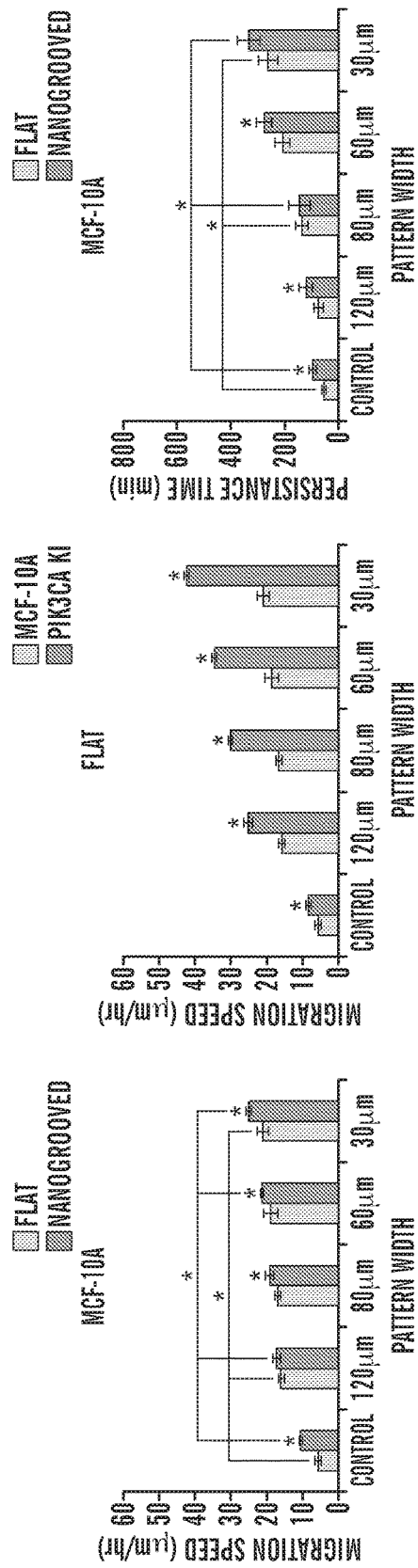
FIGS. 5A-5F show cellular migration speeds and directional persistence time in response to micropatterning of ECM pattern geometry.
Figure 6B:
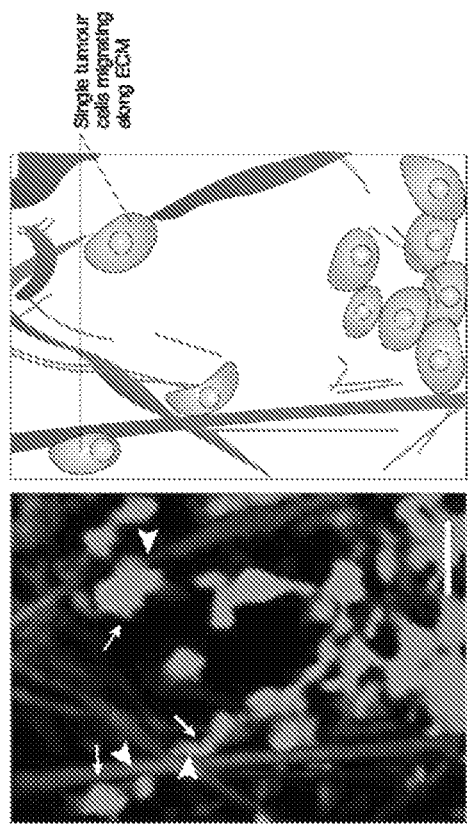
FIGS. 6A-6C show anatomical features of highly oriented ECM in various tissues.
Figure 6A:
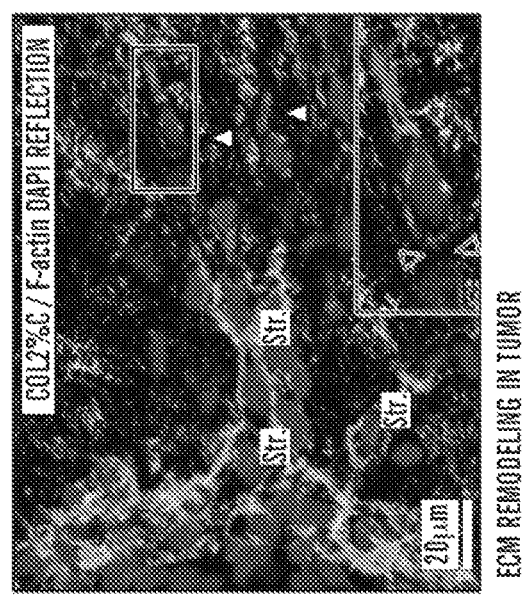
Figure 6C:
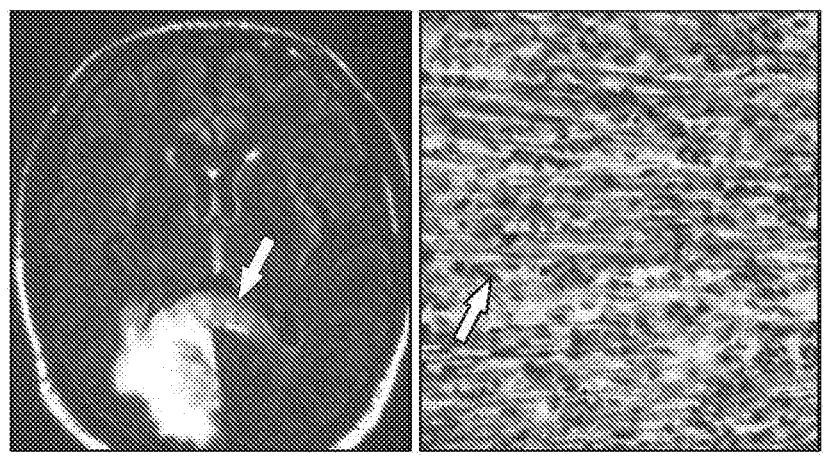
Figure 7:
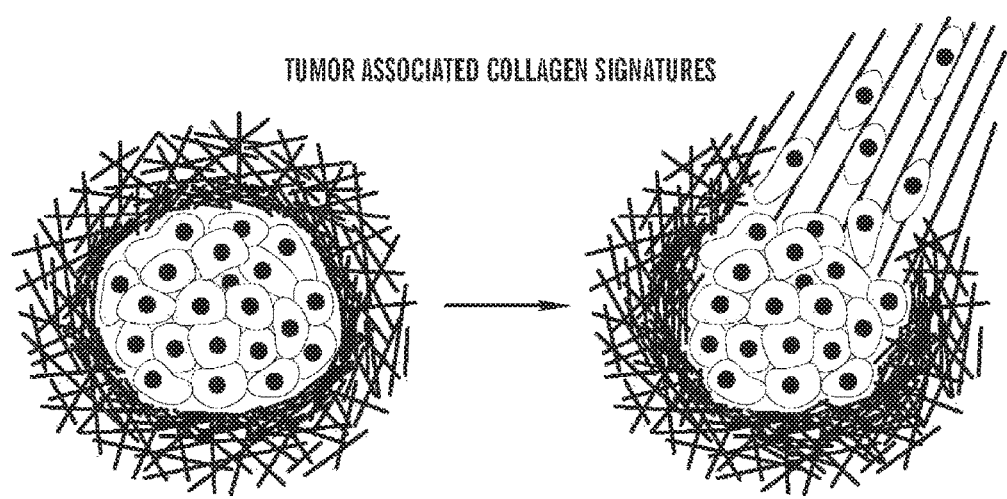
FIG. 7 is a schematic of tumor associated collagen signatures, whereby the structural organization of the collagen forms a tumor niche and allows migration of individual tumor cells from the collagen tumor microniche.

To further explore the influence of ECM-coated migration pattern cues and contemporaneous intrinsic cues, the inventors compared parental and PIK3CA cells within migration pathways of different width containing either a flat or nanogrooved surface. By calculating the root mean-square displacement (MSD) of the cell path of each migrating cell, the inventors obtained migration speed and persistence time from the persistent random walk model for both cell populations subjected to different widths of the ECM-coated migration pathway (FIG. 5). Consistent with the previous results (FIG. 2), the migration speed and the persistence time of both cell types varied with the width of the ECM-coated migration pathway (FIGS. 5A and B), where decreasing width resulted in an increased migration speed. Yet, while nanoscale contact guidance cues again promoted migration speed, the impact was modest for both cell types in narrow ECM-coated migration pathways (FIGS. 5A and B), demonstrating that microscale directed migration cues are more dominant for both cell types as the pattern width approaches about 80 µm, or alternatively, a few cell diameters. Indeed, in contrast to wide ECM-coated migration pathways (control groups), both wild type (MCF-10A) and knockin cells (PIK3CA) on nanogrooved substrates migrated a modest 0.14 (±0.03) times faster on average than their migration on flat substrates for all migration pathway widths (≤120 µm), but do display a significant (0.03<p<0.05) or trending (0.05<p<0.07) increase at each migration pathway width, indicating a synergistic influence of micro- and nano-scale cues. The difference in migration speed between on flat and nanogrooved substrates at each migration pathway width, regardless of the cell type, was from at most 3.1 (±2.1) µm/hr to 3.8 (±1.6) µm/hr as the migration pathway width was decreased from 120 µm to 30 µm. In contrast, the impact of micronscale directed migration cues resulted in a more substantial increase in migration—for instance, the migration of MCF-10A and PIK3CA knockin cells in larger migration pathways (i.e. relatively wide patterns) shifted from 5.6 µm/hr and 8.6 µm/hr respectively, to >20 µm/hr and >40 µm/hr at 30 µm ECM-coated migration pathway widths. Yet, cell migration along the ECM-coated migration pathway on both flat and nanogrooved substrates was up to ×5.6 times faster due to the synergistic effect of nanotopography surface and micropatterning of the migration pathways as compared to conditions that lack both the nanotopography and ECM micropatterns. Furthermore, migration speed of the oncogenic PIK3CA knockin cells on both flat and nanogrooved substrates were 97% faster than their wild type cells on average (FIGS. 5C and D). Consequently, the inventors have discovered that the oncogenic breast epithelial cells more sensitively respond to microscale cues, i.e., width of the ECM-coated migration pathways in a geometry-dependent manner, and there is a statistically significant difference (p<0.001) in migration speed among the two cell types (i.e., MCF-10A) and knockin cells (PIK3CA)) on all ECM patterns (FIGS. 5C and D).

The persistence time also varied with the presence of nanotopography and ECM micropatterns of various widths. Increases in directional persistence of MCF-10A wild type cells in the presence of nanogrooves were modest, but showed a statistically significant or trending difference when the width of the ECM-coated migration pathway was narrowed, consistent with migration speed data (FIG. 5E). In stark contradistinction, the persistence time of oncogenic PIK3CA knockin cells in the presence of the nanogroove contact guidance cues showed a strong significant increase, as well as a dependence on the width of the ECM-coated migration pathway, rising from ~207 min at 120 µm to ~543 min at 30 µm, and showed profoundly straightforward movement without any significant turns (FIG. 5F). These findings demonstrate that oncogenic PIK3CA knockin cells migrate for longer time without significant changes in their migratory direction within the ECM-coated migration pathways compared to their wild type cells, and have an increased straightforward directionality. These results provide additional support of the inventors' discovery that geometric confinement, such as by use of ECM-coated migration pathways modulates directional migration, and that oncogenic PIK3CA knockin cells are more sensitive to the microscale cues and pattern geometry as well as to substrate nanotopography. Thus, the inventors have surprisingly discovered that in oncogenic cell populations, there is a profound synergy between extracellular micro- and nano scale migration cues and intrinsic cell signaling, that drives migration in a way that vastly outperforms wild type cells or any of the extracellular guidance cues in isolation.

The inventors have also demonstrated migration of normal epithelial cells on the biomimetic culture platform (data not shown). In particular, the inventors have demonstrated that normal breast epithelial cells migrate on the nanogrooved migration pathways (data not shown). Using an Akt-PH marker, the inventors have demonstrated its transloation to the leading edge of migrating melanoma cells, whereas Akt-PH remains cytoplasmic in non-leading melanoma cells (data not shown) indicating organization of the microtubules in migrating melanoma cells. Additionally, the inventors have demonstrated, using YFP-labeled microtubules in MDCK epithelial cells, that microtubule actin fibers are orientated and organized in the direction of the nanogrooves in leading migrating MDCK epithelial cells (data not shown).

The inventors have also demonstrated that migration of different tumor cell types, e.g., benign and metastatic melanoma cells differ on the biomimetic culture platform. For instance, a phenotypic difference between malignant (1205Lu) and benign (WM35) melanoma/skin cells was detected in 3D collagen culture (data not shown). In particular, benign cells (WM35 or Mel 1) were determined not to undergo collagen I re-organization, whereas malignant melanoma cells (1205Lu or Mel 10) were demonstrated to have an increased collagen I re-organization, with a polarized organization of Collagen-I fibers adjacent to elongated Mel 10 cells, demonstrating that Mel 10 cells utilize collagen I fibers for migration and metastatic potential (data not shown). Accordingly, the BCP as disclosed herein can be used to identify differential cell mechanics properties of melanoma cells during malignant progression. For example, the inventors also assessed the traction force microscopy measurements of non-malignant (benign) Mel 1 cells (WM35), and malignant melanoma Mel 10 cells (1205 Lu), and demonstrated that malignant melanoma cells have higher contractile force, and have extended fibrils as compared to non-malignant (benign) Mel 1 cells (data not shown). Furthermore, the inventors measured the movement of the non-malignant (benign) Mel 1 cells (WM35) and malignant melanoma Mel 10 cells (1205 Lu) (IG0I (Pa/m)) along the X- and Y-axis of flat and nanotextured substrates, and discovered that both cell types migrate further along the x-axis of nanotextured substrates (i.e., in the same direction of the direction of the nanogrooves) than flat substrates, and that metastatic Mel 10 cells are stiffer and exercise stronger forces than non-metastatic Mel 1 cells and use the higher forces to form or reorganize the surrounding matrix fibers (data not shown).

Example 5

In summary, the inventors have engineered a biomimetic platform using (i) UV-assisted capillary force lithography for surface nanopatterning, and (ii) plasma lithography patterning for ECM-coated micropatterns, to provide multiscale directed migration cues to guide cell migration. This system provides both extracellular and intracellular guidance cues, and permits one to assess both extracellular and/or intracellular perturbations and the parsing out of their relative impact. The inventors herein have demonstrated that the plasma lithographic technique is an effective approach for creating geometric surface patterns of an ECM-coating, such as ECM-coated migration pathways, based on selective plasma functionalization of the substrate with long term stability that effectively coats a nanopatterned substrate. Thus, the inventors biomimetic culture platform disclosed herein provides a highly effective and reliable means to expose epithelial cells to micron and nano scale directed migration cues. Furthermore, although the Examples herein have focused on mammary gland cells, as well as breast cancer micro/nanoenvironment, the versatile nature of these biomimetic culture platforms can be utilized to explore the behavior of many different cell types, such as cancer cells or invasive tumor cells, or mimic other physiologically relevant tissue microenvironments such as, for example, blood vessels, myelinated fibers, or the white matter tracks that brain and spinal cord glioma cells have been shown to migrate along.

Likewise, the integrative nature of the biomimetic culture platform disclosed herein, and the ability incorporate different surface chemistries (e.g., different ECM components and/or different geometric patterns of ECM-coatings), as well as different nanotopology surface geometries, permits one of ordinary skill in the art to investigate additional factors, such as, for example, the synergistic effects of protein ligand mediated migration with topographic guidance. It is also envisioned that the biomimetic culture platform can be modified by mechanical factors, such as mechanical deformation, as well as gradients in substrate stiffness, fluid shear stress, and chemical gradients to further decipher complex cell migratory behavior. Thus, therein the inventors present a robust biomimetic culture platform that can be employed in its current form, or easily adapted, to address fundamental questions of how the environment influences cell motility as a function of the underlying genetics and associated proteome.

The inventors have demonstrated herein, using straight edged migration pathways (i.e. effectively very wide migration pathways; FIG. 2), contact guidance from nanoscale cues was prominent, giving rise to significantly increased speed and persistence time with straightforward directionality in the direction of the nanogrooves versus migration on a flat surface. In addition, the nanoscale contact guidance cues resulted in increased directionality of migration, collectively resulting in vastly enhanced distance of migration within a set time window. Furthermore, the inventors using the biomimetic culture platform were able to identify microscale directed migration cues that also profoundly influence collective cell migration. As pattern width (analogous to channel width) of the migration pathways decreased to 120 µm, cell migration increased robustly (i.e. FIGS. 3 and 5) as compared to no constraints (e.g., no migration pathways) or a wide environments (FIG. 2 and control groups in FIG. 5). Furthermore, as width of the migration pathway was decreased from 120 µm to 80 µm, 60 µm, and ultimately 30 µm, cell migration significantly increased—a behavior consistent with diffusion in a constrained environment (i.e. diffusion anisotropy for cells undergoing a random walk). Interestingly, these results contrast findings in Madin-Darby canine kidney (MDCK) cells in channels spanning 100 to 300 µm[66], but are consistent with increased migration of MDCK cells as pattern widths decrease from 400 down to 100 and then particularly at 20 µm[67]. Accordingly, the inventors have discovered that directed migration from microscale cues is dominant when the constraint is in a range below approximately 100 µm in width. Of course, however, this dimension is relative to cell size and the persistence length of the migrating cell, as supported by the inventors' diffusion anisotropy model, described herein. Importantly, the biomimetic culture platform disclosed herein is different from prior platforms in that it combines both micropatterning of the ECM-coated migration pathways, in addition to nanogrooved surface topology, there the nanogrooves provide precise and specific contact guidance cues, while the ECM-coated migration pathways provide microscale migratory cues. In the absence of the ECM-coated migration pathways, cells cultured on a nanogrooved surface have increased migration as compared to their culture on a flat surface, and their migration is modestly increased with decreasing width of the ECM-coated migration pathways. Therefore, the inventors have discovered that these cues (microscale and/or nanoscale) are drivers that profoundly dictate different diffusion coefficients (i.e. motility coefficients in this context) in different directions as is readily illustrated by considering Fick's 1$^{st}$ law diffusion behavior in multiple dimensions where the diffusive flux ($J_i$) is represented as $$I_i = -D_{ij}\frac{\partial C}{\partial x_i}$$

with cell concentration C and the diffusion coefficient $D_{ij}$ being non-isotropic as represented by a symmetric tensor to account directional dependence of the diffusion coefficient, i.e.

$$D_{ij} = \begin{matrix} D_{xx} & D_{xy} & D_{xz} \\ D_{yx} & D_{yy} & D_{yz} \\ D_{zx} & D_{zy} & D_{zz} \end{matrix}$$

where for the 2D problem this would reduce and account for anisotropy in the x and y directions. This is analogous to prior reports describing directional dependent random walk[68] and biased migration through an anisotropic diffusion parameter proportional to the ratio of the diffusion coefficient in two orthogonal directions (e.g. x and y) that can account for directed migration effects, including contact guidance[69]. This approach was recently corroborated to describe separate cell types undergoing 3D migration in nonhomogeneous environments[70]. Likewise, the inventors have demonstrated that the additive effect of nanoscale contact guidance cues in addition to the microscale migration cues, further promotes migration within a confined migration pathway (i.e. Fickian diffusion) and such enhanced migration may be conceptualized as a convective driving force ($J_c=C_iv$, where v is velocity) additive to the diffusive flux behavior $$J_i = D_{ij}\nabla C_i + C_i v$$

In this context, the convective driving force would account for fundamental changes in the propulsion force resulting from alterations in the mechanics of cell migration resulting from contact guidance architectures. Furthermore, the ratio of these terms may have implications for characterizing the dominant cues through a dimensionless parameter, as would be the case for dominant micron scale directed migration cues in narrow channels (e.g. FIGS. 3 and 5), but much less so for the case of effectively wide channels (e.g. FIG. 2) where nanoscale contact guidance cues impart a much more substantial increase in migration.

PI3K pathway signaling regulates numerous critical behaviors required of transformed cells, including growth, survival and invasion[22,23], and it is frequently dysregulated in numerous malignancies[17-19], making it an attractive target for cancer therapy. Further, in addition to therapeutic exploitation of its well-described downstream effectors (e.g. AKT, mTOR etc.), characterizing its motility dynamics in response to particular features found in the TME may open new avenues to identify novel therapeutic vulnerabilities in PI3K mutant cells. Here, the inventors demonstrate that mutant PIK3CA expression resulted in significantly increased cell migration versus parental mutant PIK3CA cells under baseline (i.e. wide and flat) conditions. In addition, exposure to nanoscale contact guidance cues significantly promoted migration of mutant cells. Surprisingly, parental MCF-10A cells showed only modestly increase in migration with the addition of nanoscale contact guidance cues on narrow migration pathways. In contrast and surprisingly, oncogenic cells display a remarkable synergy of the additive benefits of microscale cues from the migration pathway, and nanoscale nanogroove topology, and PI3K signaling. As a result, these mutant PIK3CA cells vastly outperformed wild type parental MCF-10A cells under any of the migration pathway widths, demonstrating that oncogenic breast epithelial cells are more heavily influenced by multiscale directed migration cues in the environment. Indeed, the inventors have demonstrated that the activation of a single oncogene may confer a distinct advantage for migration through a given ECM architecture and this response likely contributes to the metastatic potential of carcinoma cells. Accordingly, the biomimetic culture platform disclosed herein can be used to identify cells with a metastatic potential. Further, the inventors have also discovered that oncogene activation resulted in a fundamental change in adhesion-mediated signaling and the dynamic cytoskeletal remodeling underlying sustained locomotion through persistent protrusion of leading edge lamellipodia over time. In fact, these oncogenic cells display vastly increased persistence, as well increased speed, and a profoundly increased migration. Certainly, the biomimetic culture platform disclosed herein is useful for clarifying the interrelationships between the multiscale directed migration cues and the underlying intrinsic cell structure and signal transduction in a quantitative assay, which is useful to aid the understanding of the fundamental mechanisms regulating normal and cancerous cell migration, and migration of metastatic cells, and can be used to identify agents which inhibit migration of such metastatic cells.

REFERENCES

All references cited in the specification and their Examples are incorporated in their entirety herein by reference.

[1] Yamada K M, Cukierman E. Modeling tissue morphogenesis and cancer in 3D. Cell. 2007; 130:601-10.
[2] Provenzano P P, Eliceiri K W, Keely P J. Shining new light on 3D cell motility and the metastatic process. Trends in cell biology. 2009; 19:638-48.
[3] Midwood K S, Williams L V, Schwarzbauer J E. Tissue repair and the dynamics of the extracellular matrix. The international journal of biochemistry & cell biology. 2004; 36:1031-7.
[4] Daley W P, Yamada K M. ECM-modulated cellular dynamics as a driving force for tissue morphogenesis. Current opinion in genetics & development. 2013; 23:408-14.
[5] Ingman W V, Wyckoff J, Gouon-Evans V, Condeelis J, Pollard J W. Macrophages promote collagen fibrillogenesis around terminal end buds of the developing mammary gland. Developmental dynamics: an official publication of the American Association of Anatomists. 2006; 235:3222-9.
[6] Provenzano P P, Eliceiri K W, Campbell J M, Inman D R, White J G, Keely P J. Collagen reorganization at the tumor-stromal interface facilitates local invasion. BMC medicine. 2006; 4:38.
[7] Schedin P, Keely P J. Mammary gland ECM remodeling, stiffness, and mechanosignaling in normal development and tumor progression. Cold Spring Harbor perspectives in biology. 2011; 3:a003228.
[8] Guarino M. Epithelial-mesenchymal transition and tumour invasion. The international journal of biochemistry & cell biology. 2007; 39:2153-60.
[9] Kumar S, Weaver V M. Mechanics, malignancy, and metastasis: the force journey of a tumor cell. Cancer metastasis reviews. 2009; 28:113-27.
[10] Pathak A, Kumar S. Transforming potential and matrix stiffness co-regulate confinement sensitivity of tumor cell migration. Integrative biology: quantitative biosciences from nano to macro. 2013; 5:1067-75.

[11] Petrie R J, Doyle A D, Yamada K M. Random versus directionally persistent cell migration. Nature reviews Molecular cell biology. 2009; 10:538-49.

[12] Charras G, Sahai E. Physical influences of the extracellular environment on cell migration. Nature reviews Molecular cell biology. 2014; 15:813-24.

[13] Provenzano P P, Inman D R, Eliceiri K W, Knittel J G, Yan L, Rueden C T, et al. Collagen density promotes mammary tumor initiation and progression. BMC medicine. 2008; 6:11.

[14] Provenzano P P, Inman D R, Eliceiri K W, Trier S M, Keely P J. Contact guidance mediated three-dimensional cell migration is regulated by Rho/ROCK-dependent matrix reorganization. Biophysical journal. 2008; 95:5374-84.

[15] Conklin M W, Eickhoff J C, Riching K M, Pehlke C A, Eliceiri K W, Provenzano P P, et al. Aligned collagen is a prognostic signature for survival in human breast carcinoma. The American journal of pathology. 2011; 178:1221-32.

[16] Goetz J G, Minguet S, Navarro-Lerida I, Lazcano J J, Samaniego R, Calvo E, et al. Biomechanical remodeling of the microenvironment by stromal caveolin-1 favors tumor invasion and metastasis. Cell. 2011; 146:148-63.

[17] Samuels Y, Wang Z, Bardelli A, Silliman N, Ptak J, Szabo S, et al. High frequency of mutations of the PIK3CA gene in human cancers. Science. 2004; 304:554.

[18] Bachman K E, Argani P, Samuels Y, Silliman N, Ptak J, Szabo S, et al. The PIK3CA gene is mutated with high frequency in human breast cancers. Cancer biology & therapy. 2004; 3:772-5.

[19] Karakas B, Bachman K E, Park B H. Mutation of the PIK3CA oncogene in human cancers. British journal of cancer. 2006; 94:455-9.

[20] Isakoff S J, Engelman J A, Irie H Y, Luo J, Brachmann S M, Pearline R V, et al. Breast cancer-associated PIK3CA mutations are oncogenic in mammary epithelial cells. Cancer research. 2005; 65:10992-1000.

[21] Bader A G, Kang S, Vogt P K. Cancer-specific mutations in PIK3CA are oncogenic in vivo. Proceedings of the National Academy of Sciences of the United States of America. 2006; 103:1475-9.

[22] Gustin J P, Karakas B, Weiss M B, Abukhdeir A M, Lauring J, Garay J P, et al. Knockin of mutant PIK3CA activates multiple oncogenic pathways. Proceedings of the National Academy of Sciences of the United States of America. 2009; 106:2835-40.

[23] Arcaro A, Guerreiro A S. The phosphoinositide 3-kinase pathway in human cancer: genetic alterations and therapeutic implications. Current genomics. 2007; 8:271-306.

[24] Higgins M J, Jelovac D, Barnathan E, Blair B, Slater S, Powers P, et al. Detection of Tumor PIK3CA Status in Metastatic Breast Cancer Using Peripheral Blood. Clin Cancer Res. 2012; 18:3462-9.

[25] Condeelis J, Segall J E. Intravital imaging of cell movement in tumours. Nature reviews Cancer. 2003; 3:921-30.

[26] Kim D H, Wong P K, Park J, Levchenko A, Sun Y. Microengineered platforms for cell mechanobiology. Annual review of biomedical engineering. 2009; 11:203-33.

[27] Kim D H, Kim P, Song I, Cha J M, Lee S H, Kim B, et al. Guided three-dimensional growth of functional cardiomyocytes on polyethylene glycol nanostructures. Langmuir: the ACS journal of surfaces and colloids. 2006; 22:5419-26.

[28] Kim P, Kim D H, Kim B, Choi S K, Lee S H, Khademhosseini A, et al. Fabrication of nanostructures of polyethylene glycol for applications to protein adsorption and cell adhesion. Nanotechnology. 2005; 16:2420-6.

[29] Peyton S R, Kim P D, Ghajar C M, Seliktar D, Putnam A J. The effects of matrix stiffness and RhoA on the phenotypic plasticity of smooth muscle cells in a 3-D biosynthetic hydrogel system. Biomaterials. 2008; 29:2597-607.

[30] Dickinson L E, Lutgebaucks C, Lewis D M, Gerecht S. Patterning microscale extracellular matrices to study endothelial and cancer cell interactions in vitro. Lab Chip. 2012; 12:4244-8.

[31] Liu N, Liang W F, Liu L Q, Wang Y C, Mai J D, Lee G B, et al. Extracellular-controlled breast cancer cell formation and growth using non-UV patterned hydrogels via optically-induced electrokinetics. Lab Chip. 2014; 14:1367-76.

[32] Kim P, Yuan A, Nam K H, Jiao A, Kim D H. Fabrication of poly(ethylene glycol): gelatin methacrylate composite nanostructures with tunable stiffness and degradation for vascular tissue engineering. Biofabrication. 2014; 6:024112.

[33] Song M, Uhrich K E. Optimal micropattern dimensions enhance neurite outgrowth rates, lengths, and orientations. Annals of biomedical engineering. 2007; 35:1812-20.

[34] Su J, Jiang X, Welsch R, Whitesides G M, So P T. Geometric confinement influences cellular mechanical properties I—adhesion area dependence. Molecular & cellular biomechanics: MCB. 2007; 4:87-104.

[35] Ruiz S A, Chen C S. Emergence of Patterned Stem Cell Differentiation Within Multicellular Structures. Stem Cells. 2008; 26:2921-7.

[36] Reyes D R, Perruccio E M, Becerra S P, Locascio L E, Gaitan M. Micropatterning neuronal cells on polyelectrolyte multilayers. Langmuir: the ACS journal of surfaces and colloids. 2004; 20:8805-11.

[37] Nam Y, Chang J, Khatami D, Brewer G J, Wheeler B C. Patterning to enhance activity of cultured neuronal networks. IEE proceedings Nanobiotechnology. 2004; 151:109-15.

[38] Massobrio P, Martinoia S. Modelling small-patterned neuronal networks coupled to microelectrode arrays. J Neural Eng. 2008; 5:350-9.

[39] Rhee S W, Taylor A M, Tu C H, Cribbs D H, Cotman C W, Jeon N L. Patterned cell culture inside microfluidic devices. Lab Chip. 2005; 5:102-7.

[40] Gross P G, Kartalov E P, Scherer A, Weiner L P. Applications of microfluidics for neuronal studies. J Neurol Sci. 2007; 252:135-43.

[41] Kim J D, Choi J S, Kim B S, Choi Y C, Cho Y W. Piezoelectric inkjet printing of polymers: Stem cell patterning on polymer substrates. Polymer. 2010; 51:2147-54.

[42] Junkin M, Leung S L, Yang Y L, Lu Y, Volmering J, Wong P K. Plasma Lithography Surface Patterning for Creation of Cell Networks. Jove-J Vis Exp. 2011.

[43] Falconnet D, Csucs G, Grandin H M, Textor M. Surface engineering approaches to micropattern surfaces for cell-based assays. Biomaterials. 2006; 27:3044-63.

[44] Chang W C, Sretavan D W. Novel High-Resolution Micropatterning for Neuron Culture Using Polylysine Adsorption on a Cell Repellant, Plasma-Polymerized Background. Langmuir: the ACS journal of surfaces and colloids. 2008; 24:13048-57.
[45] Zhang J, Venkataramani S, Xu H, Song Y K, Song H K, Palmore G T, et al. Combined topographical and chemical micropatterns for templating neuronal networks. Biomaterials. 2006; 27:5734-9.
[46] Aubin H, Nichol J W, Hutson C B, Bae H, Sieminski A L, Cropek D M, et al. Directed 3D cell alignment and elongation in microengineered hydrogels. Biomaterials. 2010; 31:6941-51.
[47] Nelson C M, Jean R P, Tan J L, Liu W F, Sniadecki N J, Spector A A, et al. Emergent patterns of growth controlled by multicellular form and mechanics. Proceedings of the National Academy of Sciences of the United States of America. 2005; 102:11594-9.
[48] Thery M. Micropatterning as a tool to decipher cell morphogenesis and functions. J Cell Sci. 2010; 123:4201-13.
[49] Keyes J, Junkin M, Cappello J, Wu X Y, Wong P K. Evaporation-induced assembly of biomimetic polypeptides. Appl Phys Lett. 2008; 93.
[50] Junkin M, Watson J, Geest J P V, Wong P K. Template-Guided Self-Assembly of Colloidal Quantum Dots Using Plasma Lithography. Adv Mater. 2009; 21:1247-+.
[51] Kim D H, Lipke E A, Kim P, Cheong R, Thompson S, Delannoy M, et al. Nanoscale cues regulate the structure and function of macroscopic cardiac tissue constructs. Proceedings of the National Academy of Sciences of the United States of America. 2010; 107:565-70.
[52] Suh K Y, Seong J, Khademhosseini A, Laibinis P E, Langer R. A simple soft lithographic route to fabrication of poly(ethylene glycol) microstructures for protein and cell patterning. Biomaterials. 2004; 25:557-63.
[53] Khademhosseini A, Suh K Y, Jon S, Eng G, Yeh J, Chen G J, et al. A soft lithographic approach to fabricate patterned microfluidic channels. Analytical chemistry. 2004; 76:3675-81.
[54] Lee S K, Jung J M, Lee J S, Jung H T. Fabrication of complex patterns with a wide range of feature sizes from a single line prepattern by successive application of capillary force lithography. Langmuir: the ACS journal of surfaces and colloids. 2010; 26:14359-63.
[55] Jeong H E, Kwak R, Khademhosseini A, Suh K Y. UV-assisted capillary force lithography for engineering biomimetic multiscale hierarchical structures: From lotus leaf to gecko foot hairs. Nanoscale. 2009; 1:331-8.
[56] Suh K Y, Kim Y S, Lee H H. Capillary force lithography. Adv Mater. 2001; 13:1386-9.
[57] Bessette D C, Tilch E, Seidens T, Quinn M C, Wiegmans A P, Shi W, et al. Using the MCF10A/MCF10CA1a Breast Cancer Progression Cell Line Model to Investigate the Effect of Active, Mutant Forms of EGFR in Breast Cancer Development and Treatment Using Gefitinib. PloS one. 2015; 10:e0125232.
[58] Ramljak D, Romanczyk L J, Metheny-Barlow L J, Thompson N, Knezevic V, Galperin M, et al. Pentameric procyanidin from *Theobroma cacao* selectively inhibits growth of human breast cancer cells. Molecular cancer therapeutics. 2005; 4:537-46.
[59] Kim H N, Hong Y, Kim M S, Kim S M, Suh K Y. Effect of orientation and density of nanotopography in dermal wound healing. Biomaterials. 2012; 33:8782-92.
[60] Boguna M, Porra J M, Masoliver J. Persistent random walk model for transport through thin slabs. Phys Rev E. 1999; 59:6517-26.
[61] Codling E A, Plank M J, Benhamou S. Random walk models in biology. J R Soc Interface. 2008; 5:813-34.
[62] Harms B D, Bassi G M, Horwitz A R, Lauffenburger D A. Directional persistence of EGF-Induced cell migration is associated with stabilization of lamellipodial protrusions. Biophysical journal. 2005; 88:1479-88.
[63] Dunn G A. Characterising a kinesis response: time averaged measures of cell speed and directional persistence. Agents and actions Supplements. 1983; 12:14-33.
[64] Othmer H G, Dunbar S R, Alt W. Models of dispersal in biological systems. Journal of mathematical biology. 1988; 26:263-98.
[65] Dickinson R B, Tranquillo R T. Optimal Estimation of Cell-Movement Indexes from the Statistical-Analysis of Cell Tracking Data. Aiche J. 1993; 39:1995-2010.
[66] Marel A K, Zorn M, Klingner C, Wedlich-Soldner R, Frey E, Radler J O. Flow and diffusion in channel-guided cell migration. Biophysical journal. 2014; 107:1054-64.
[67] Vedula S R, Leong M C, Lai T L, Hersen P, Kabla A J, Lim C T, et al. Emerging modes of collective cell migration induced by geometrical constraints. Proceedings of the National Academy of Sciences of the United States of America. 2012; 109:12974-9.
[68] Matthes T, Gruler H. Analysis of cell locomotion. Contact guidance of human polymorphonuclear leukocytes. European biophysics journal: EBJ. 1988; 15:343-57.
[69] Dickinson R B, Guido S, Tranquillo R T. Biased cell migration of fibroblasts exhibiting contact guidance in oriented collagen gels. Annals of biomedical engineering. 1994; 22:342-56.
[70] Wu P H, Giri A, Sun S X, Wirtz D. Three-dimensional cell migration does not follow a random walk. Proceedings of the National Academy of Sciences of the United States of America. 2014; 111:3949-54.
[71] Xia Y N, Whitesides G M. Soft lithography. Annu Rev Mater Sci. 1998; 28:153-84.
[72] Gates B D, Xu Q B, Stewart M, Ryan D, Willson C G, Whitesides G M. New approaches to nanofabrication: Molding, printing, and other techniques. Chem Rev. 2005; 105:1171-96.
[73] Junkin M, Wong P K. Probing cell migration in confined environments by plasma lithography. Biomaterials. 2011; 32:1848-55.
[74] Konishi H, Lauring J, Garay J P, Karakas B, Abukhdeir A M, Gustin J P, et al. A PCR-based high-throughput screen with multiround sample pooling: application to somatic cell gene targeting. Nat Protoc. 2007; 2:2865-74.
[75] Konishi H, Karakas B, Abukhdeir A M, Lauring J, Gustin J P, Garay J P, et al. Knock-in of mutant K-ras in nontumorigenic human epithelial cells as a new model for studying K-ras-mediated transformation. Cancer research. 2007; 67:8460-7.

The invention claimed is:
1. An array for assessing cell migration comprising:
 a. a nanopatterned substrate comprising parallel grooves and ridges, wherein the groove width is between 200 nm to 3000 nm, the ridge width is between 200 nm to 3000 nm, and depth of the groove is between 200 nm to 3000 nm; and
 b. an array of at least one cell migration unit on the nanopatterned substrate, each cell migration unit comprising:
  i. at least one migration pathway having a proximal and distal end,
  ii. at least one cell non-adherent region having a proximal and distal end, and iii. at least one cell loading region;
wherein the at least one migration pathway comprises a cell adherent surface having a width between 10 µm-500 µm, aligned parallel to the grooves and ridges,
wherein the at least one cell non-adherent region is aligned parallel to the grooves and ridges and is adjacent to the at least one migration pathway; and
wherein the at least one cell loading region is located at the proximal end of the at least one migration pathway and optionally, at the proximal end of at least one cell non-adherent region.

2. The array of claim 1, wherein the at least one migration pathway is coated with an extracellular matrix (ECM) component coating.

3. The array of claim 2, wherein the ECM component coating is not laminin.

4. The array of claim 2, wherein the ECM component coating further comprises at least one growth factor or chemotaxis agent.

5. The array of claim 1, wherein the cell migration unit comprises n migration pathways, n cell non-adherent regions, and at least one cell loading region located at the proximal end of the n migration pathways and n cell non-adherent regions.

6. The array of claim 1, wherein the cell migration unit comprises n migration pathways and:
n+1 cell non-adherent regions, and at least one cell loading region located at the proximal end of the n migration pathways and n+1 cell non-adherent regions, or
n+2 cell non-adherent regions, and at least one cell loading region located at the proximal end of the n migration pathways and n+2 cell non-adherent regions,
wherein each of the n migration pathways has a cell non-adherent region located on either side.

7. The array of claim 6, wherein n is selected from, 2, 3, 4, 5, 6, 7, 8, 9, 10, between 11-15, between 16-20 or more than 20 but less than 50.

8. The array of claim 6, wherein the migration pathways are of the same width, having a width selected from 10 µm, 20 µm, 30 µm, 40 µm, 50 µm, 60 µm, 70 µm, 80 µm, 90 µm, 100 µm, 110 µm, 120 µm, 130 µm, 140 µm, 150 µm, or greater than 150 µm but less than 500 µm.

9. The array of claim 6, wherein the migration pathways are of different widths, wherein the different widths of the migration pathways are selected from any or a combination of: 10 µm, 20 µm, 30 µm, 40 µm, 50 µm, 60 µm, 70 µm, 80 µm, 90 µm, 100 µm, 110 µm, 120 µm, 130 µm, 140 µm, 150 µm, or greater than 150 µm but less than 500 µm.

10. The array of claim 1, wherein the cell non-adherent region has a width is-selected from: between 50 µm-500 µm, or 150 µm-500 µm.

11. The array of claim 1, wherein
a. the groove width is selected from a width of: between 200 nm-800 nm, between 800 nm-1200 nm, 1000 nm-2000 nm or 2000 nm-3000 nm;
b. the ridge width is selected from a width of: between 200 nm to 800 nm, between 800 nm-1200 nm, 1000 nm-2000 nm or 2000 nm-3000 nm; and
c. groove depth is selected from a groove depth of: between 200 nm to 800 nm, between 800 nm-1200 nm, 1000 nm-2000 nm or 2000 nm-3000 nm.

12. The array of claim 1, wherein the at least one migration pathway and the at least one cell non-adherent region is between 0.5 mm-10 mm or 10 mm-20 mm in length.

13. The array of claim 1, wherein the array comprises at least 2 cell migration units or at least 3, 6, 8, 12, 24, 48, 96, 384, or 1536 cell migration units.

14. The array of claim 1, wherein the array is configured as a multi-well plate, each well of the multi-well plate comprising at least one cell migration unit, wherein the multi-well plate comprises any of: 2, 3, 4, 6, 8, 12, 24, 48, 96, 384 or 1536 wells.

15. The array of claim 1, further comprising a removable barrier located at the proximal end of the at least one migration pathway and optionally at the proximal end of the at least one cell non-adherent region, wherein the barrier prevents cells present in the cell loading region from entering the migration pathway.

16. The array of claim 15, wherein the removable barrier is a micropatterned stamp.

17. The array of claim 1, further comprising a population of mammalian cells, wherein the population of mammalian cells comprises cells attached to the nanopatterned substrate at least in the cell loading region.

18. A micro-well plate comprising the array of claim 1.

19. A method for measuring cell migration, the method comprising:
a. seeding a population of cells onto a nanopatterned substrate comprising parallel grooves and ridges, wherein the groove width is between 200 nm to 3000 nm, the ridge width is between 200 nm to 3000 nm, and groove height is between 200 nm to 3000 nm, wherein the cells are seeded at a cell loading region of at least one cell migration unit; wherein the cell migration unit comprises,
i. at least one migration pathway having a proximal and distal end,
ii. at least one cell non-adherent region having a proximal and distal end, and
iii. at least one cell loading region;
wherein the at least one migration pathway is aligned parallel to the grooves and ridges and comprises a cell-adherent surface, and is between 10 µm-500 µm in width;
wherein the at least one cell non-adherent region is aligned parallel to the grooves and ridges and is adjacent to the at least one migration pathway; and
wherein the at least one cell loading region is located at the proximal end of the at least one migration pathway and optionally, at the proximal end of at least one cell non-adherent region;
b. culturing the population of cells in the cell loading region to form a monolayer;
c. optionally removing a barrier located between the proximal end of the at least one cell migration pathway and the cell loading region;
d. culturing the population of cells for a selected period of time to allow migration of the cells along the migration pathway towards the distal end;
e. measuring the distance of cell migration of the population of cells towards the distal end of the migration pathway in the selected period of time.

20. The method of claim 19, further comprising capturing time-lapse images at desired intervals for a series of images during the selected period of time.

21. The method of claim 19, further comprising
a. measuring the distance of cell migration of a population of cells towards the distal end of the migration pathway in the selected period of time in the presence of a test agent, relative to the distance of cell migration of a population of the same cells in the absence of the test agent; or b. measuring the distance of cell migration of a population of tumor cells towards the distal end of the migration pathway in the selected period of time in the presence of a test agent, relative to the distance of cell migration of a population of the same tumor cells in the presence of different concentrations of the test agent, and/or the presence of an agent known to inhibit cell migration, and/or the presence of an agent known to promote cell migration; or c. measuring the distance of cell migration of a population of tumor cells towards the distal end of the migration pathway in the selected period of time in the presence of a test agent, relative to the distance of cell migration of a population of cells known to migrate at a particular rate.

22. The method of claim 19, wherein the population of cells is seeded in the cell loading region in a gel or hydrogel.

23. The method of claim 19, further comprising collecting a population of cells from the migration pathway after the selected period of time, wherein the population of cells that are collected are those that have migrated furthest along the migration pathway in the selected period of time, or located in the distal one-third of the migration pathway after the selected period of time.

* * * * *